United States Patent
Yang et al.

(10) Patent No.: US 11,569,453 B2
(45) Date of Patent: Jan. 31, 2023

(54) POLYCYCLIC COMPOUND AND ORGANIC LIGHT EMITTING ELEMENT COMPRISING SAME

(71) Applicant: LG CHEM, LTD., Seoul (KR)

(72) Inventors: Junghoon Yang, Daejeon (KR); Dong Hoon Lee, Daejeon (KR); Jungoh Huh, Daejeon (KR); Yongbum Cha, Daejeon (KR); Dong Uk Heo, Daejeon (KR); Miyeon Han, Daejeon (KR); Jae Tak Lee, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 282 days.

(21) Appl. No.: 16/768,831

(22) PCT Filed: Mar. 6, 2019

(86) PCT No.: PCT/KR2019/002602
§ 371 (c)(1),
(2) Date: Jun. 1, 2020

(87) PCT Pub. No.: WO2019/172649
PCT Pub. Date: Sep. 12, 2019

(65) Prior Publication Data
US 2021/0020848 A1 Jan. 21, 2021

(30) Foreign Application Priority Data
Mar. 6, 2018 (KR) .................. 10-2018-0026436

(51) Int. Cl.
*C07D 405/04* (2006.01)
*C07D 409/14* (2006.01)
(Continued)

(52) U.S. Cl.
CPC ........ *H01L 51/0072* (2013.01); *C07D 239/26* (2013.01); *C07D 239/74* (2013.01);
(Continued)

(58) Field of Classification Search
CPC .. C07D 405/04; C07D 409/14; C07D 401/10; H01L 51/00; H01L 51/50
See application file for complete search history.

(56) References Cited

U.S. PATENT DOCUMENTS

| | | |
|---|---|---|
| 2019/0067595 A1 | 2/2019 | Jang et al. |
| 2020/0185617 A1 | 6/2020 | Eum et al. |

FOREIGN PATENT DOCUMENTS

| | | |
|---|---|---|
| JP | 2004014334 | 1/2004 |
| KR | 10-1537499 | 7/2015 |

(Continued)

OTHER PUBLICATIONS

Kumar et al., "Synthesis and characterization of polybrominated fluorenes and their conversion to polyphenylated fluorenes and cyclopenta[def]triphenylene," Tetrahedron Letters 55:1931-1935 (2014).
(Continued)

*Primary Examiner* — Bruck Kifle
(74) *Attorney, Agent, or Firm* — Dentons US LLP

(57) ABSTRACT

Provided is a compound of Chemical Formula 1:

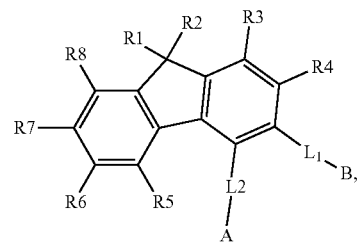

where A and B each independently is a substituted or unsubstituted aryl group, a substituted or unsubstituted monocyclic or dicyclic heteroaryl group, a substituted or unsubstituted dibenzofuran group, a substituted or unsubstituted benzonaphthofuran group, a substituted or unsubstituted dibenzothiophene group, a substituted or unsubstituted benzonaphthothiophene group, a substituted or unsubstituted phenoxazine group, a substituted or unsubstituted phenothiazine group, a substituted or unsubstituted phenanthroline group, a substituted or unsubstituted benzoquinoline group, a substituted or unsubstituted arylamine group, a substituted or unsubstituted silyl group, or a substituted or unsubstituted phosphine oxide group, or one of the following substituents:

(Continued)

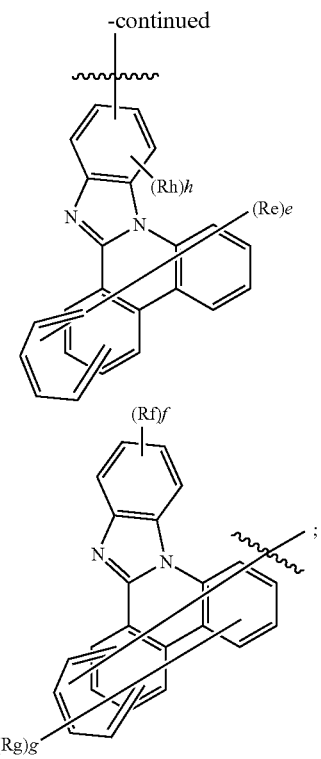

and an organic light emitting device including the same.

8 Claims, 2 Drawing Sheets

(51) Int. Cl.
C07D 401/10 (2006.01)
H01L 51/00 (2006.01)
H01L 51/50 (2006.01)
C07D 239/26 (2006.01)
C07D 239/74 (2006.01)
C07D 251/24 (2006.01)
C07D 403/10 (2006.01)

(52) U.S. Cl.
CPC ......... C07D 251/24 (2013.01); C07D 401/10 (2013.01); C07D 403/10 (2013.01); H01L 51/0067 (2013.01); H01L 51/5072 (2013.01); H01L 51/5092 (2013.01); H01L 51/5096 (2013.01)

(56) References Cited

FOREIGN PATENT DOCUMENTS

| KR | 10-2016-0078237 | 7/2016 |
| KR | 10-20160079415 | 7/2016 |
| KR | 10-2018-0020522 | 2/2018 |
| KR | 10-20180015546 | 2/2018 |
| WO | 2018038544 | 3/2018 |
| WO | 2018190522 | 10/2018 |

OTHER PUBLICATIONS

DataBase Registry, retrieved from STN Database accession numbers RN 2179126-61-3 (entered on Feb. 22, 2018) RN 22815-16-3 (entered on Nov. 16, 1984); RN 22815-18-5 (entered Nov. 16, 1984) and RN 22815-19-6 (entered on Nov. 16, 1984).

【FIG. 1】
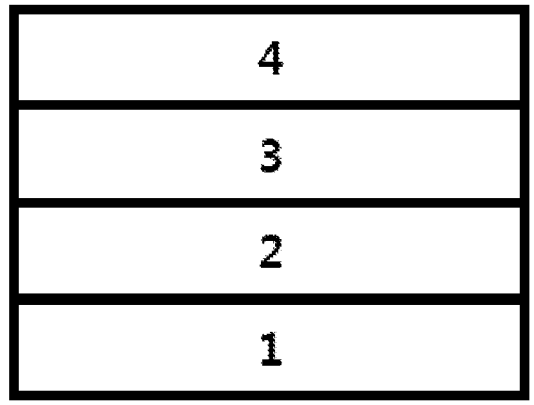
【FIG. 2】
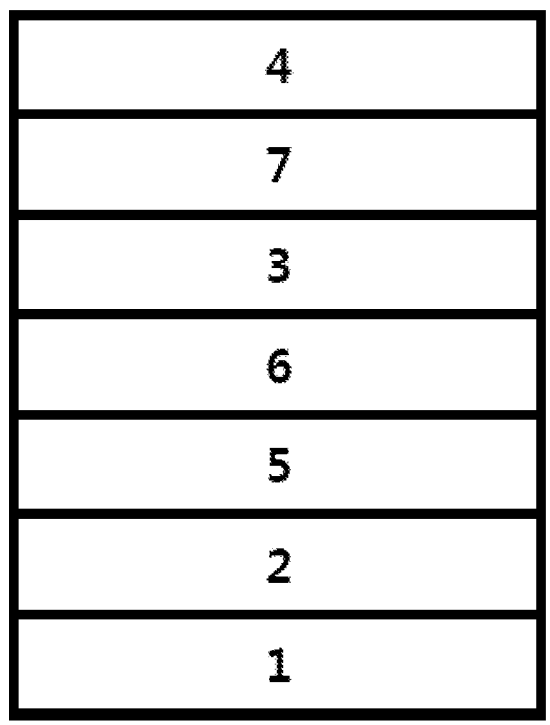

【FIG. 3】
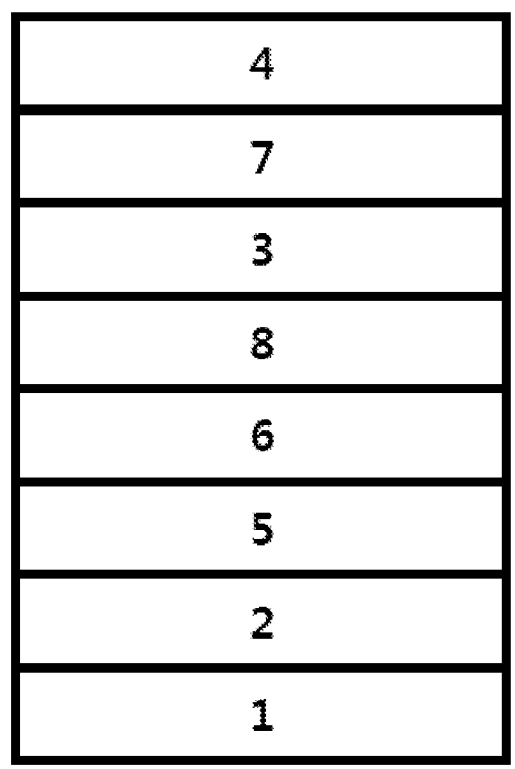

POLYCYCLIC COMPOUND AND ORGANIC LIGHT EMITTING ELEMENT COMPRISING SAME

CROSS-REFERENCE TO RELATED APPLICATIONS

This application is a National Stage Application of International Application No. PCT/KR2019/002602 filed on Mar. 6, 2019, which claims priority to and the benefits of Korean Patent Application No. 10-2018-0026436, filed with the Korean Intellectual Property Office on Mar. 6, 2018, the entire contents of which are incorporated herein by reference.

TECHNICAL FIELD

The present specification relates to a polycyclic compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a polycyclic compound, and an organic light emitting device including the same.

Technical Solution

One embodiment of the present specification provides a compound of Chemical Formula 1:

Chemical Formula 1

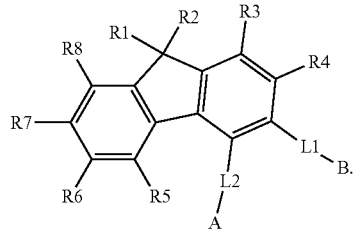

In Chemical Formula 1:

R1 and R2 are the same as or different from each other, and each independently is a substituted or unsubstituted alkyl group, a substituted or unsubstituted alkylaryl group, or a substituted or unsubstituted aryl group;

R3 to R8 are the same as or different from each other, and each independently is hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted alkenyl group, a substituted or unsubstituted silyl group, a substituted or unsubstituted amine group, a substituted or unsubstituted aryl group, or a substituted or unsubstituted heteroaryl group;

L1 and L2 are the same as or different from each other, and each independently is a direct bond, a substituted or unsubstituted arylene group, a substituted or unsubstituted monocyclic or dicyclic heteroarylene group, a substituted or unsubstituted divalent dibenzofuran group, a substituted or unsubstituted divalent dibenzothiophene group, a substituted or unsubstituted divalent phenoxazine group, or a substituted or unsubstituted divalent phenothiazine group;

A and B are the same as or different from each other, and each independently is a substituted or unsubstituted aryl group, a substituted or unsubstituted monocyclic or dicyclic heteroaryl group, a substituted or unsubstituted dibenzofuran group, a substituted or unsubstituted benzonaphthofuran group, a substituted or unsubstituted dibenzothiophene group, a substituted or unsubstituted benzonaphthothiophene group, a substituted or unsubstituted phenoxazine group, a substituted or unsubstituted phenothiazine group, a substituted or unsubstituted phenanthroline group, a substituted or unsubstituted benzoquinoline group, a substituted or unsubstituted arylamine group, a substituted or unsubstituted silyl group; or a substituted or unsubstituted phosphine oxide group, or one of the following substituents:

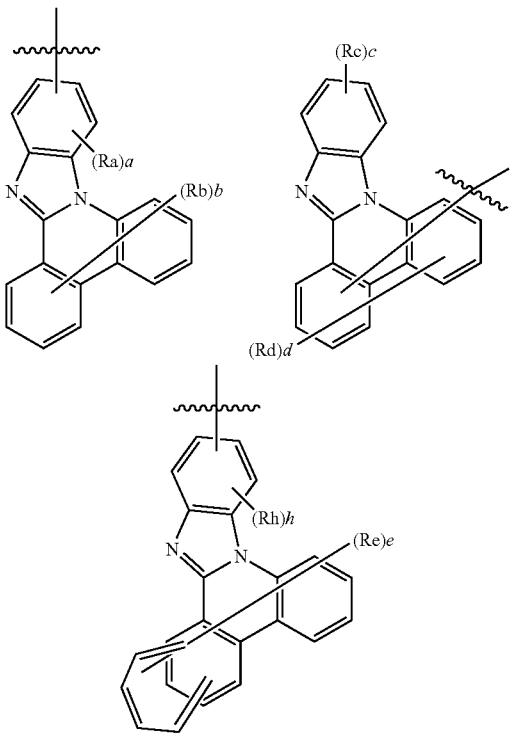

-continued

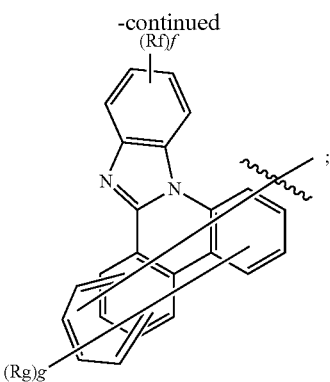

and in the substituents, Ra to Rh are the same as or different from each other, and each independently is hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted alkenyl group, a substituted or unsubstituted silyl group, a substituted or unsubstituted amine group, a substituted or unsubstituted aryl group, or a substituted or unsubstituted heteroaryl group, a and h are each an integer of 0 to 3, b is an integer of 0 to 8, c and f are each an integer of 0 to 4, d is an integer of 0 to 7, e is an integer of 0 to 10, and g is an integer of 0 to 9.

Another embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

Advantageous Effects

A compound according to one embodiment of the present specification can be used as a material of an organic material layer of an organic light emitting device, and by using the same, enhanced efficiency, low driving voltage and/or enhanced lifetime properties can be obtained in the organic light emitting device.

DESCRIPTION OF DRAWINGS

FIGS. 1 to 3 illustrate organic light emitting devices according to embodiments of the present specification.

REFERENCE NUMERAL

1: Substrate
2: Anode
3: Light Emitting Layer
4: Cathode
5: Hole Injection Layer
6: Hole Transfer Layer
7: Electron Injection and Transfer Layer
8: Electron Blocking Layer

DETAILED DESCRIPTION

Hereinafter, the present specification will be described in more detail.

One embodiment of the present specification provides a compound of Chemical Formula 1. Specifically, one embodiment of the present specification provides a compound having a specific substituent at carbon positions 3 and 4 of fluorene. When having substituents of -L1-B and -L2-A respectively at carbon positions 3 and 4 of fluorene as above, a conjugation length between R1 and R2 and -L1-B and -L2-A is extended compared to when carbon positions 1 and 2 of fluorene are substituted with substituents of -L1-B and -L2-A, and electrical and thermal properties of the fluorene group itself can be more effectively exhibited.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted alkenyl group, a substituted or unsubstituted silyl group, a substituted or unsubstituted boron group, a substituted or unsubstituted amine group, a substituted or unsubstituted aryl group, and a substituted or unsubstituted heterocyclic group, or being substituted with a substituent linking two or more substituents among the substituents illustrated above, or having no substituents. For example, "a substituent linking two or more substituents" can include an aryl group substituted with an aryl group, an aryl group substituted with a heteroaryl group, a heterocyclic group substituted with an aryl group, an aryl group substituted with an alkyl group and the like.

In the present specification, the alkyl group can be linear or branched, and although not particularly limited thereto, the number of carbon atoms is preferably from 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof include cyclopropyl, cyclobutyl, cyclopentyl, 3-methylcyclopentyl, 2,3-dimethyl-cyclopentyl, cyclohexyl, 3-methylcyclohexyl, 4-methylcyclohexyl, 2,3-dimethylcyclohexyl, 3,4,5-trimethyl-cyclohexyl, 4-tert-butylcyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 30. Specific examples thereof can include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethyl-butyloxy, 2-ethylbutyloxy, n-octyloxy, n-nonyloxy, n-decyloxy, benzyloxy, p-methylbenzyloxy and the like, but are not limited thereto.

In the present specification, the amine group can be selected from the group consisting of —NH$_2$, an alkylamine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 30. Specific examples of the amine group can include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenyl-naphthylamine group, a ditolylamine group, an N-phenyl-tolylamine group, a triphenylamine group, an N-phenyl-biphenylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, the arylamine group is an amine group in which N of the amine group is substituted with an aryl group, and means an amine group substituted with one or two aryl groups. The arylamine group can be of —NRxRy, and at least one of Rx and Ry is an aryl group, and the other one can be hydrogen, an alkyl group or an aryl group. Herein, the alkyl group and the aryl group can include those described in the present specification.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above.

In the present specification, the alkenyl group can be linear or branched, and although not particularly limited thereto, the number of carbon atoms is preferably from 2 to 30. Specific examples thereof can include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis-(diphenyl-1-yl)vinyl-1-yl, a stilbenyl group, a styrenyl group and the like, but are not limited thereto.

In the present specification, specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific example of the polycyclic aryl group can include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the fluorenyl group can be substituted, and adjacent groups can bond to each other to form a ring.

When the fluorenyl group is substituted,

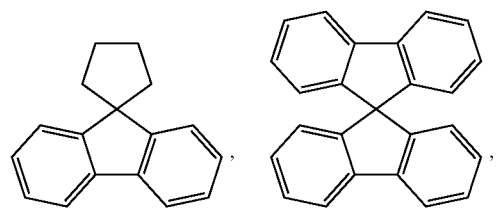
,

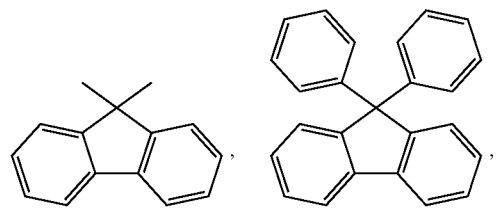
,

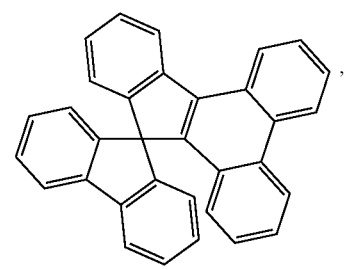
,

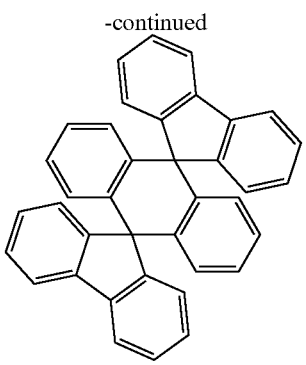

and the like can be included. However, the structure is not limited thereto.

In the present specification, the aryl group in the aryloxy group, the N-arylalkylamine group and the N-arylheteroarylamine group is the same as the examples of the aryl group described above. Specific examples of the aryloxy group can include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like.

In the present specification, the heteroaryl group is a group including one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30, and the heteroaryl group can be monocyclic or polycyclic. Examples of the heterocyclic group can include a thiophene group, a furan group, a pyrrole group, an imidazole group, a thiazole group, an oxazole group, an oxadiazole group, a pyridyl group, a bipyridyl group, a pyrimidyl group, a triazinyl group, a triazole group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazole group, a benzoxazole group, a benzimidazole group, a benzothiazole group, a benzocarbazole group, a dibenzopyrrole group, an indole group, a benzothiophene group, a dibenzothiophene group, a benzofuran group, a benzoquinolyl group, a benzonaphthothiophene group, a benzonaphthofuran group, a phenanthrolinyl group, a thiazole group, an isoxazole group, an oxadiazole group, a thiadiazole group, a benzothiazole group, a phenoxazine group, a phenothiazine group, a dibenzofuran group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, examples of the aryl group and the heteroaryl group described above can be applied to the arylene group and the heteroarylene group except for being divalent.

According to one embodiment of the present specification, -L2-A and -L1-B are the same as each other. In this case, properties of a substituent obtained from intermolecular interactions can be enhanced as a dimer.

According to one embodiment of the present specification, -L2-A and -L1-B are different from each other. Being different means having a different substituent structure or having a different substituent bonding position. In this case, electron transfer capability, band gap, energy level and thermal properties can be more readily controlled. In addition, electrical and thermal properties depending on the position of substitution can be readily predicted, and in particular, hole or electron transfer properties can be actively controlled.

According to one embodiment of the present specification, A and B are the same as or different from each other, and each independently is a substituted or unsubstituted aryl group having 6 to 30 carbon atoms, a substituted or unsubstituted arylamine group having 6 to 30 carbon atoms, a substituted or unsubstituted silyl group, a substituted or unsubstituted arylphosphine oxide group having 6 to 30 carbon atoms, a substituted or unsubstituted alkylphosphine oxide group having 1 to 30 carbon atoms, a substituted or unsubstituted pyridine group, a substituted or unsubstituted pyrimidine group, a substituted or unsubstituted triazine group, a substituted or unsubstituted quinazoline group, a substituted or unsubstituted quinolyl group, a substituted or unsubstituted isoquinolyl group, a substituted or unsubstituted benzimidazole group, a substituted or unsubstituted benzothiazole group, a substituted or unsubstituted benzoxazole group, a substituted or unsubstituted phenanthroline group, or a substituted or unsubstituted benzoquinolyl group, or one of the following substituents:

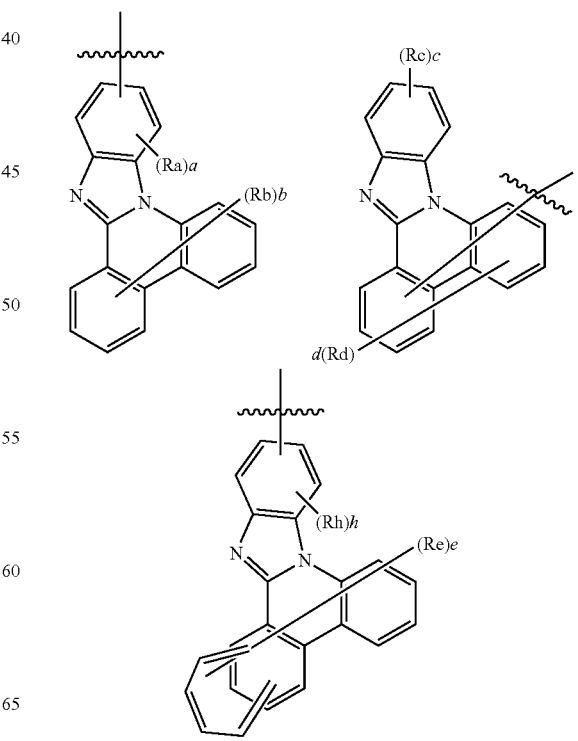

-continued

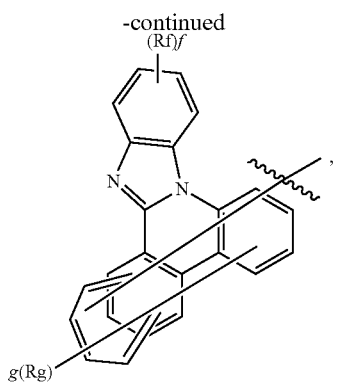

wherein Ra to Rh and a to h have the same definitions as in Chemical Formula 1.

According to one embodiment of the present specification, when A and B are substituted, the substituent can be deuterium, a nitrile group, an alkyl group, an aryl group, a heteroaryl group, a silyl group substituted with an alkyl group or an aryl group, or an arylphosphine oxide group.

According to one embodiment of the present specification, when A and B are substituted, the substituent can be deuterium, a nitrile group, a C1-C20 alkyl group, a C6-C30 aryl group, a C2-C30 heteroaryl group, a silyl group substituted with a C1-C6 alkyl group or a C6-C20 aryl group, or a C6-C30 arylphosphine oxide group.

According to one embodiment of the present specification, at least one of A and B is a substituted or unsubstituted monocyclic or dicyclic N-containing heteroaryl group, a substituted or unsubstituted phenanthroline group, a substituted or unsubstituted benzoquinolyl group, a substituted or unsubstituted silyl group, or a substituted or unsubstituted phosphine oxide group, or one of the following substituents:

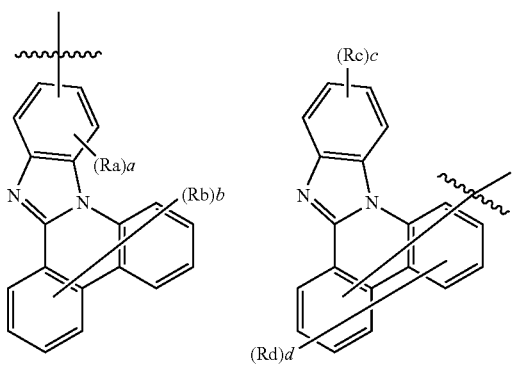

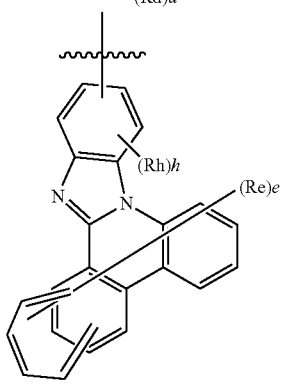

-continued

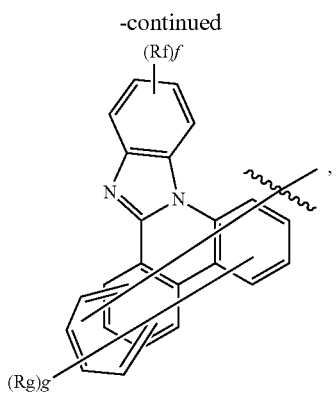

wherein Ra to Rh and a to h have the same definitions as above.

According to one embodiment of the present specification, at least one of A and B is a substituted or unsubstituted pyridine group, a substituted or unsubstituted pyrimidine group, a substituted or unsubstituted triazine group, a substituted or unsubstituted quinazoline group, a substituted or unsubstituted quinolyl group, a substituted or unsubstituted isoquinolyl group, a substituted or unsubstituted benzimidazole group, a substituted or unsubstituted benzothiazole group, a substituted or unsubstituted benzoxazole group, a substituted or unsubstituted phenanthroline group, a substituted or unsubstituted benzoquinolyl group, a substituted or unsubstituted silyl group, or a substituted or unsubstituted phosphine oxide group, or one of the following substituents:

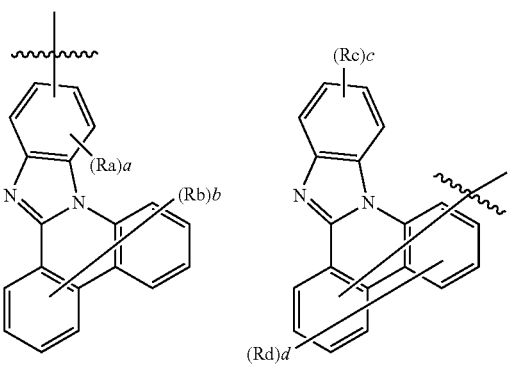

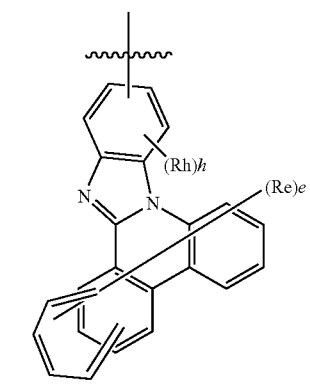

-continued

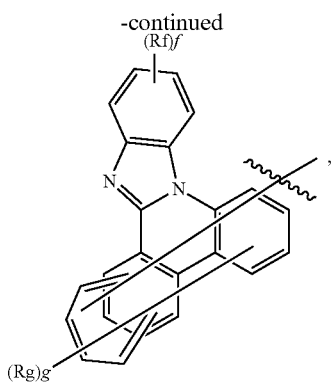

wherein Ra to Rh and a to h have the same definitions as above.

By at least one of A and B including an N-containing ring, specifically, a substituted or unsubstituted pyridine group, a substituted or unsubstituted pyrimidine group, a substituted or unsubstituted triazine group, a substituted or unsubstituted quinazoline group, a substituted or unsubstituted quinolyl group, a substituted or unsubstituted isoquinolyl group, a substituted or unsubstituted benzimidazole group, a substituted or unsubstituted benzothiazole group, a substituted or unsubstituted benzoxazole group, a substituted or unsubstituted phenanthroline group, a substituted or unsubstituted benzoquinolyl group, or a heteroaryl group including one or more nitrogen atoms such as the above-described structural formulae, more advantageous effects can be obtained in terms of electron injection and transfer capability.

According to one embodiment of the present specification, when A and B further have a substituent, the substituent can be a substituent selected from among a nitrile group, an alkyl group, a silyl group substituted with an alkyl group or an aryl group, an arylamine group, an aryl group, a heteroaryl group, aryl, an alkylphosphine oxide group, and an arylphosphine oxide group, or a substituent having two or more thereof bonding to each other.

According to one embodiment of the present specification, L1 and L2 are the same as or different from each other, and each independently is selected from among a direct bond, phenylene, biphenylylene, terphenylylene, quaterphenylylene, naphthylene, anthracenylene, fluorenylene unsubstituted or substituted with alkyl or aryl, phenanthrenylene, pyrenylene, and triphenylylene.

According to one embodiment of the present specification, L1 and L2 are the same as or different from each other, and can be each independently a direct bond or selected from among the following structural formulae:

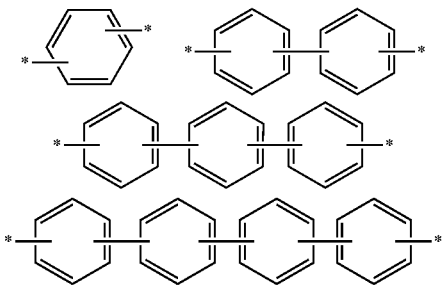

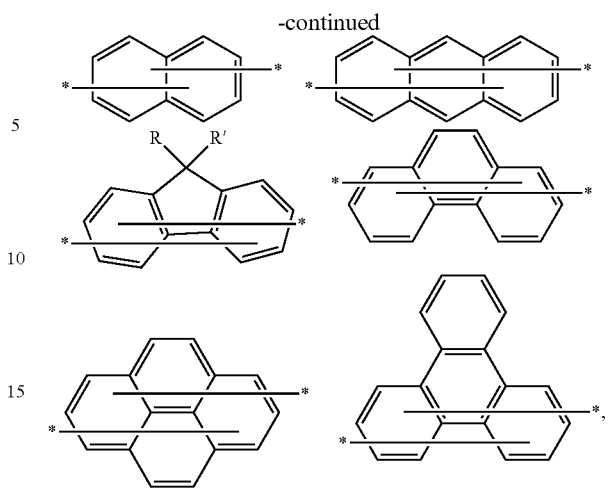

wherein R and R' are an alkyl group or an aryl group. For example, R and R' are a methyl group or a phenyl group.

According to one embodiment of the present specification, L1 and L2 are the same as or different from each other, and can be each independently a direct bond or selected from among the following structural formulae:

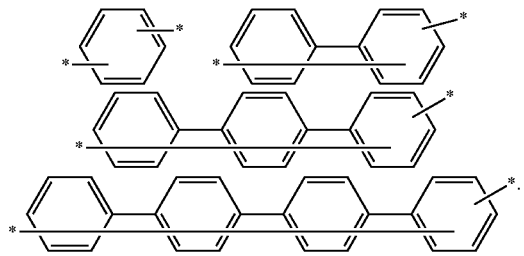

According to one embodiment of the present specification, L1 and L2 are the same as or different from each other, and each independently is a direct bond, phenylene or a biphenylylene group.

According to one embodiment of the present specification, L1 and L2 are the same as or different from each other, and each independently is a direct bond or phenylene.

According to one embodiment of the present specification, L1 and L2 are the same as or different from each other, and each independently is a direct bond, p-phenylene or m-phenylene.

According to one embodiment of the present specification, A and B of Chemical Formula 1 can be any one of the following structural formulae:

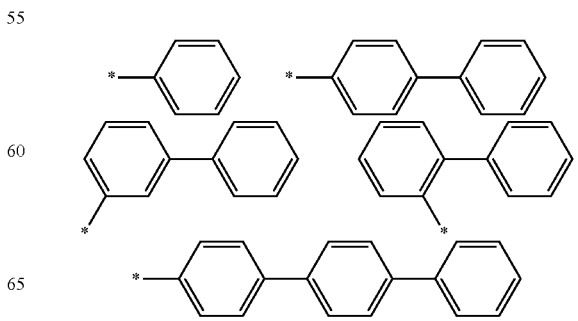

-continued
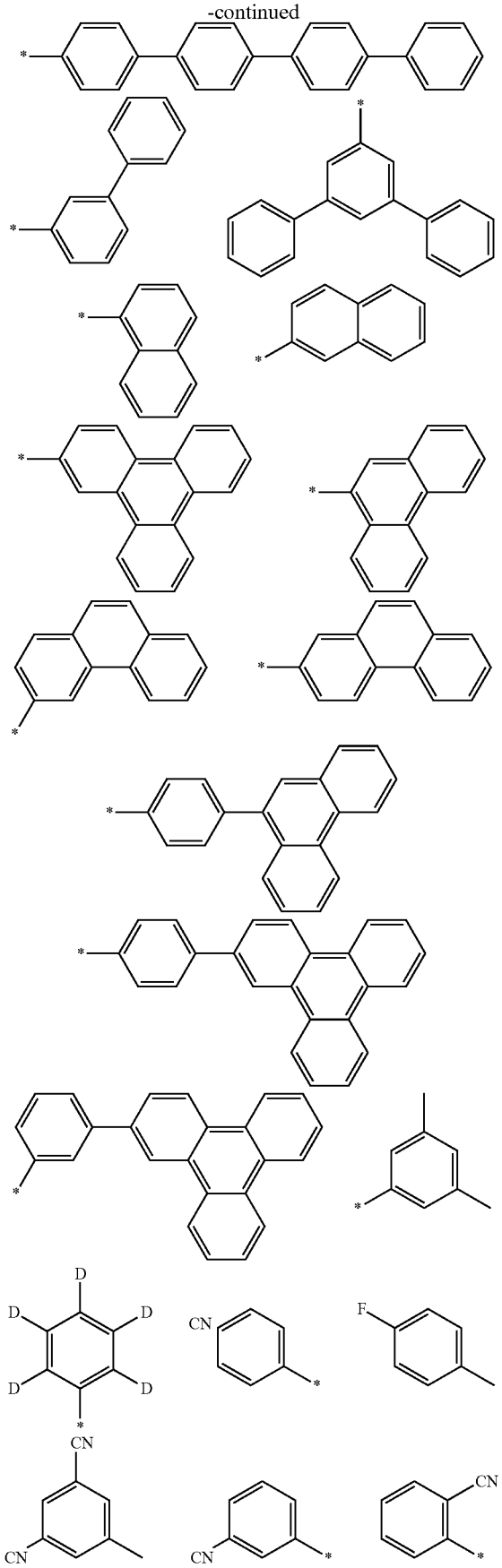
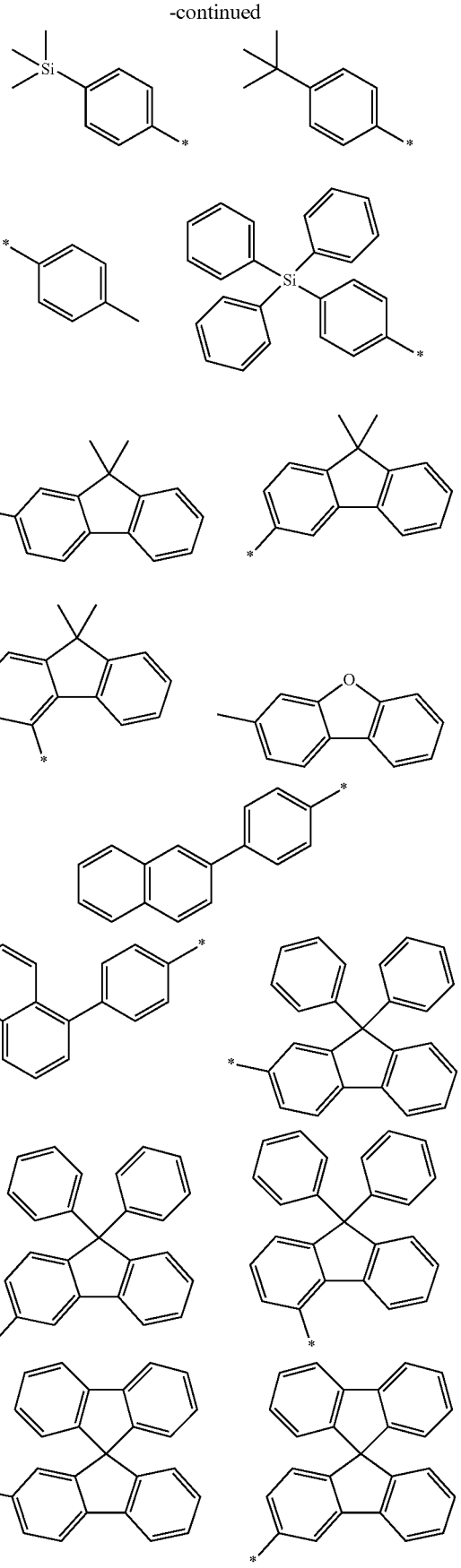

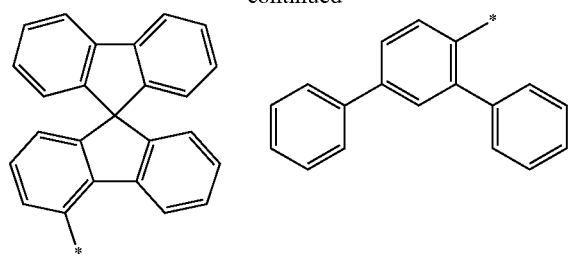
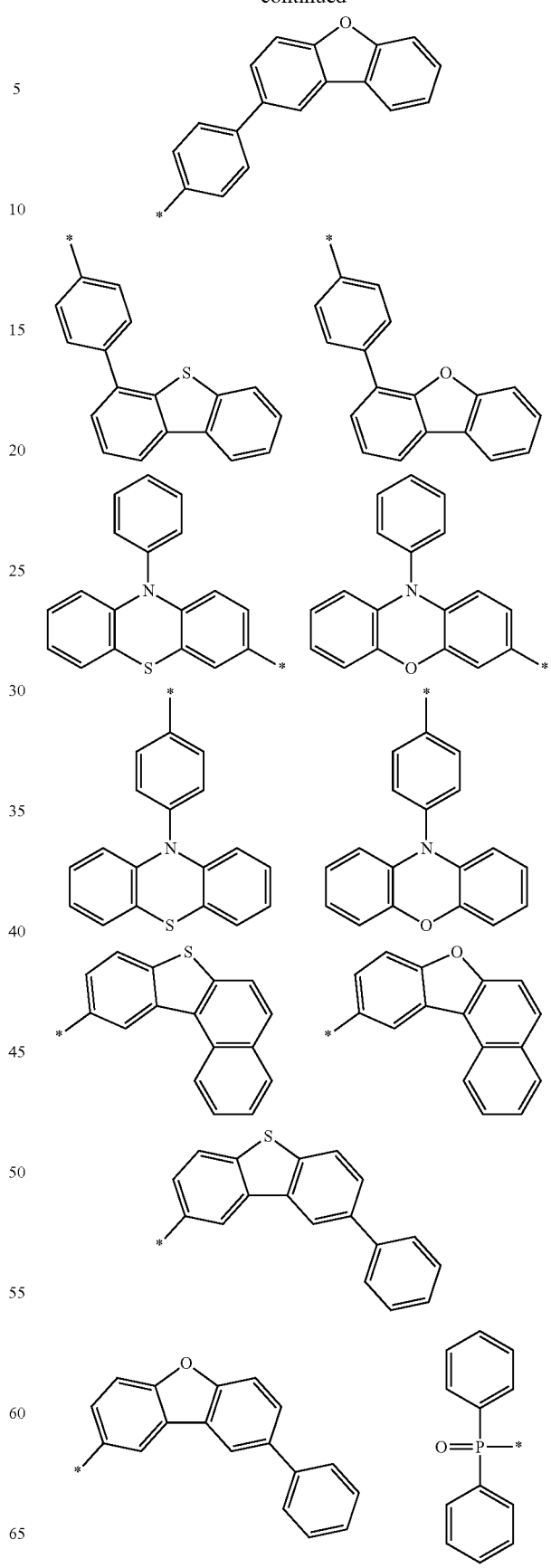

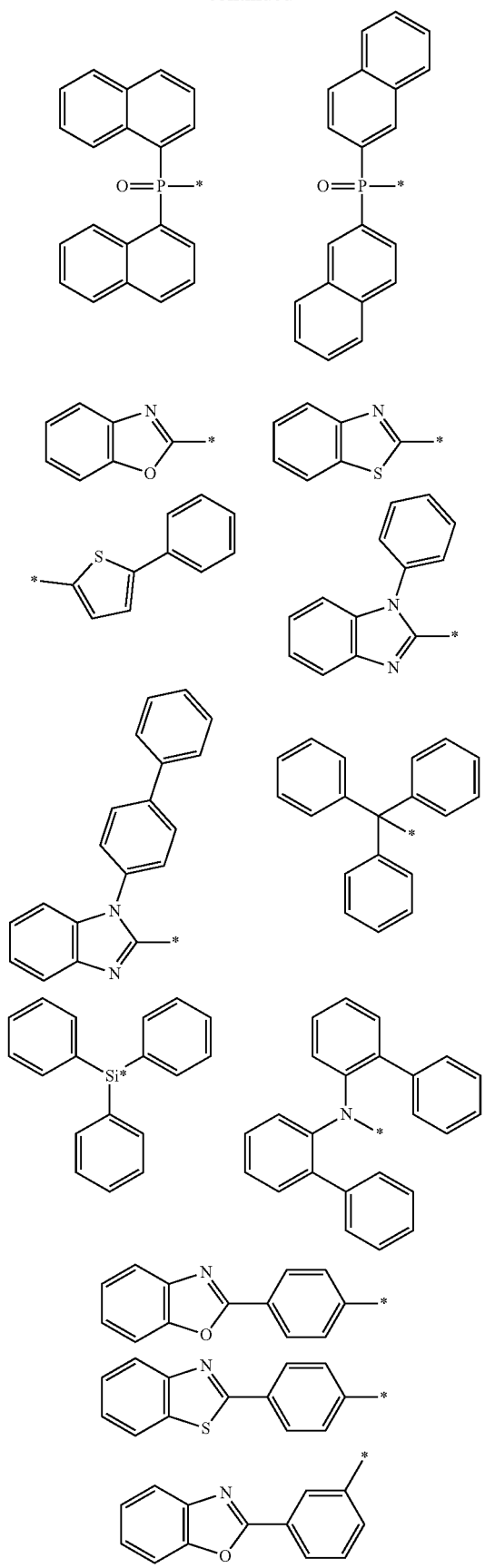
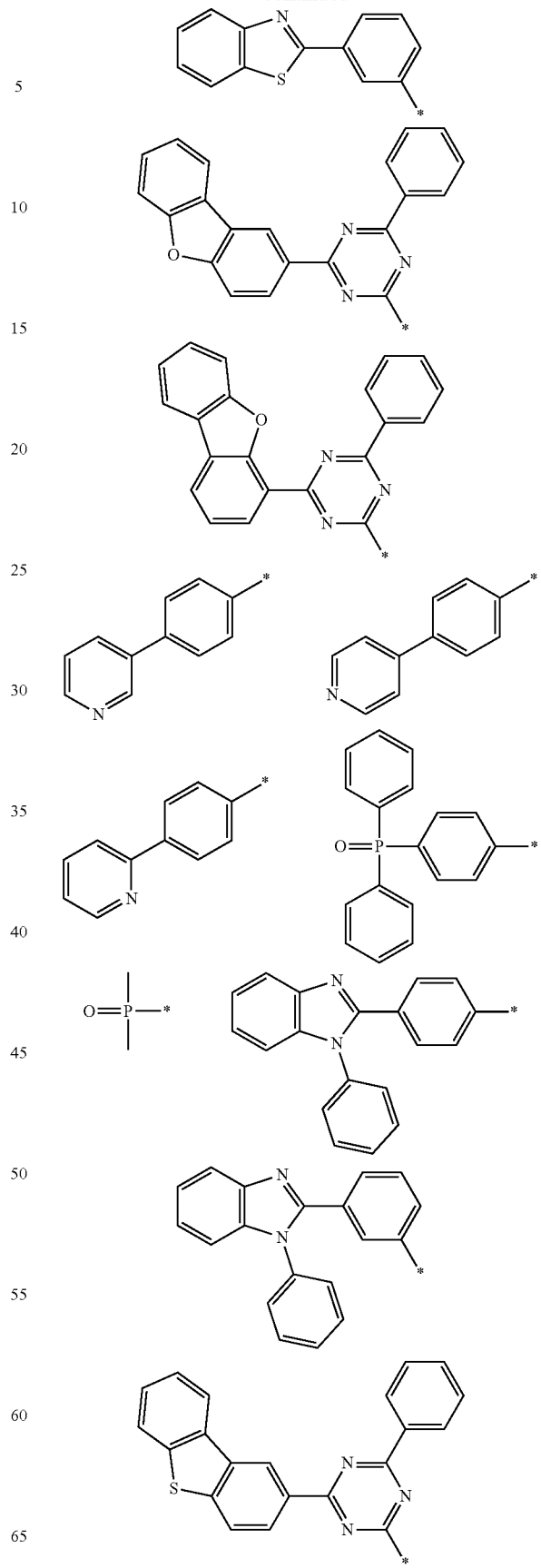

-continued
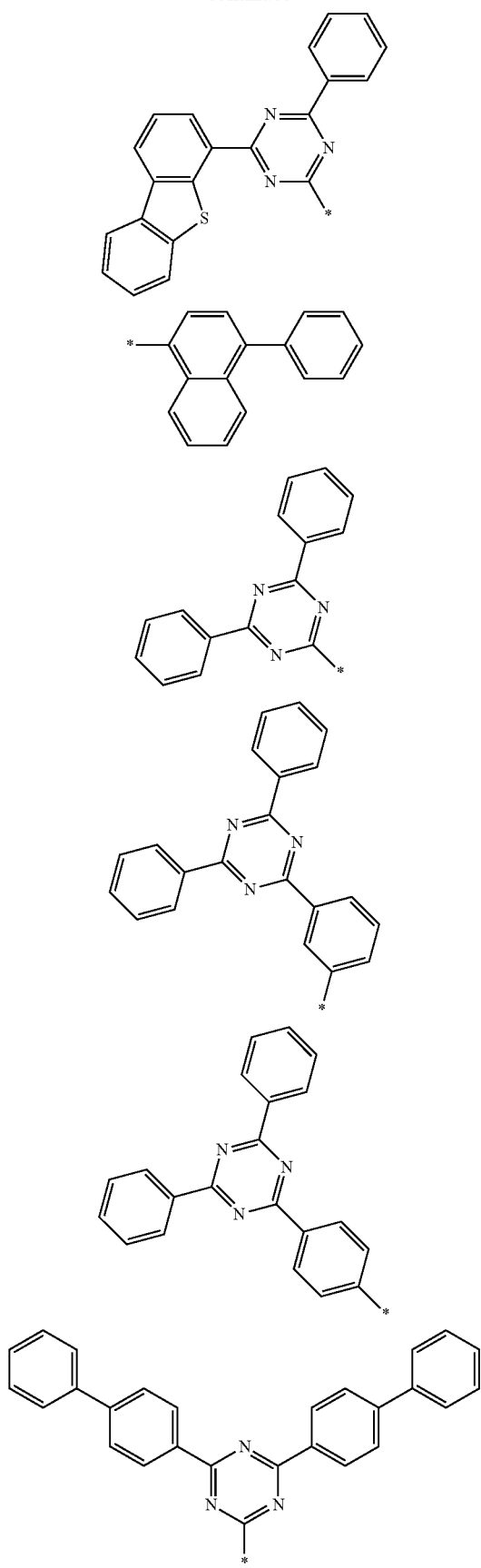
-continued
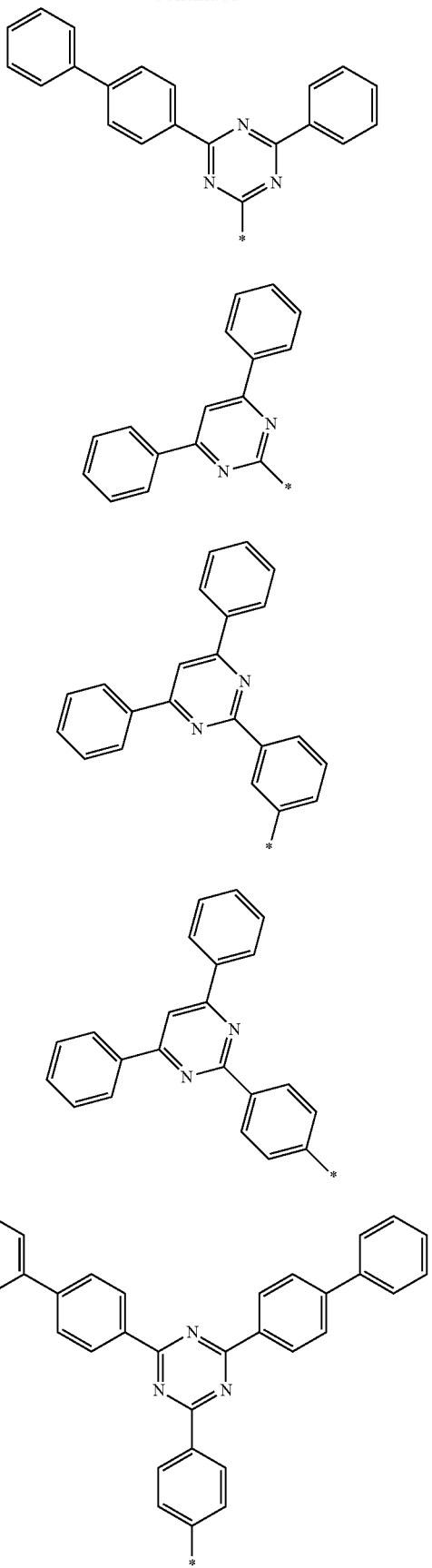

-continued
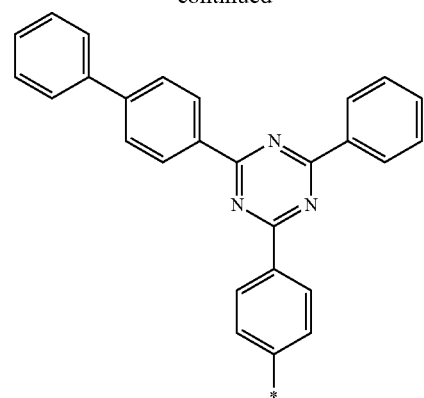
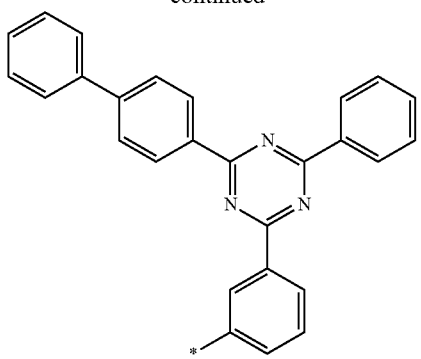
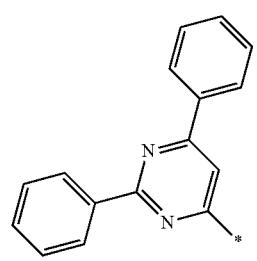
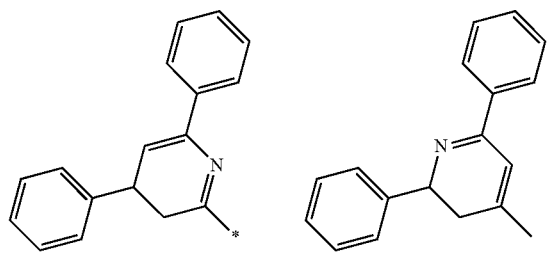
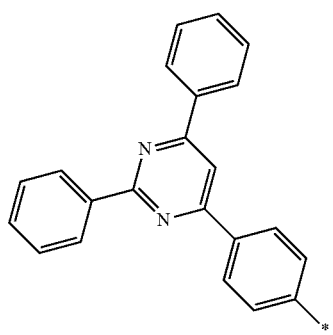
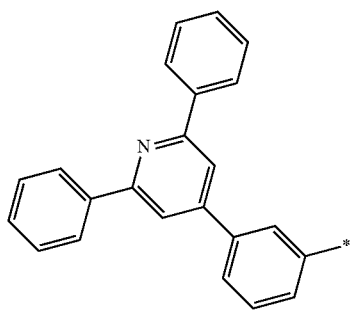
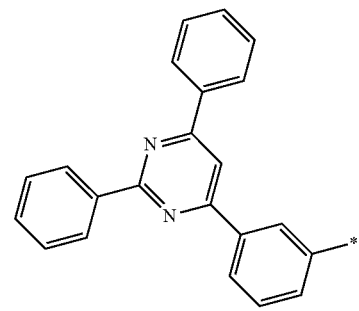
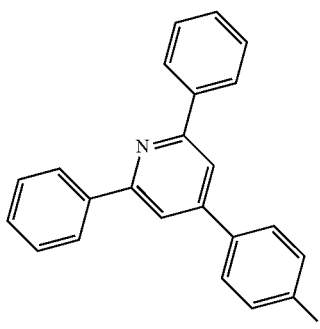
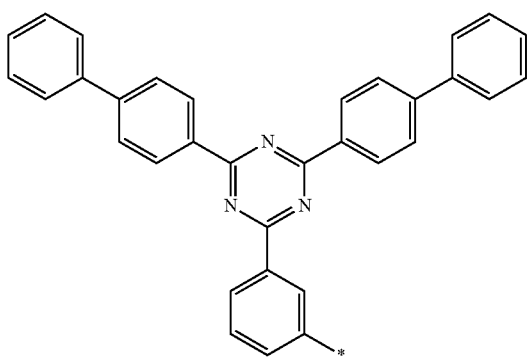
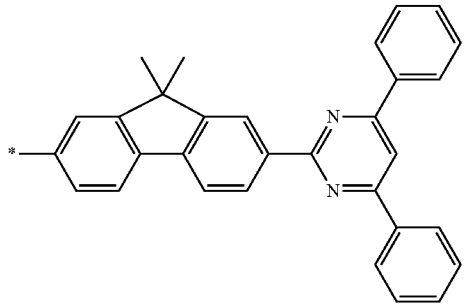

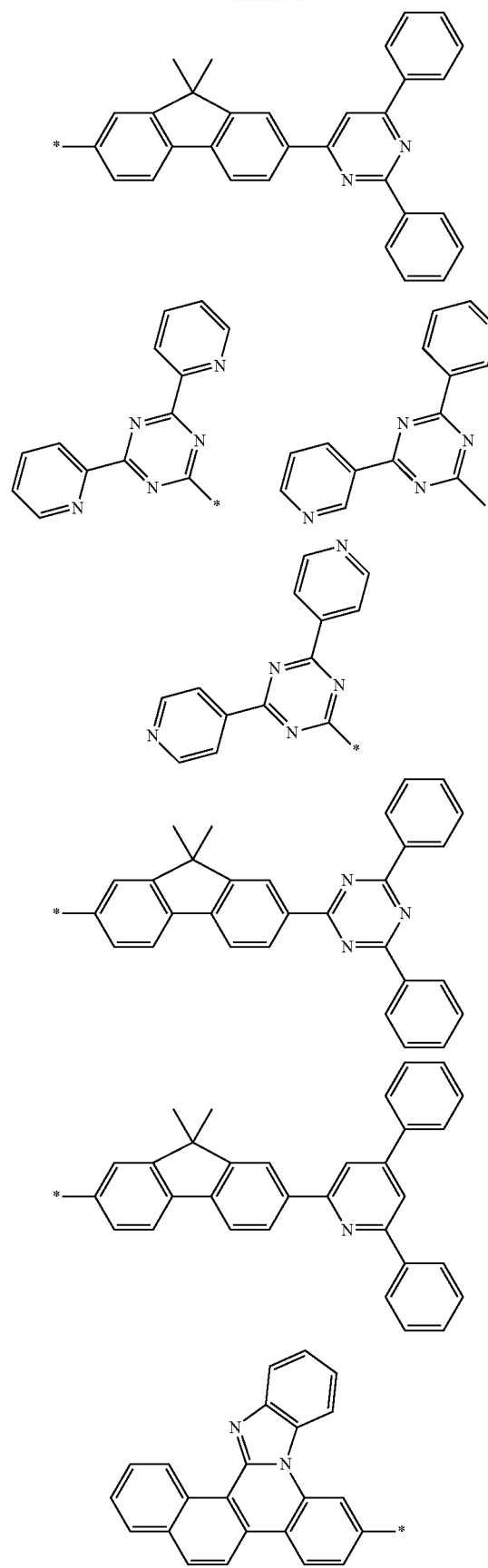
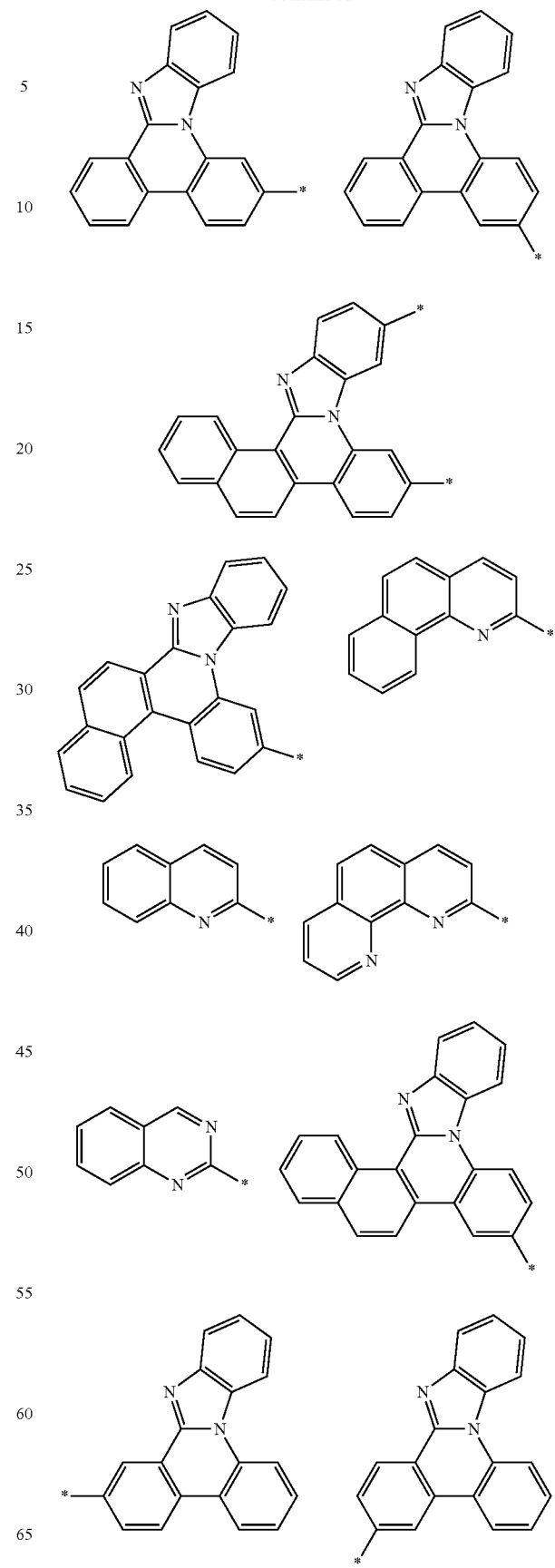

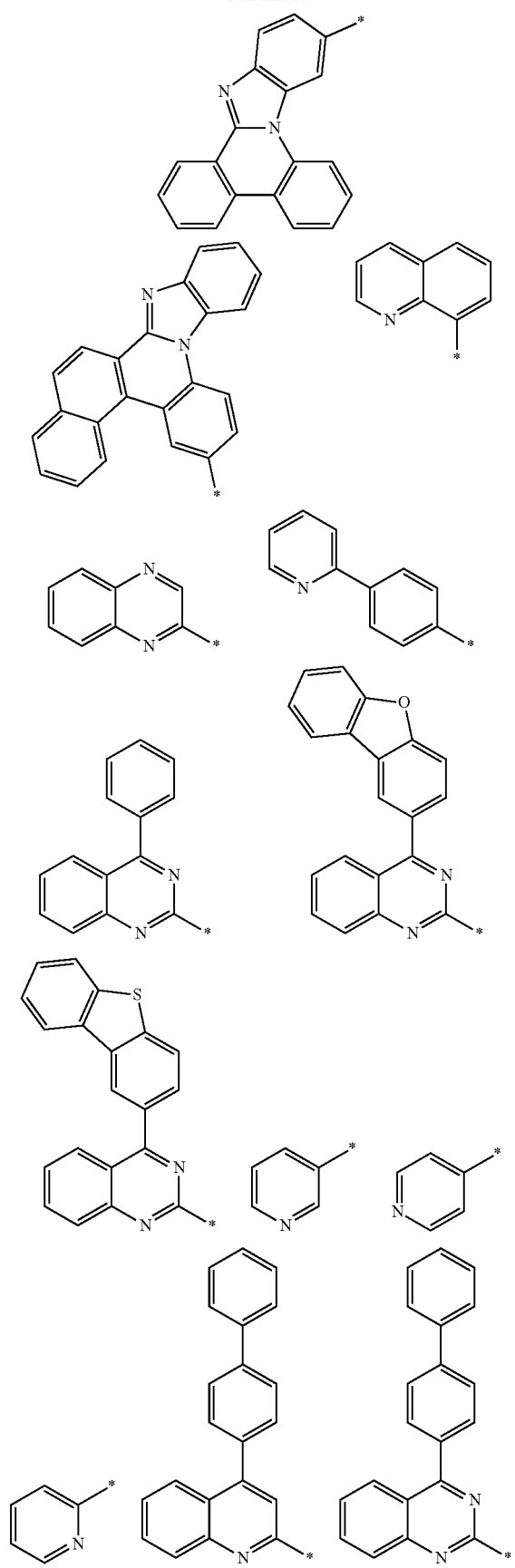
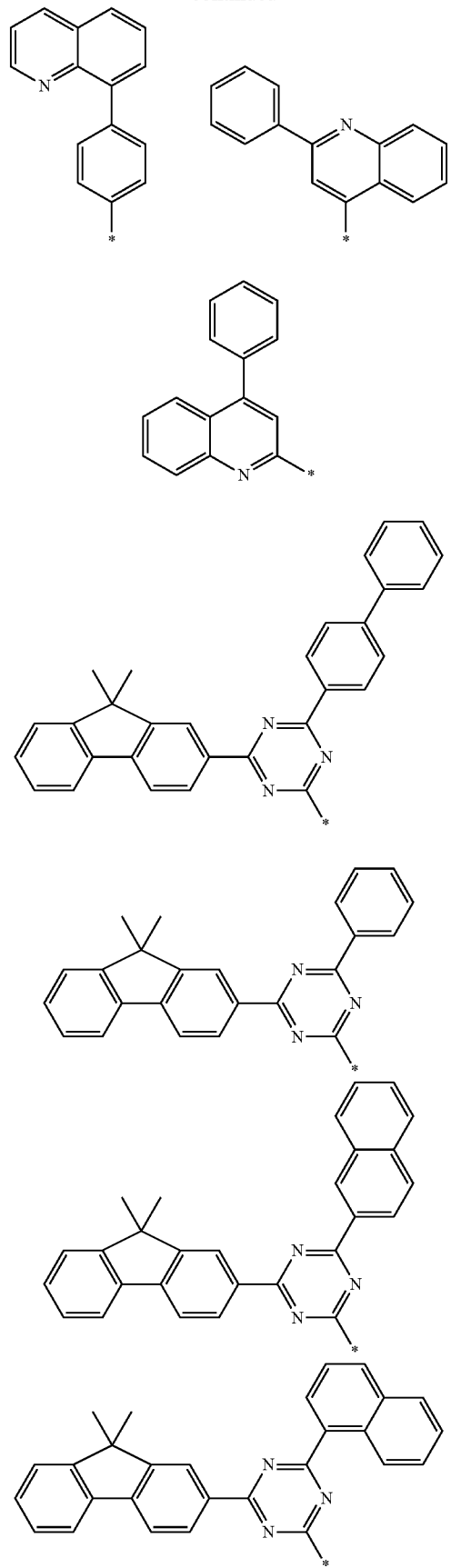

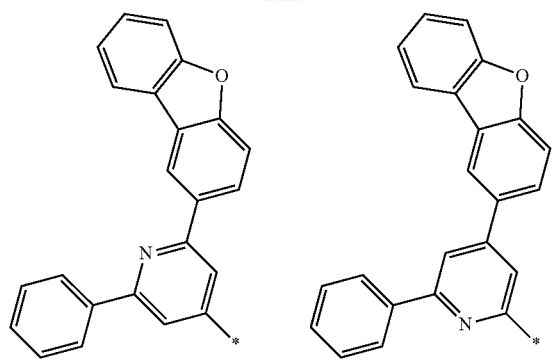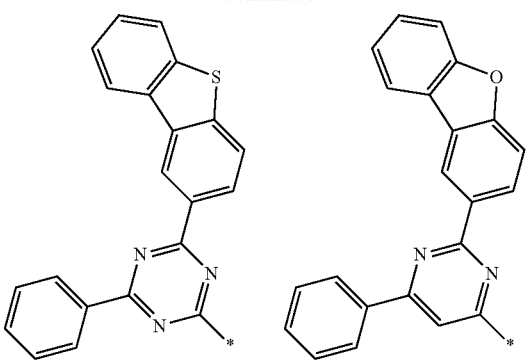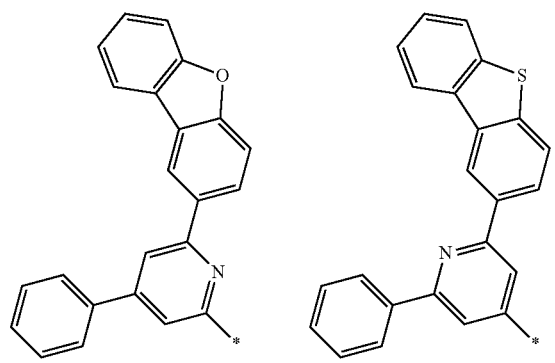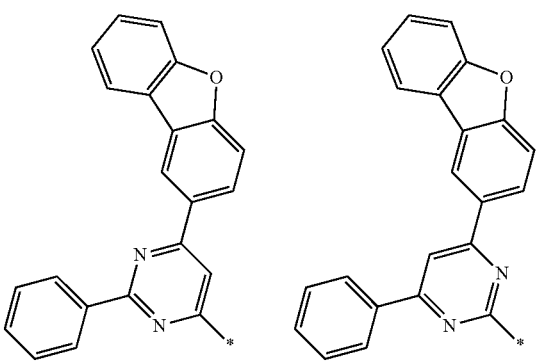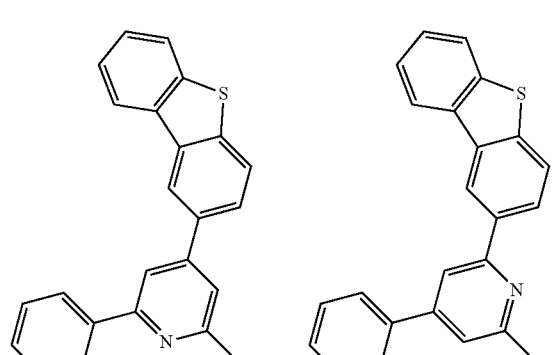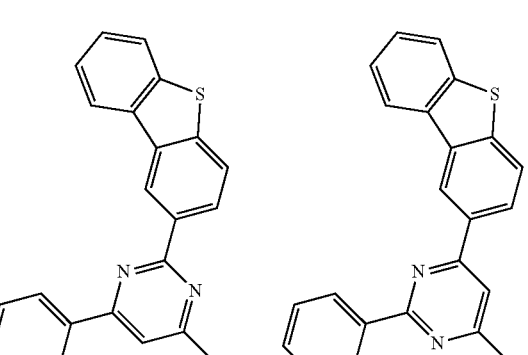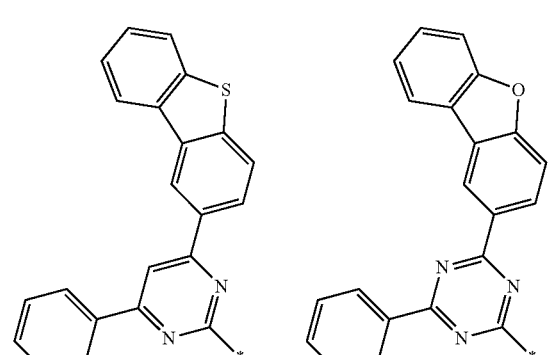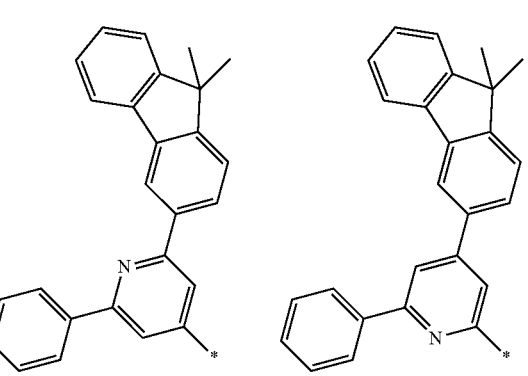

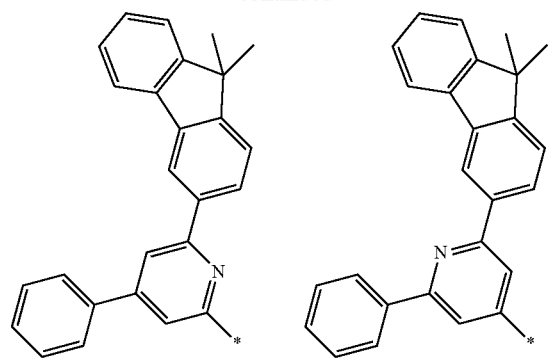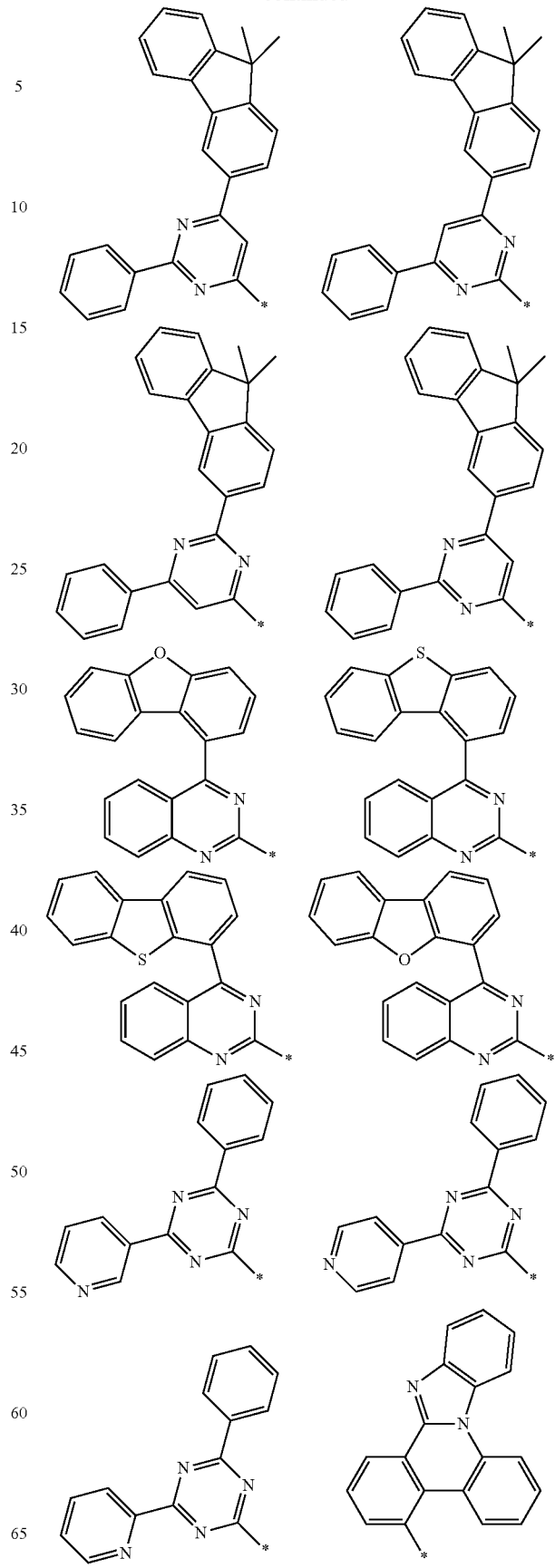

-continued

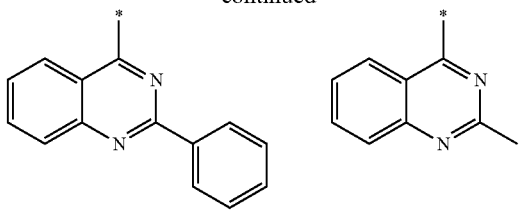

According to one embodiment of the present specification, R1 and R2 are the same as or different from each other, and each independently is an alkyl group. In this case, efficiency of a device using the compound can be enhanced.

According to one embodiment of the present specification, R1 and R2 are the same as or different from each other, and each independently is a C1-C20 alkyl group.

According to one embodiment of the present specification, R1 and R2 are the same as or different from each other, and each independently is a C1-C6 alkyl group.

According to one embodiment of the present specification, R1 and R2 are a methyl group.

According to one embodiment of the present specification, R1 and R2 are the same as or different from each other, and each independently is an aryl group. In this case, reversal properties of a material and device lifetime are enhanced.

According to one embodiment of the present specification, R1 and R2 are the same as or different from each other, and each independently is a C6-C20 aryl group.

According to one embodiment of the present specification, R1 and R2 are a phenyl group.

According to one embodiment of the present specification, R1 is an aryl group, and R2 is an alkyl group. In this case, each advantage of R1 and R2 being all alkyl and R1 and R2 being all aryl can be moderately obtained.

According to one embodiment of the present specification, R1 and R2 can all be an alkyl group, R1 and R2 can all be an aryl group, or R1 is an alkyl group and R2 is an aryl group.

According to one embodiment of the present specification, R1 is a C6-C20 aryl group, and R2 is a C1-C20 alkyl group.

According to one embodiment of the present specification, R1 is a C6-C20 aryl group, and R2 is a C1-C6 alkyl group.

According to one embodiment of the present specification, R1 is a phenyl group, and R2 is a methyl group.

According to one embodiment of the present specification, R3 to R8 are hydrogen or deuterium.

In the present specification, Chemical Formula 1 can be any one selected from among the following compounds:

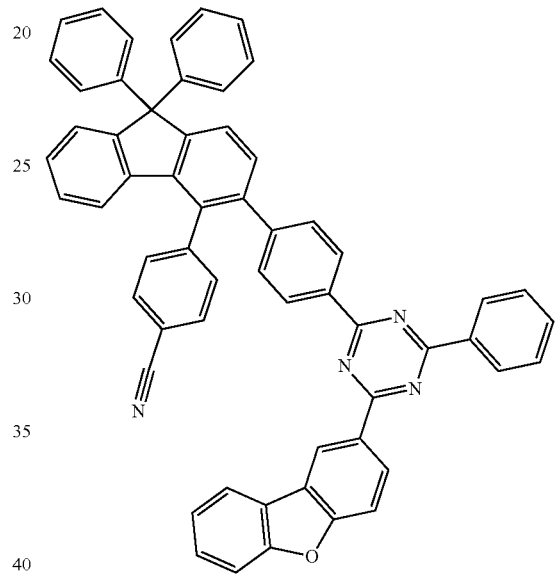

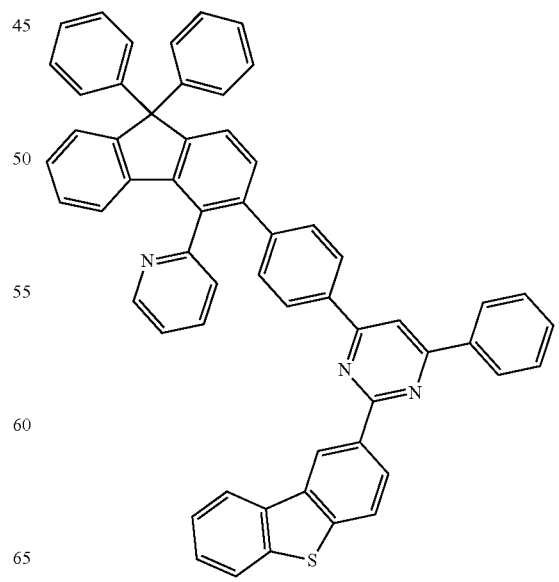

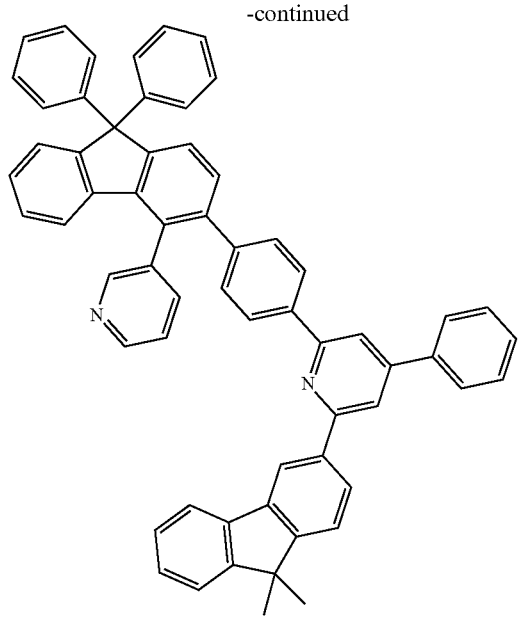
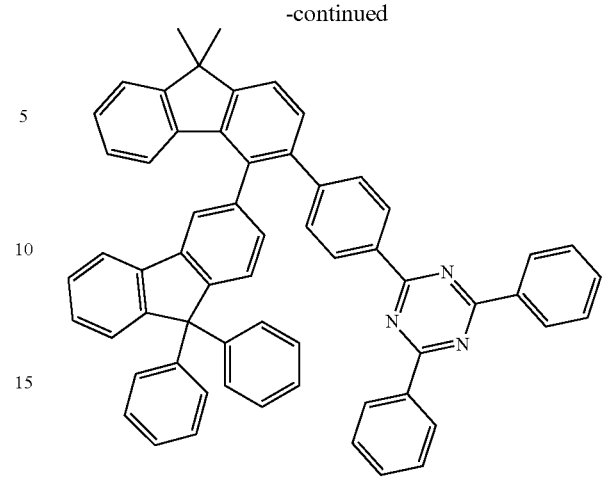
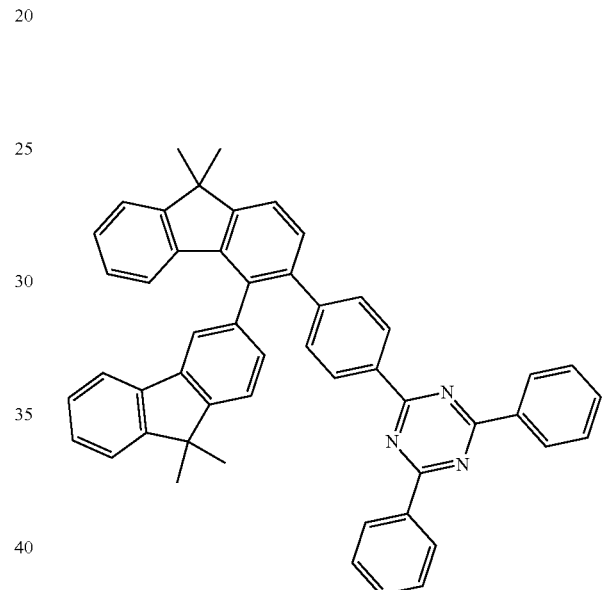
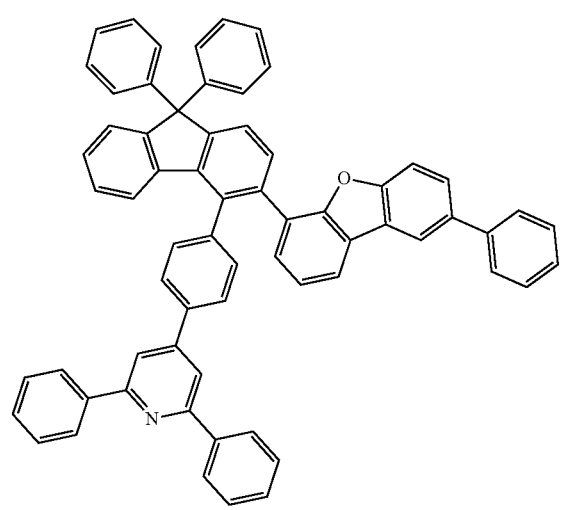
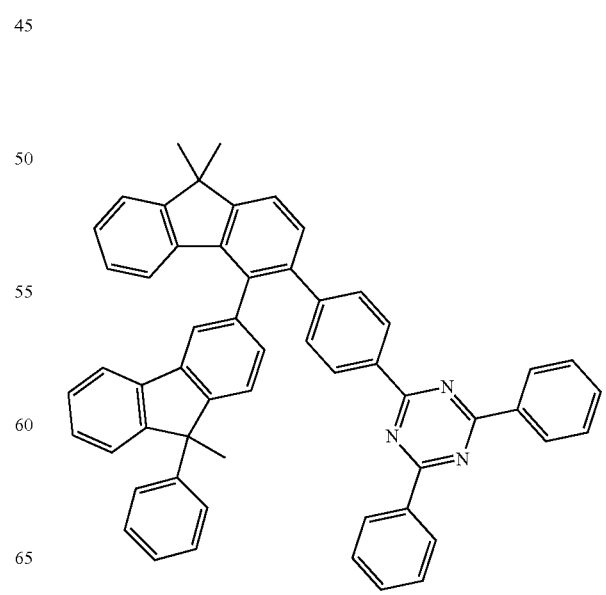

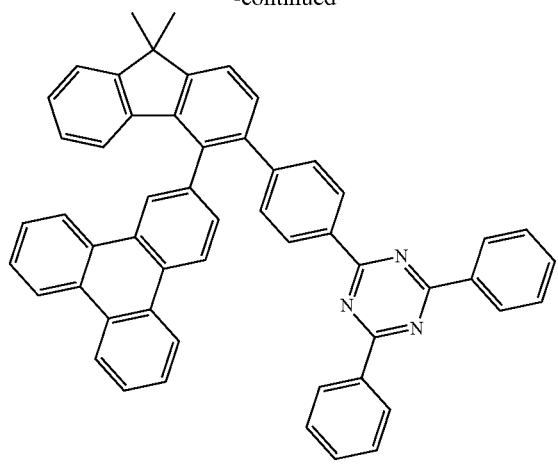
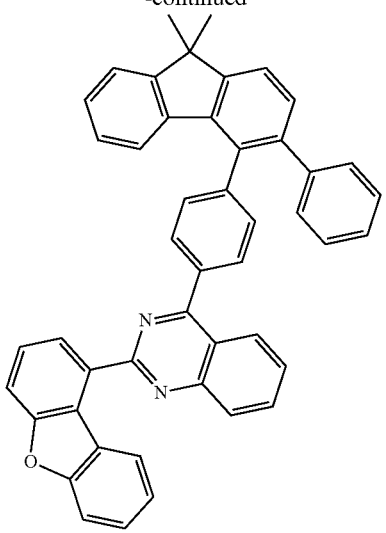
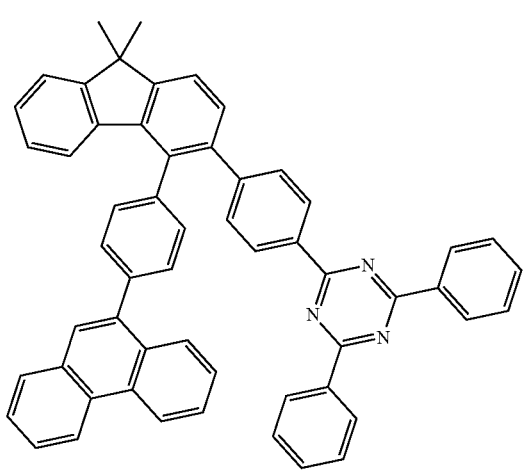
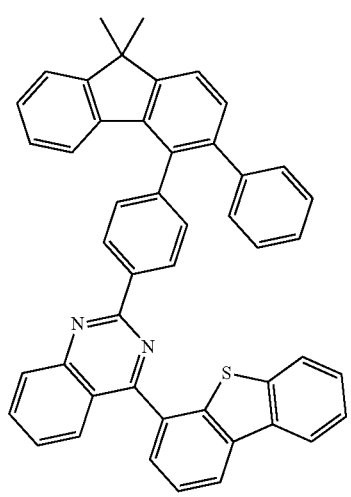
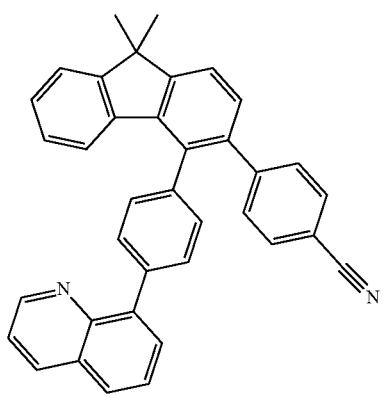
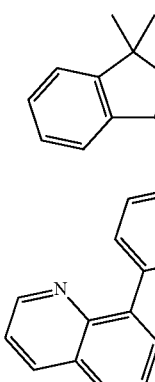

37
-continued
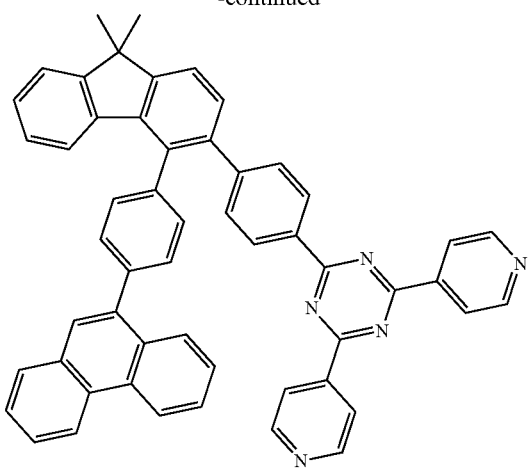
38
-continued
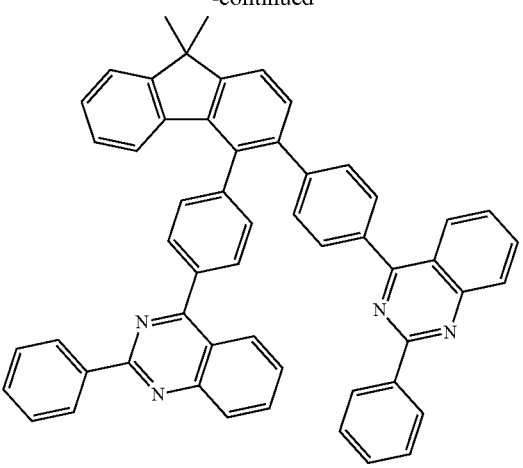
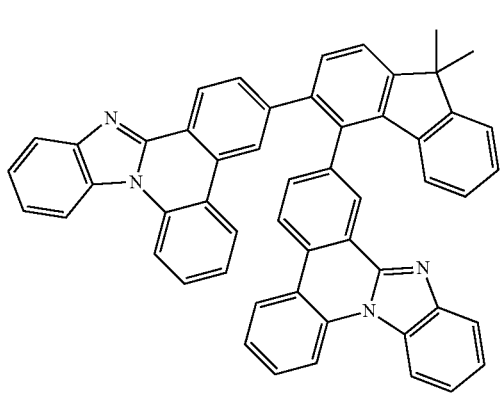
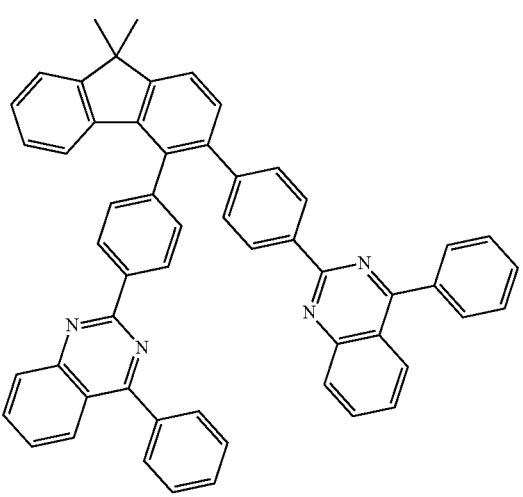
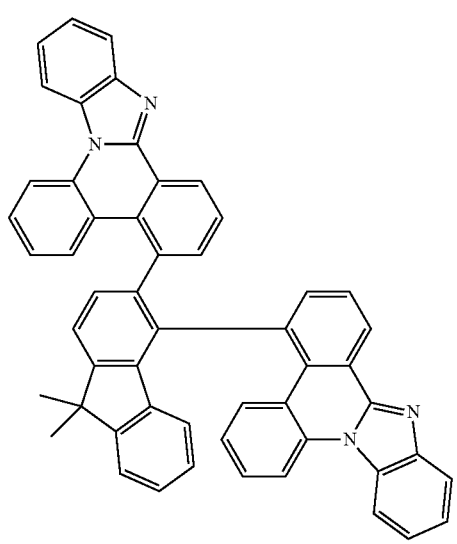
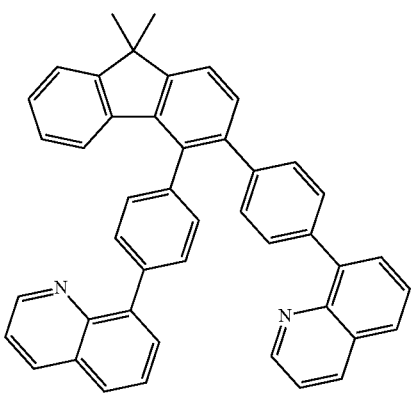

-continued
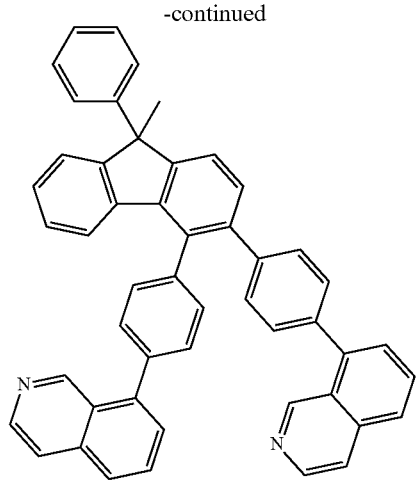
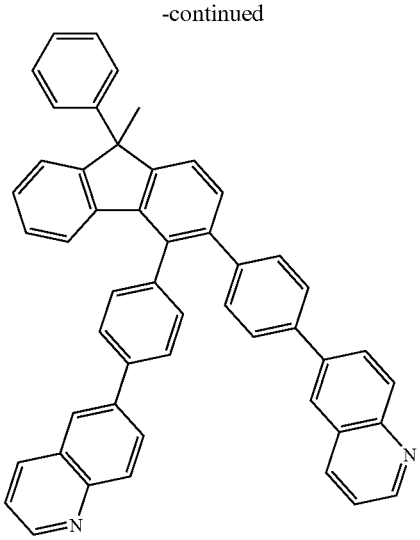
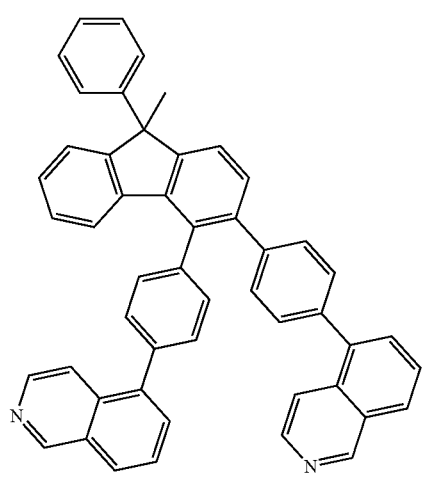
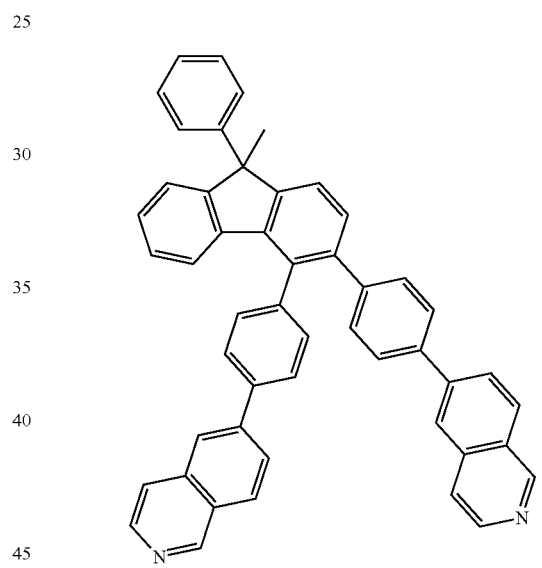
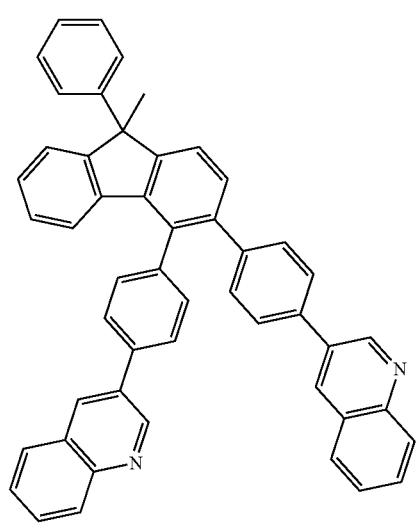
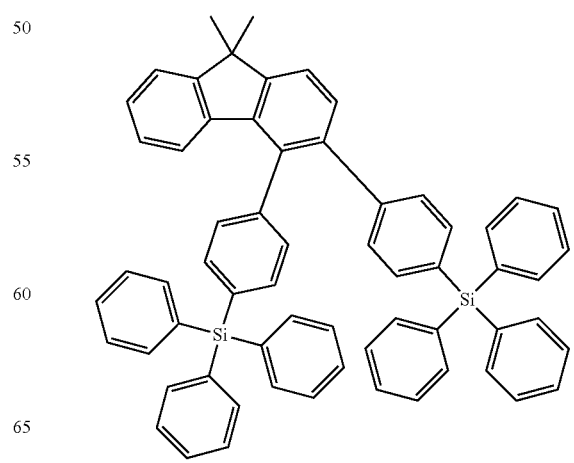

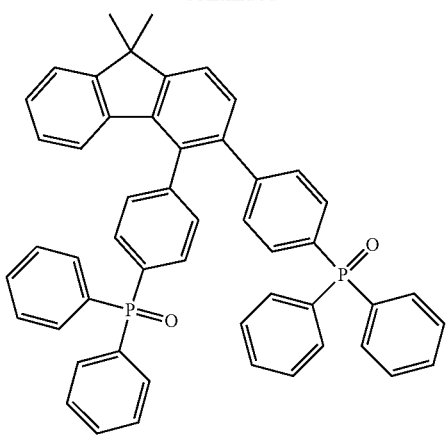
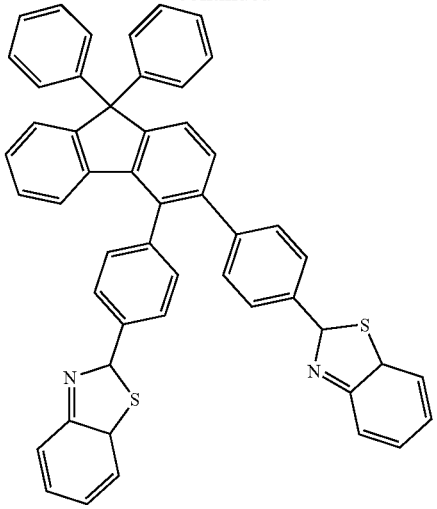
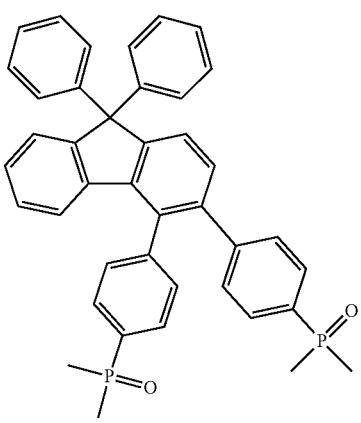
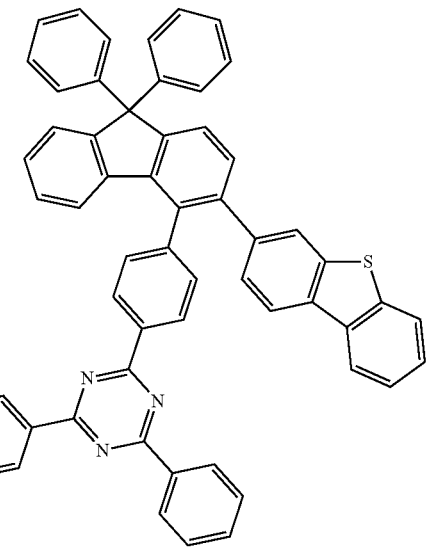
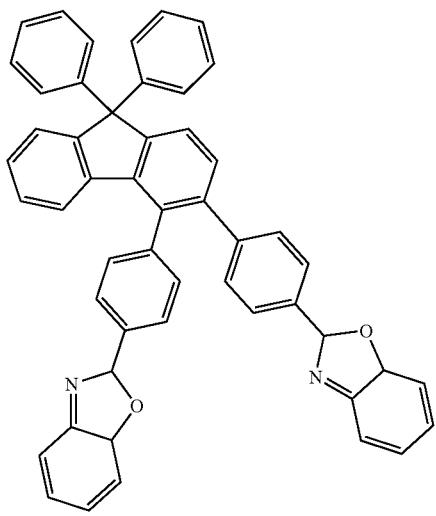
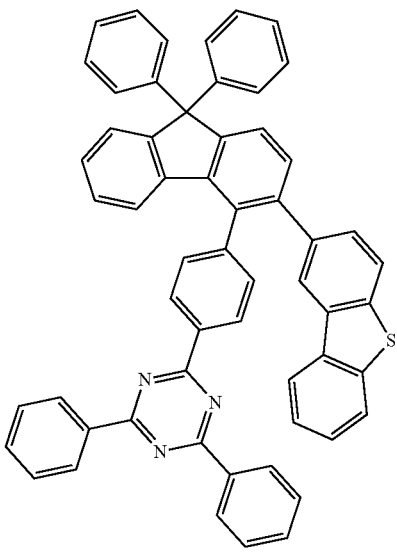

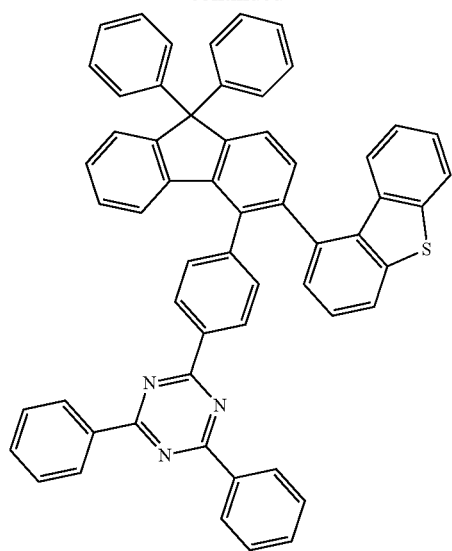
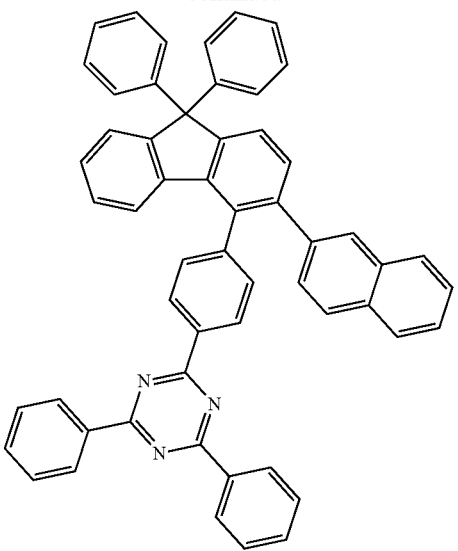
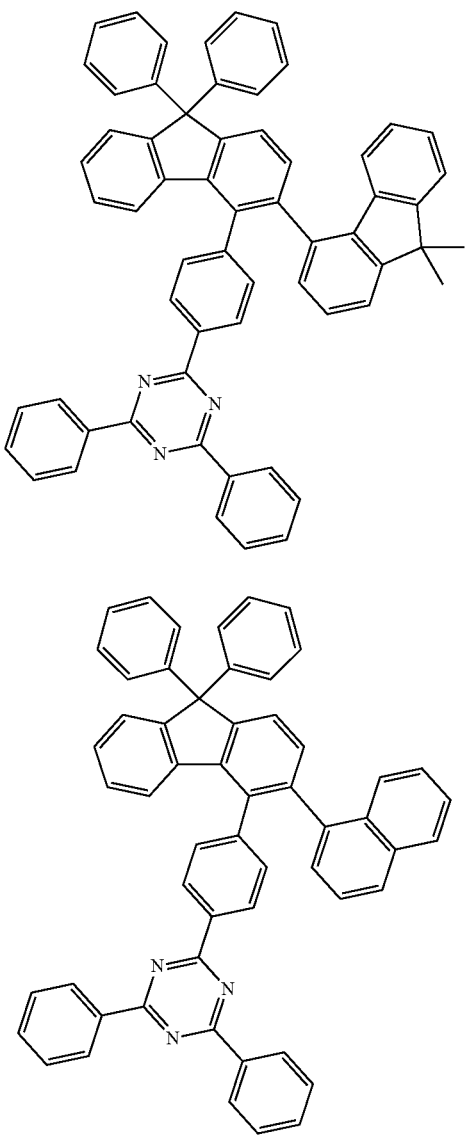
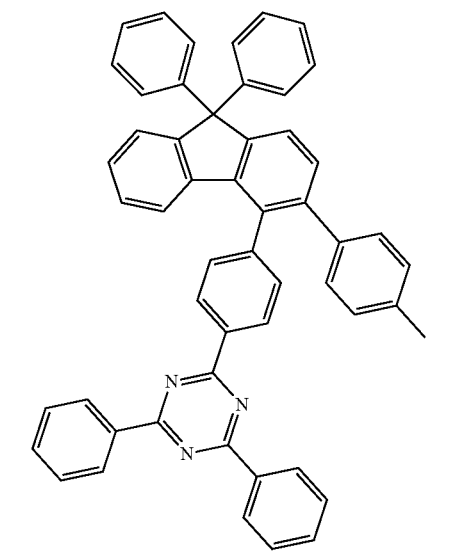
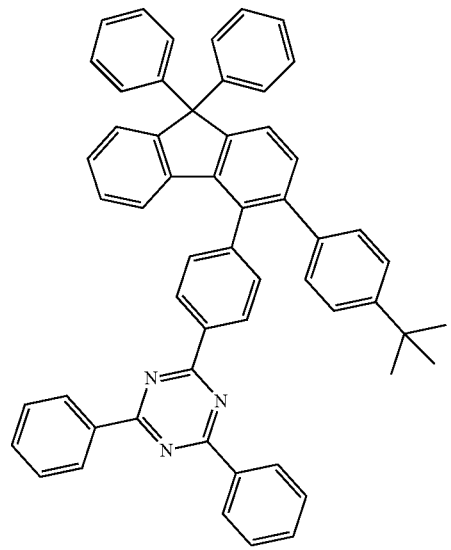

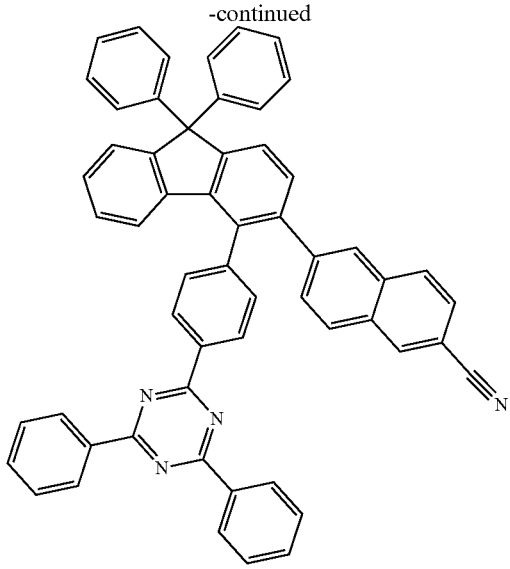
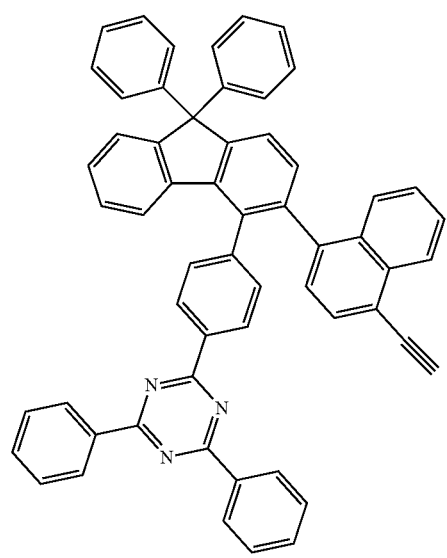
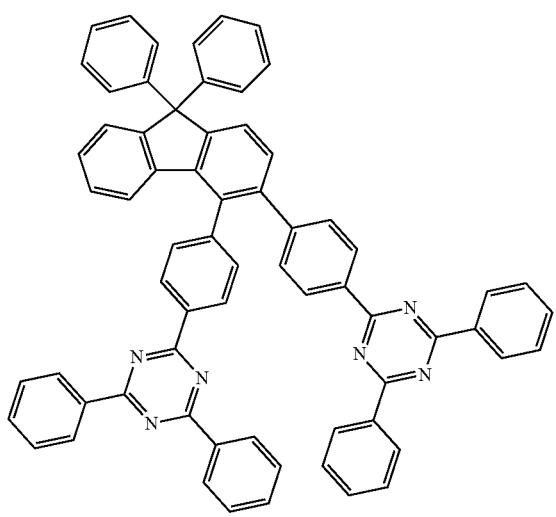
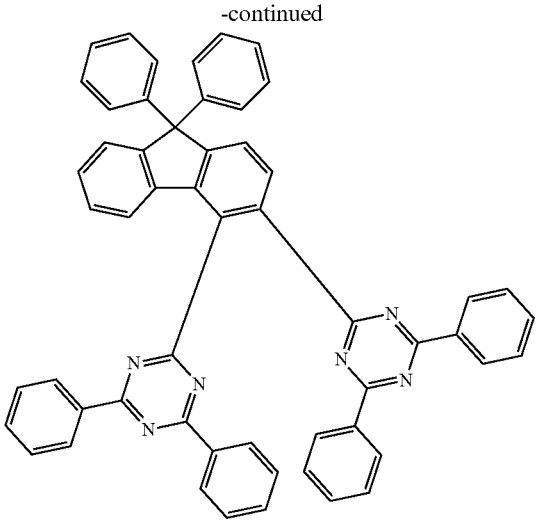
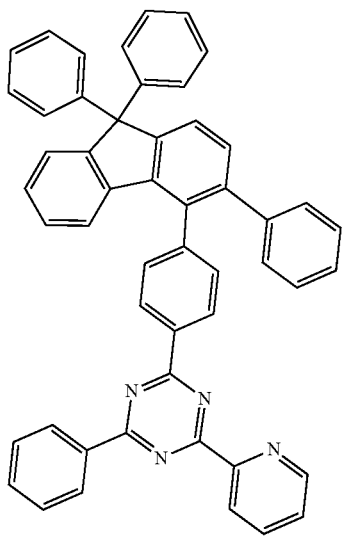
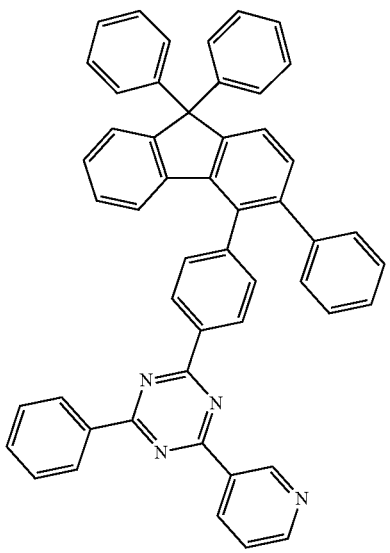

47
-continued
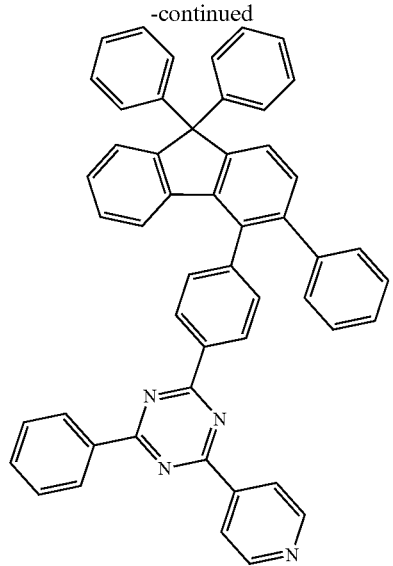
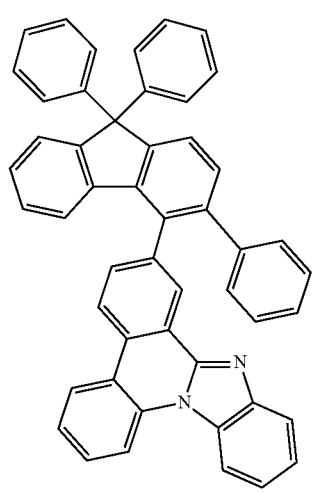
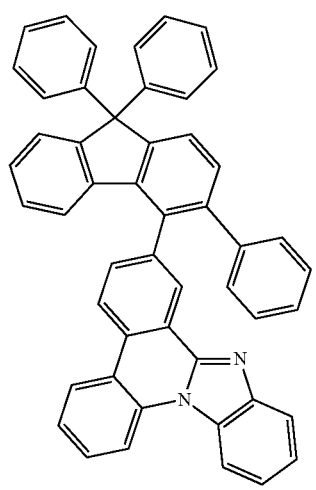
48
-continued
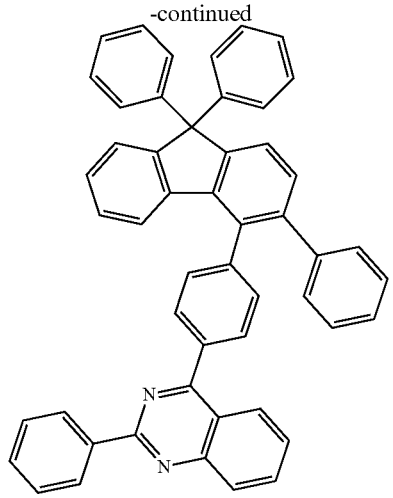
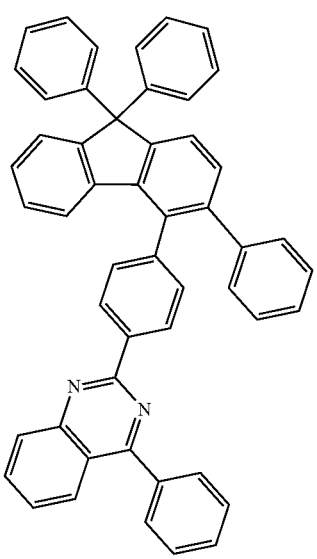
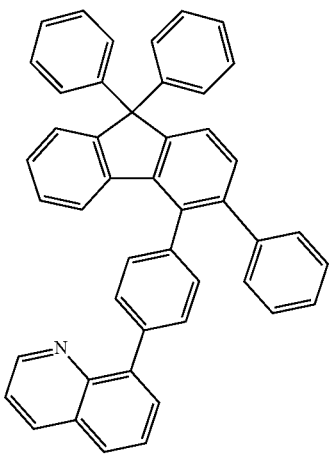

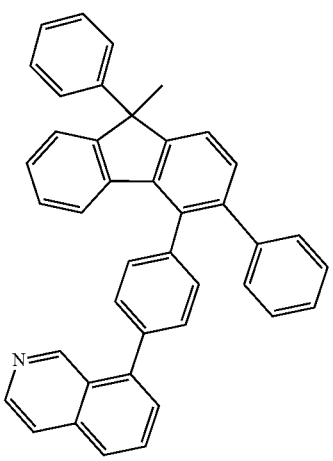
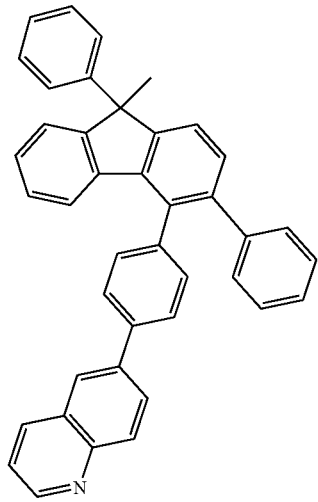
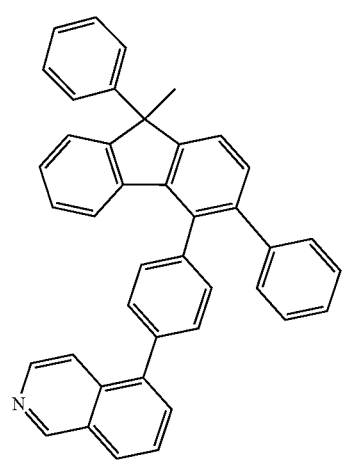
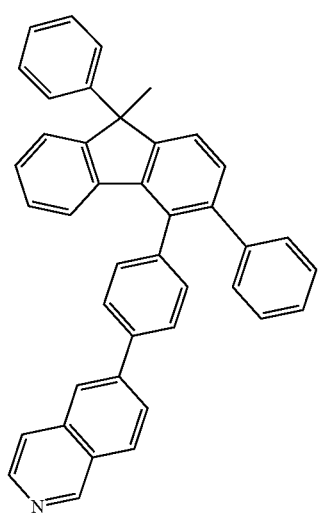
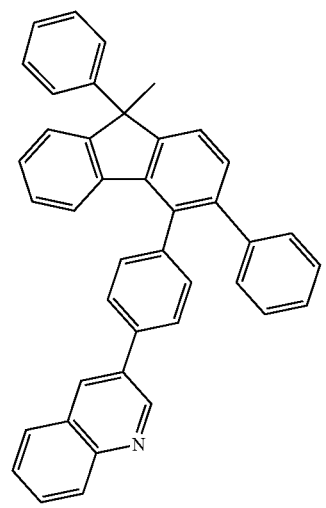
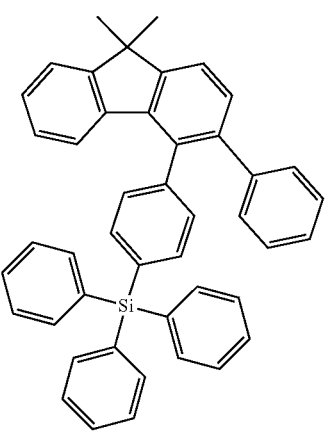

51
-continued
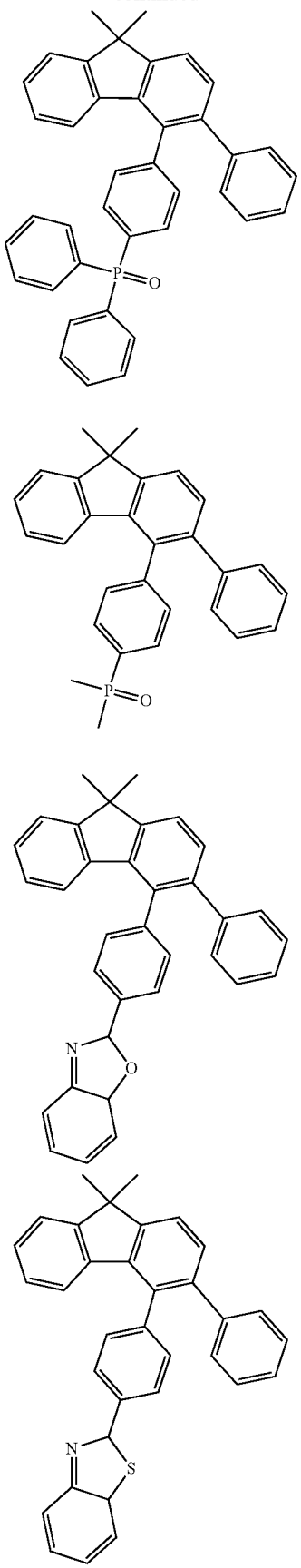
52
-continued
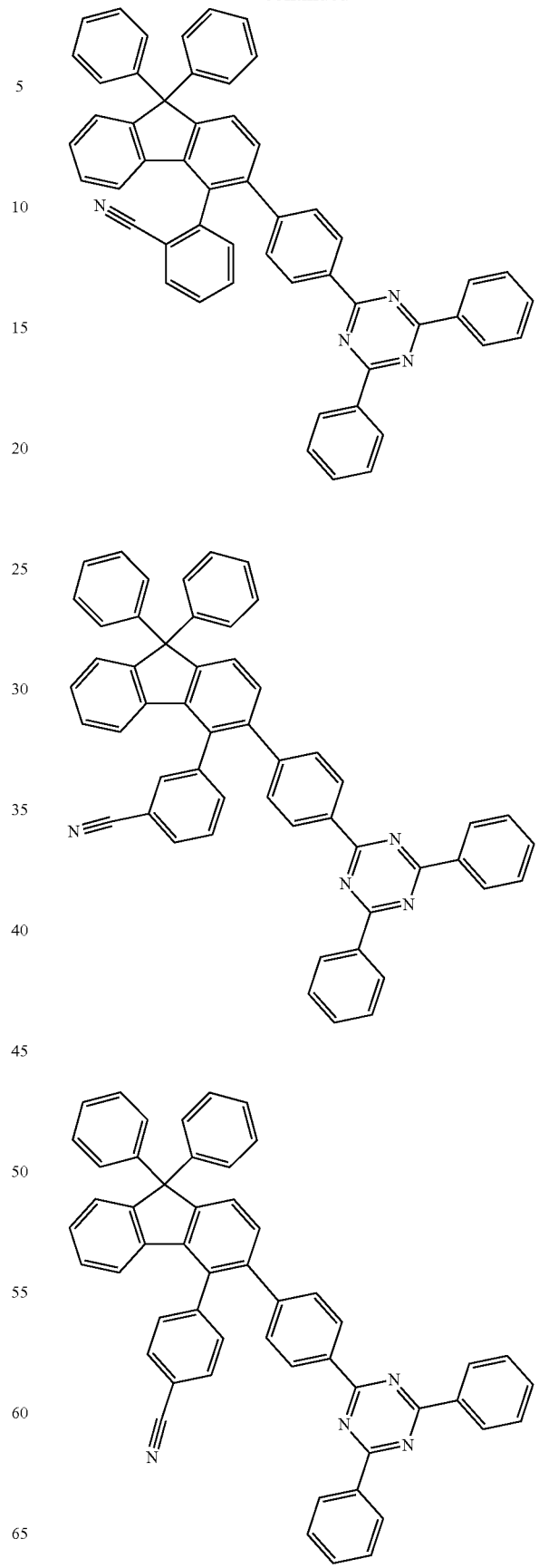

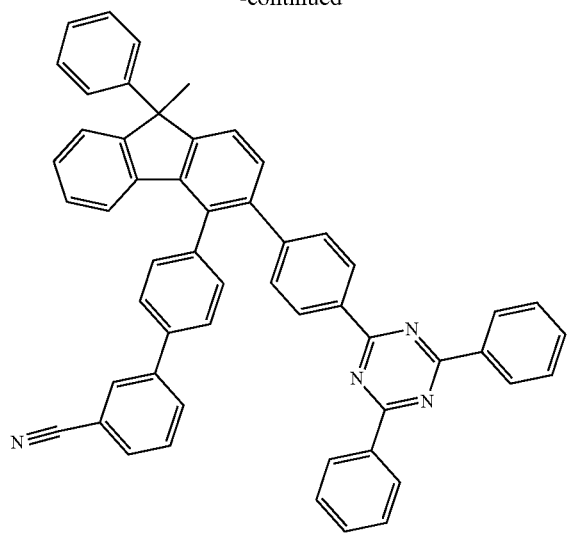
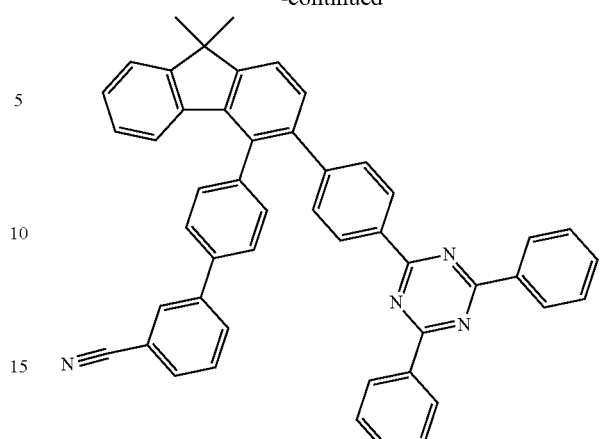
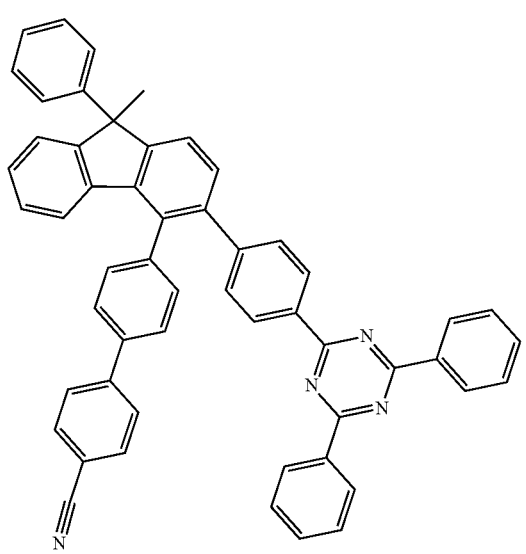
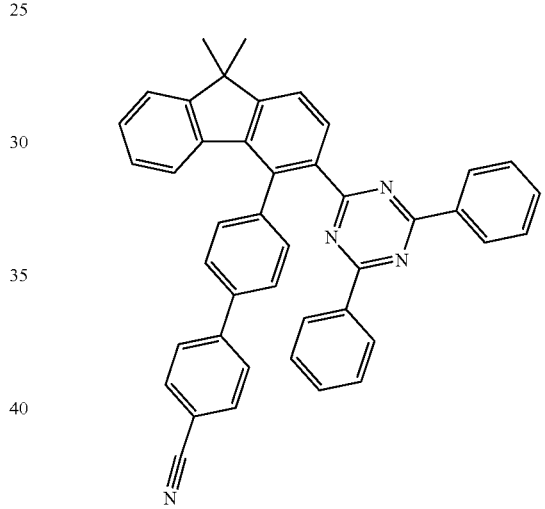
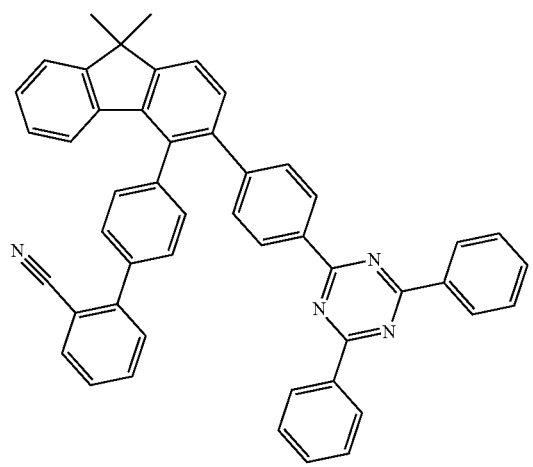
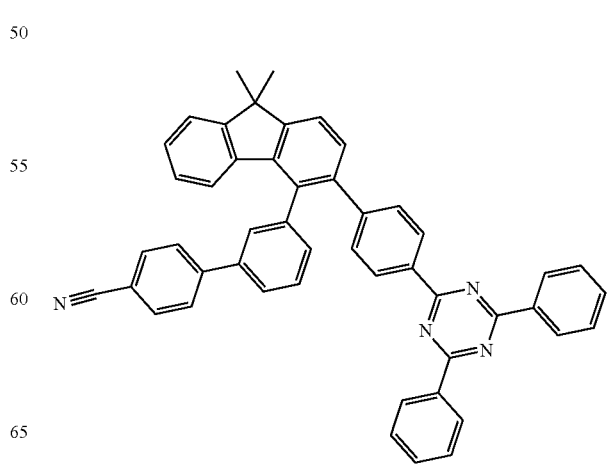

55
-continued
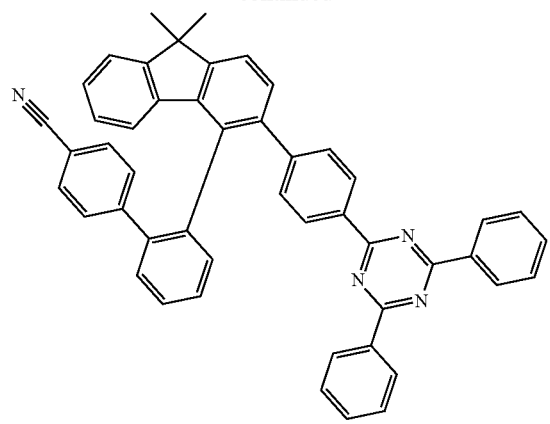
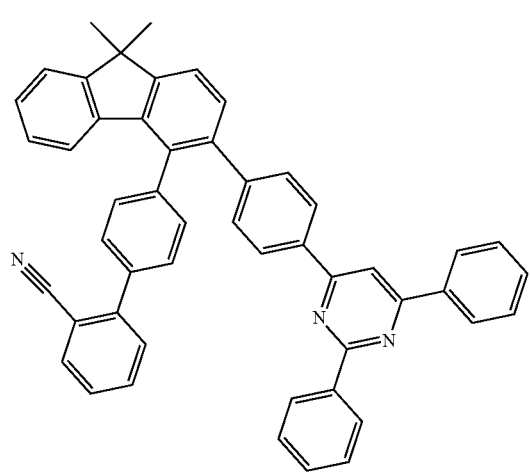
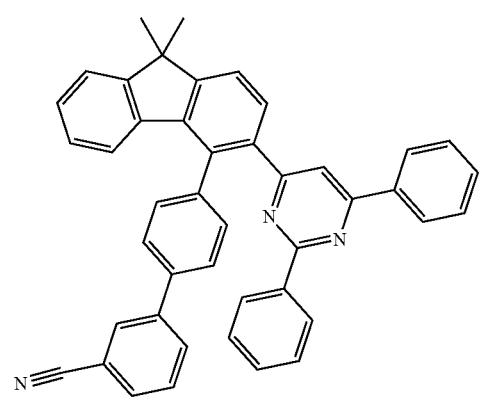
56
-continued
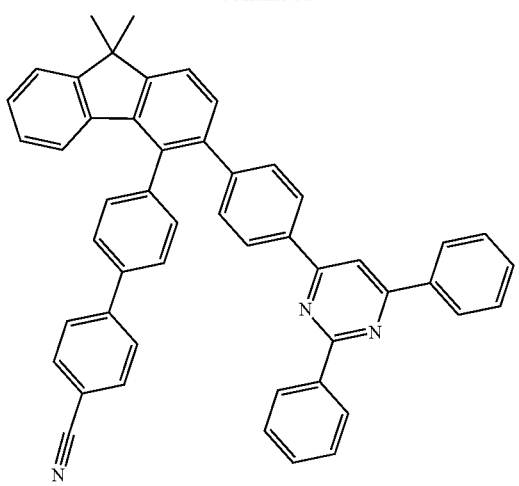
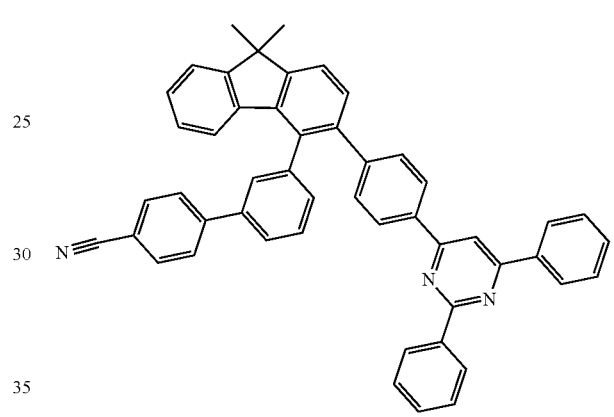
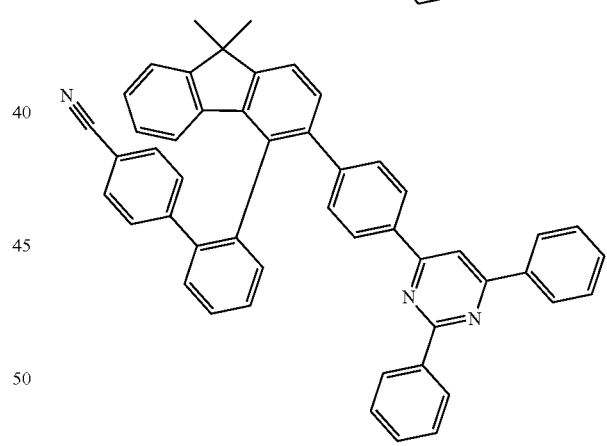
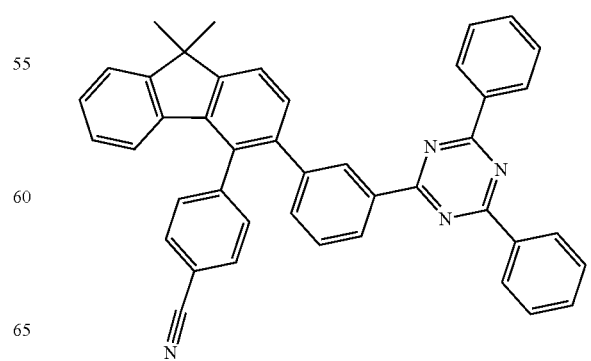

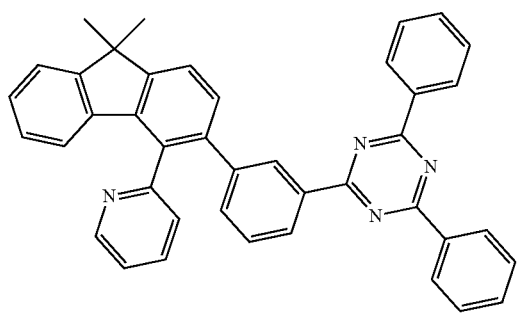
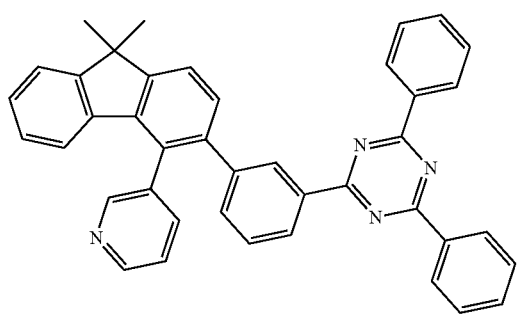
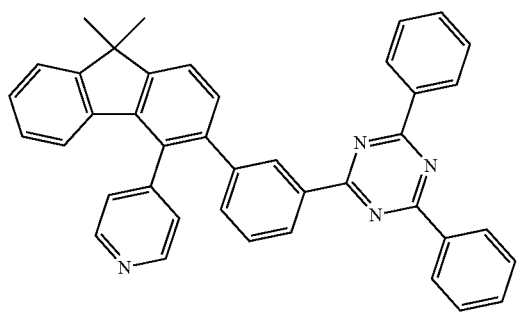
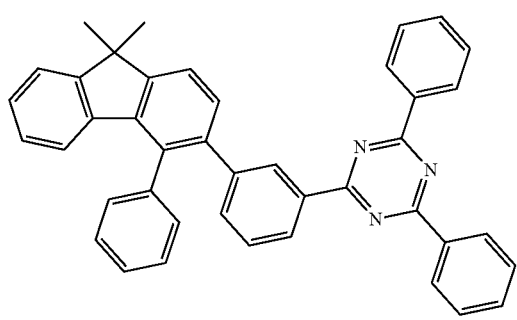
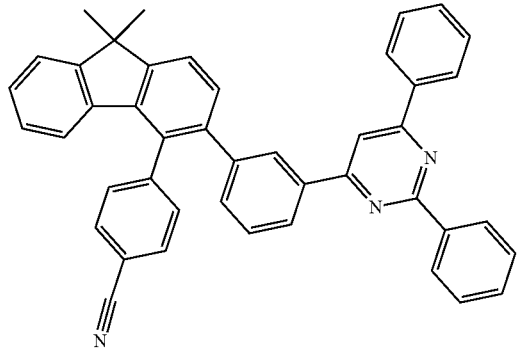
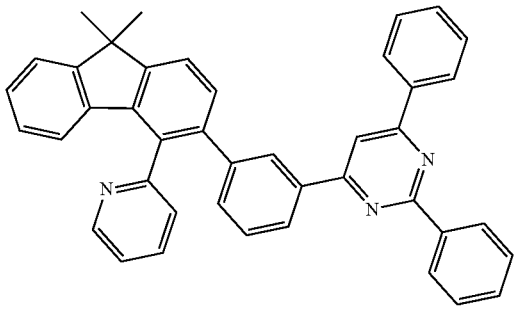
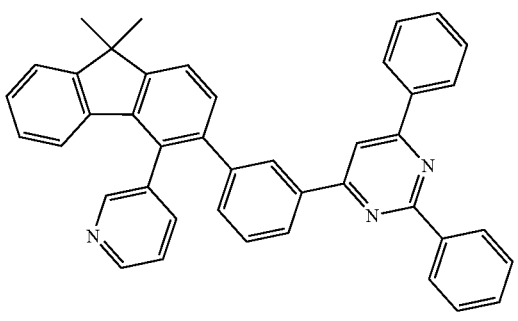
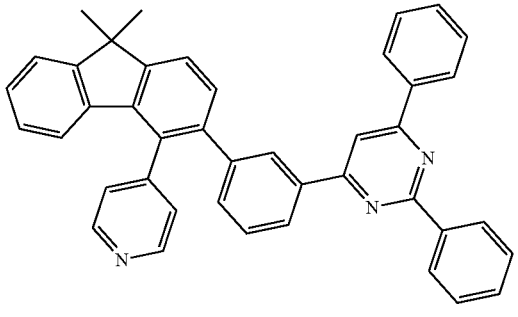
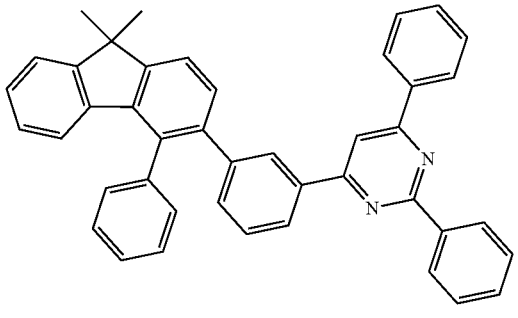
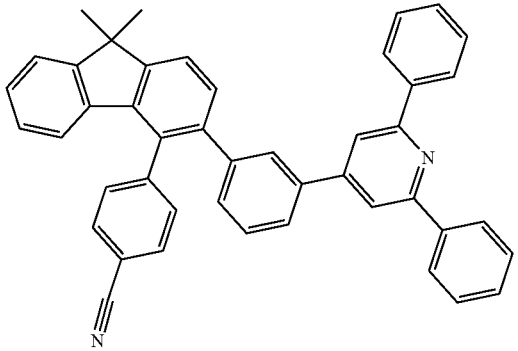

59
-continued
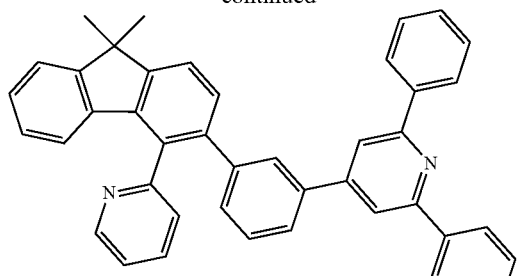
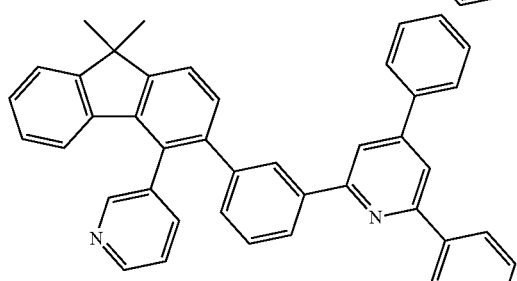
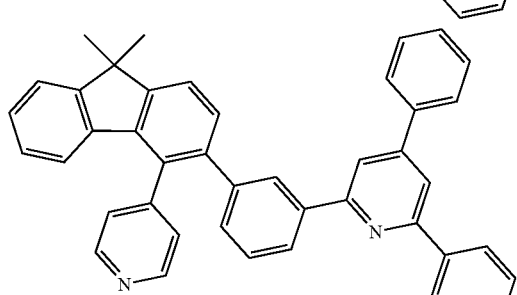
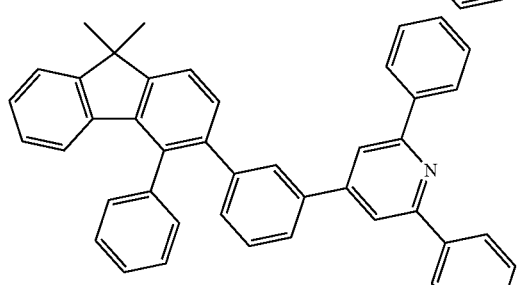
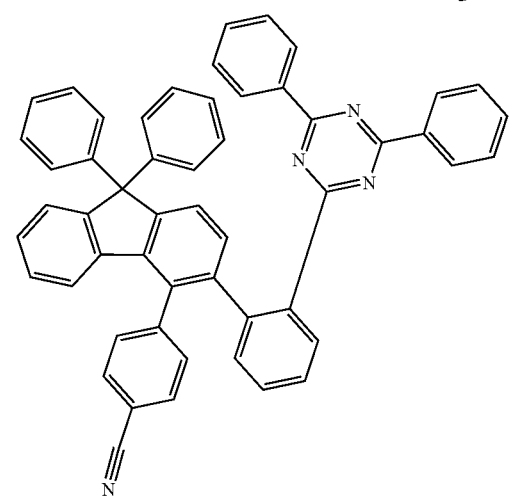
60
-continued
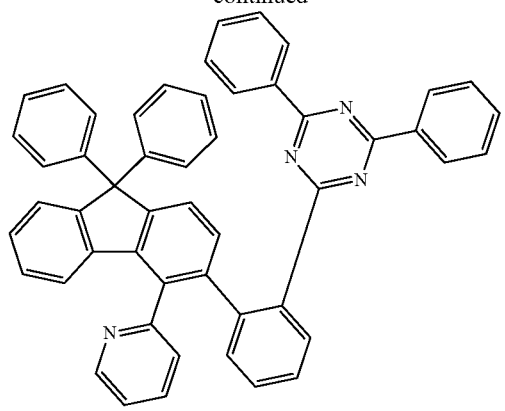
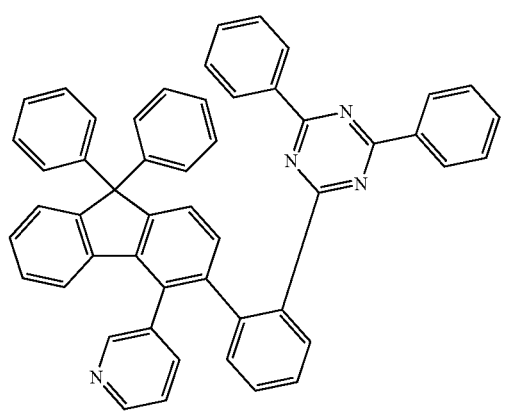
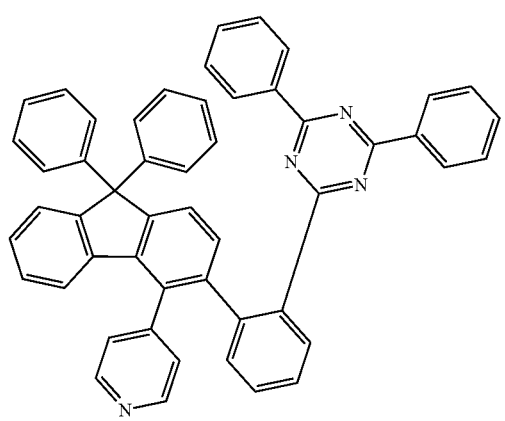
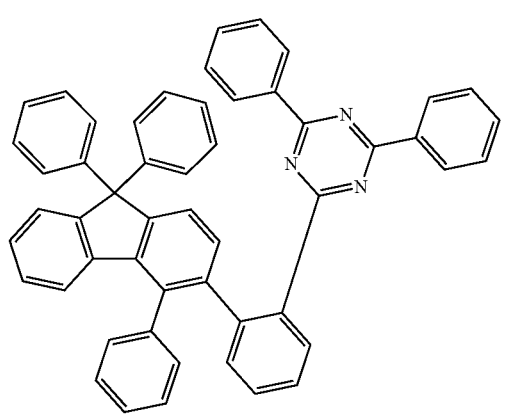

61
-continued
62
-continued
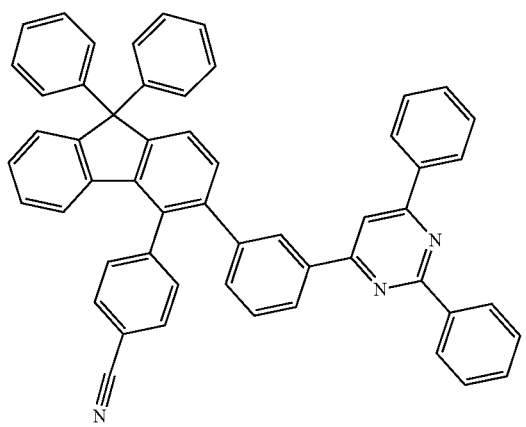
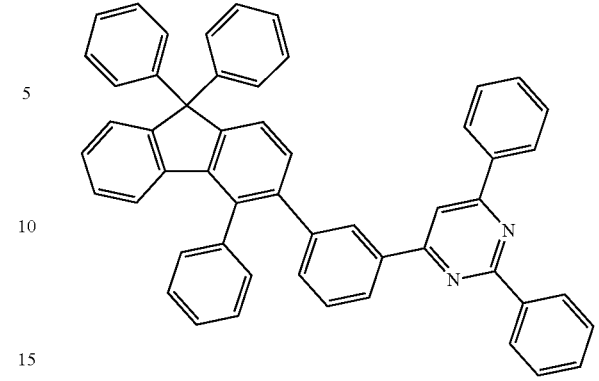
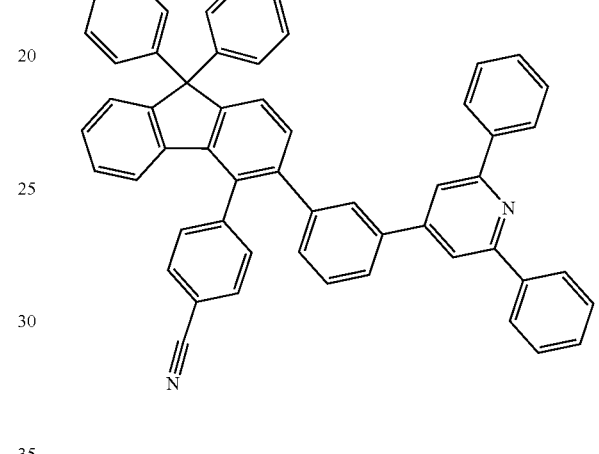
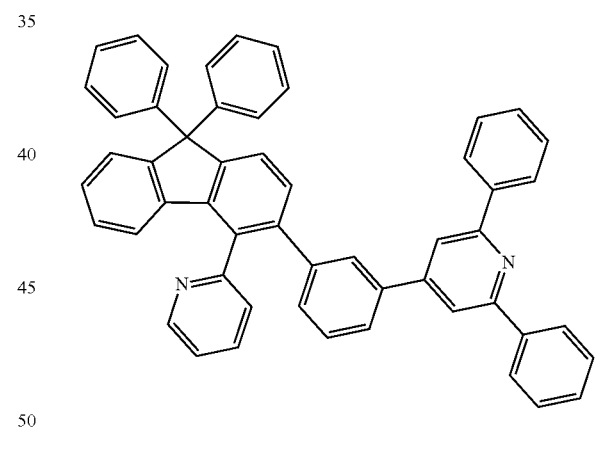
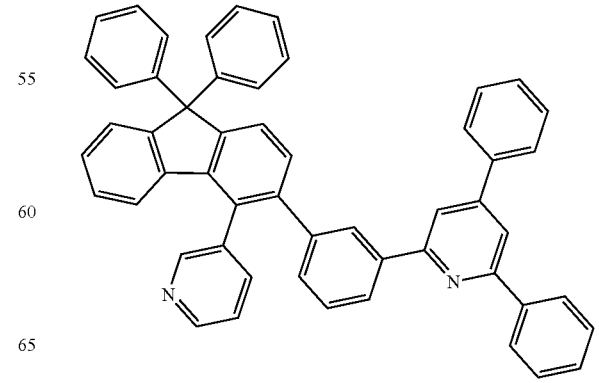

-continued
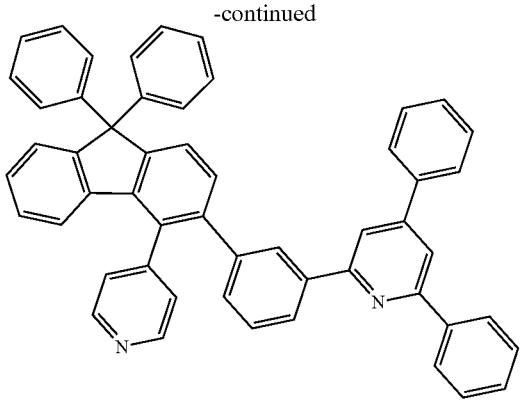
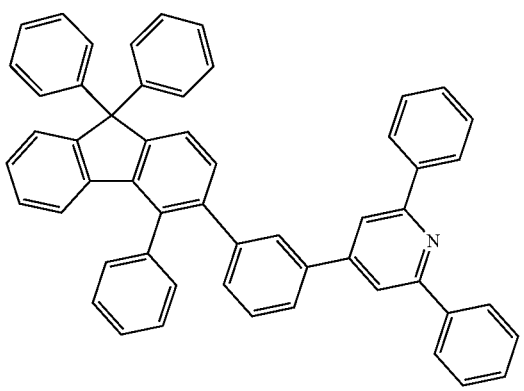
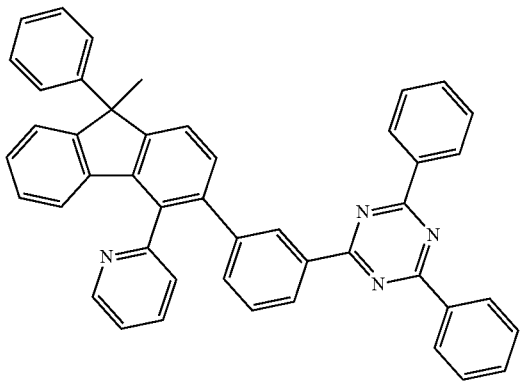
-continued
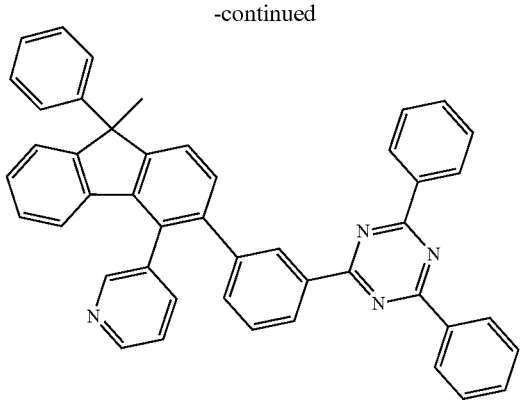
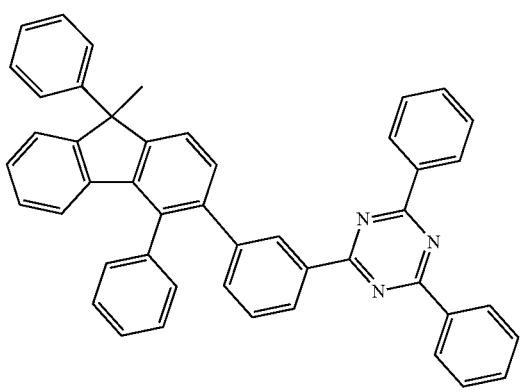
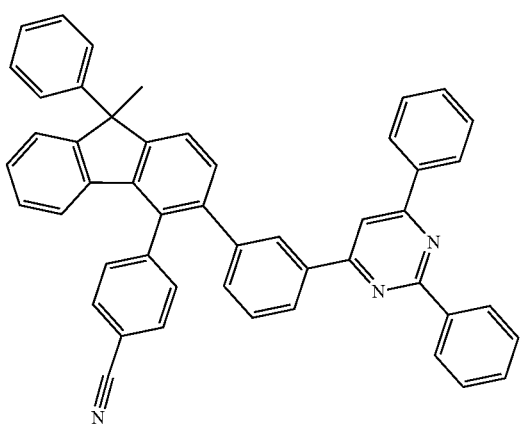

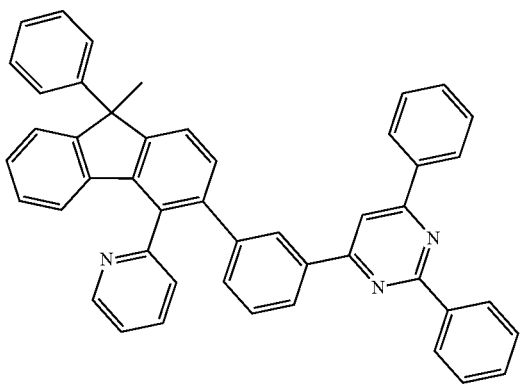
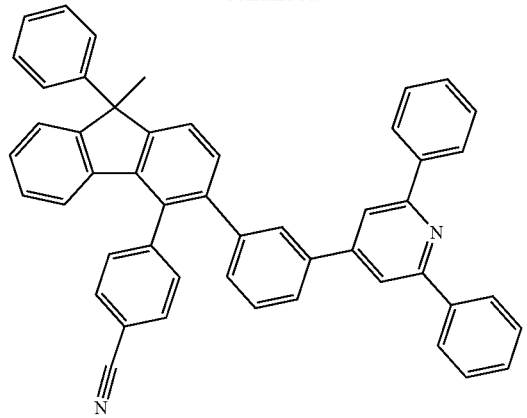
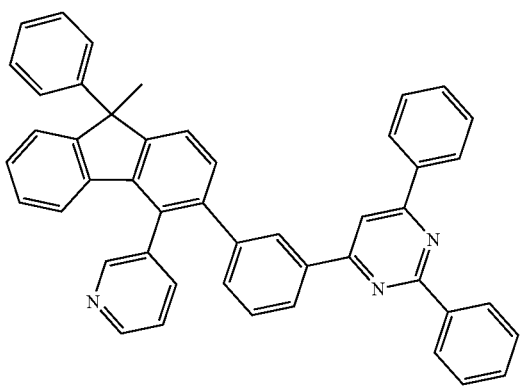
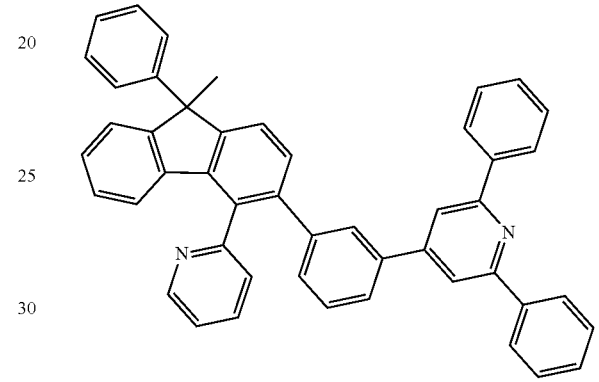
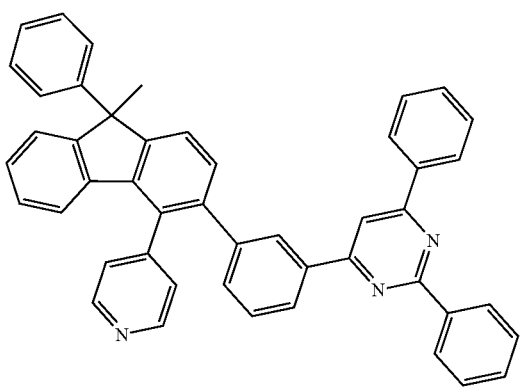
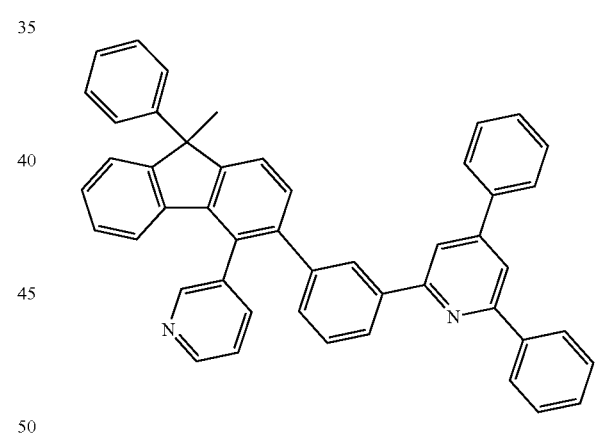
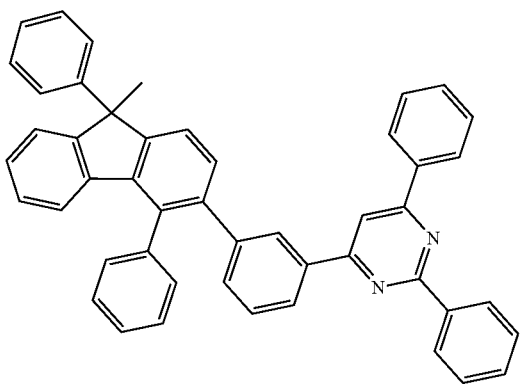
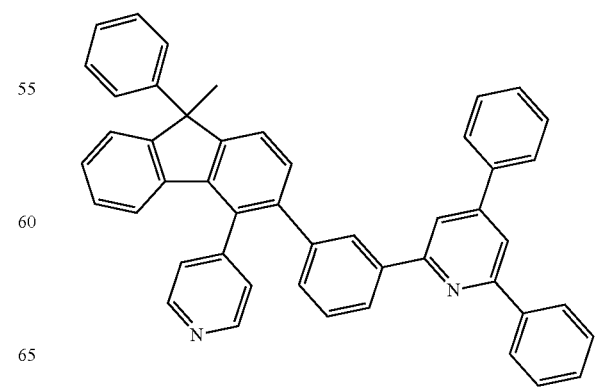

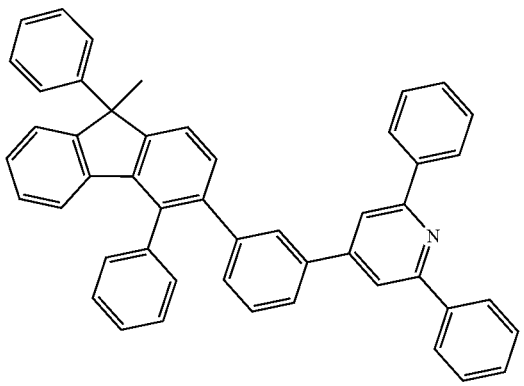

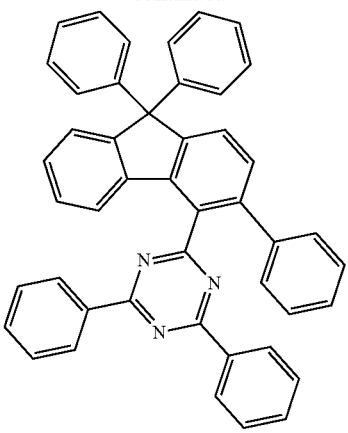

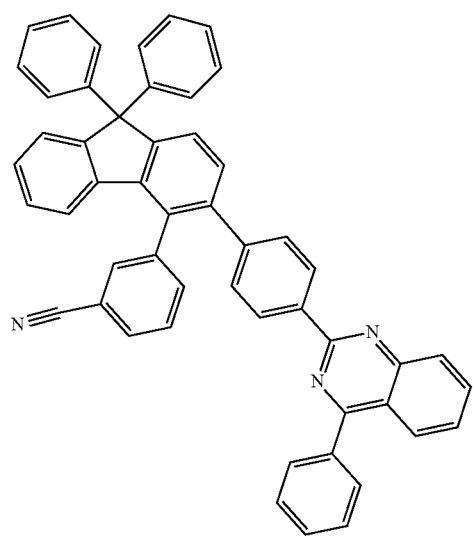

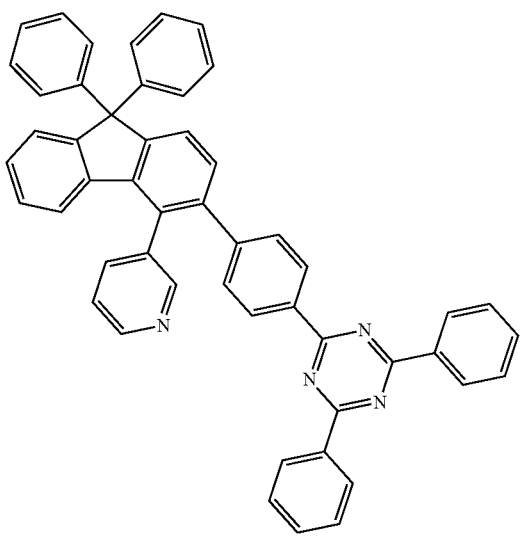

According to one embodiment of the present specification, the compound of Chemical Formula 1 can be prepared as in the following reaction formulae, however, the reaction is not limited thereto. In the following reaction formulae, types and the number of substituents can be determined by those skilled in the art properly selecting known starting materials. As reaction types and reaction conditions, those known in the art can be used.

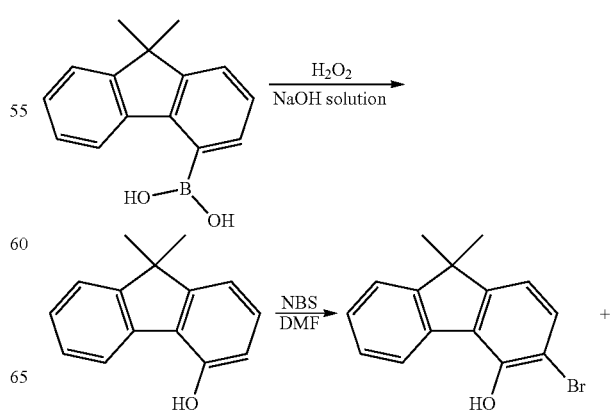

Reaction Formula 1

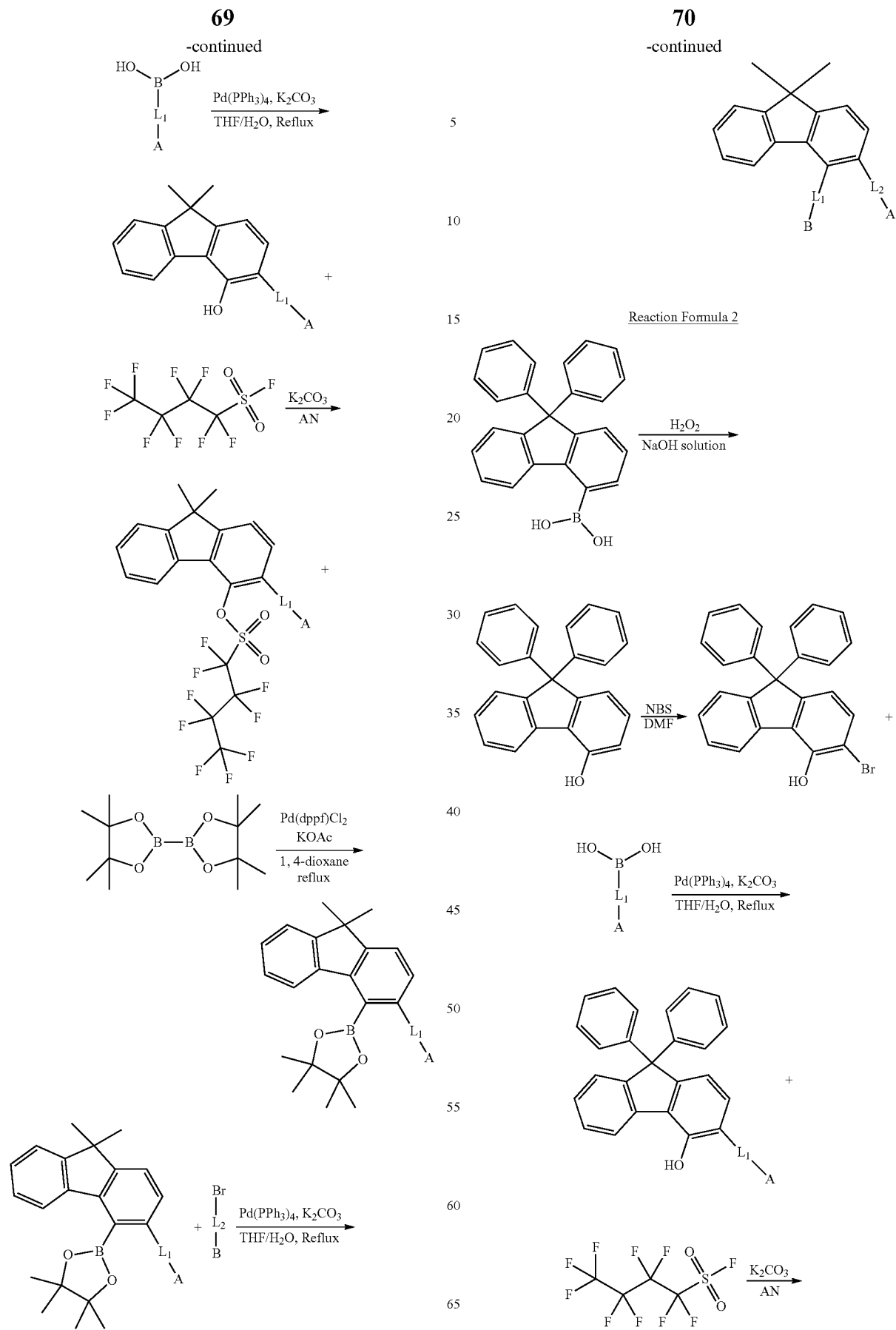

71
-continued
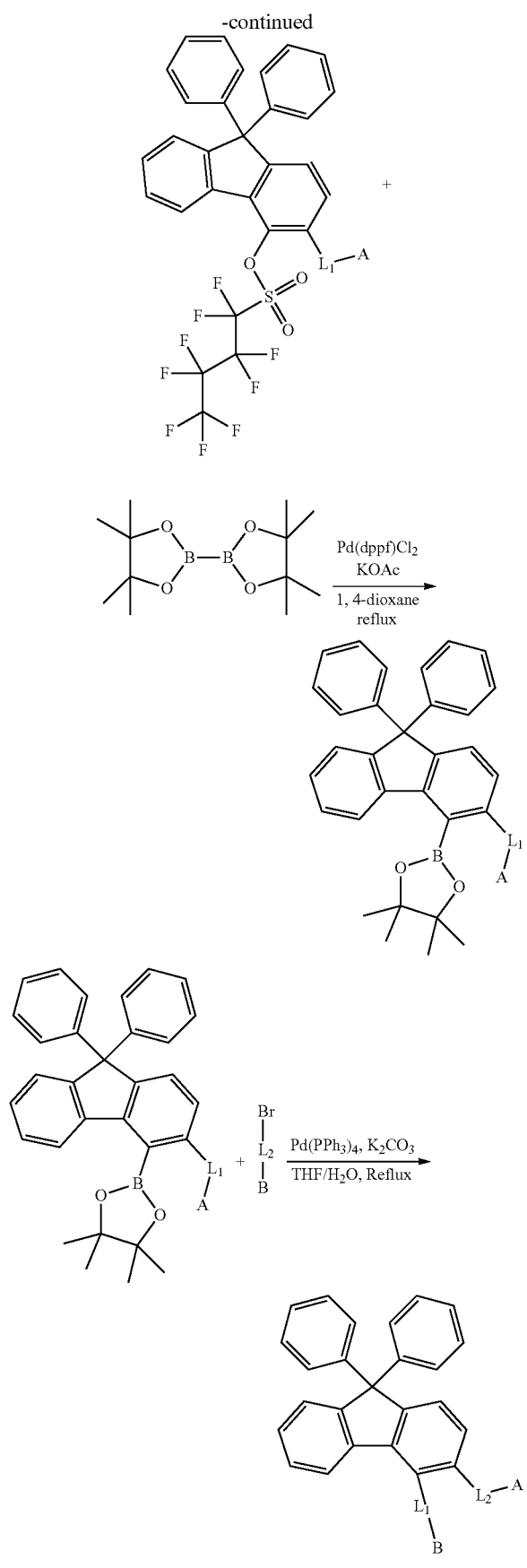
72
Reaction Formula 3
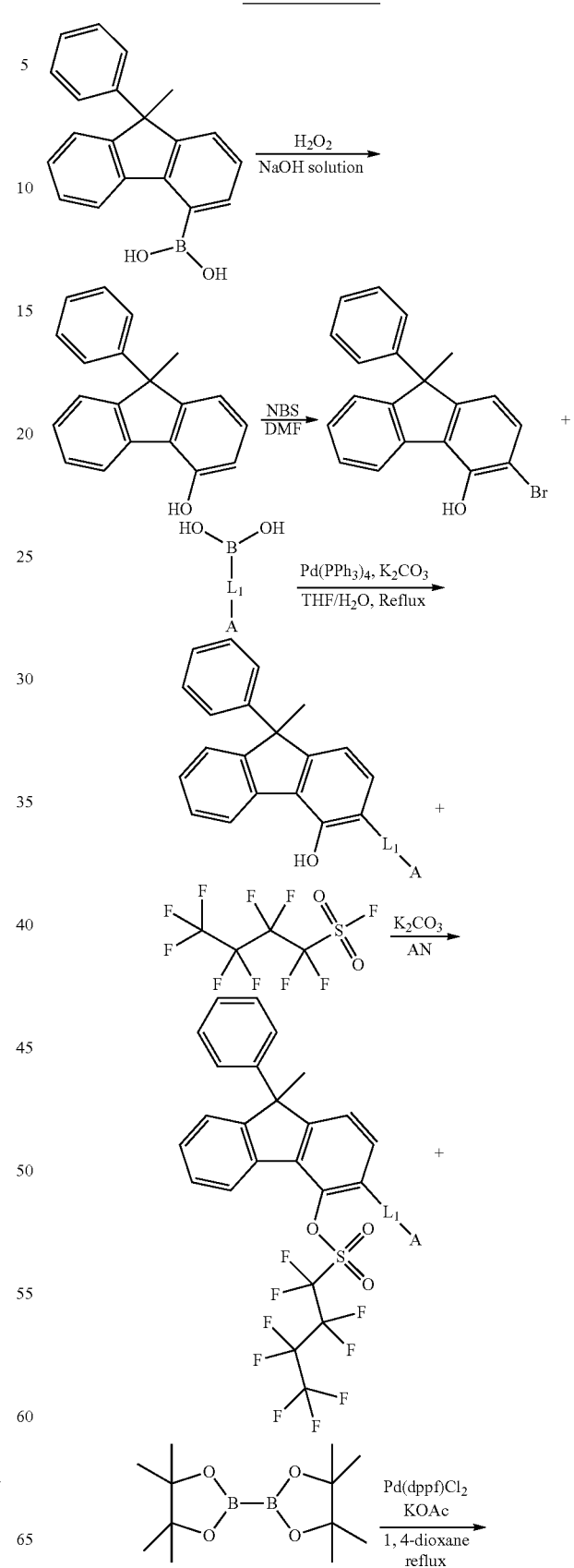

-continued

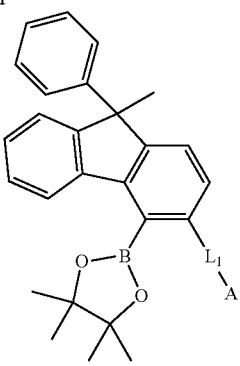

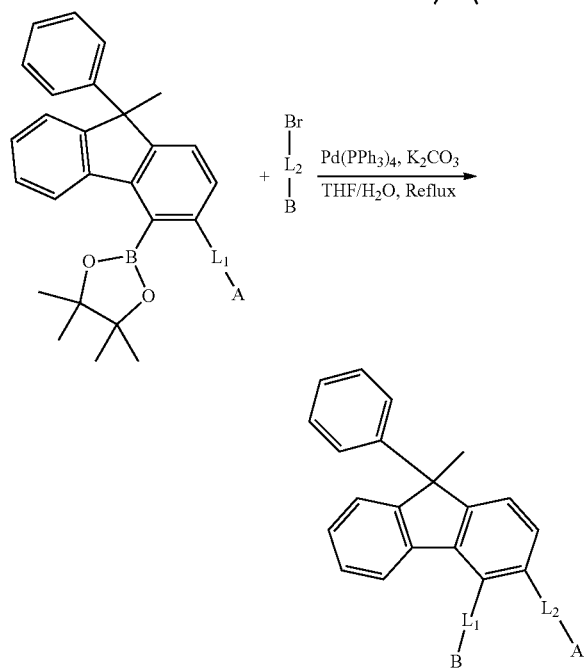

In the reaction formulae, L1, L2, A and B have the same definitions as in Chemical Formula 1.

Reaction Formulae 1 to 3 each illustrate a case in which R3 to R8 are hydrogen, however, R3 to R8 can be substituted with substituents other than hydrogen as necessary.

One embodiment of the present specification provides an organic light emitting device including a first electrode, a second electrode provided opposite to the first electrode, and one or more organic material layers provided between the first electrode and the second electrode, wherein one or more layers of the organic material layers include the above-described compound.

According to one embodiment of the present specification, the organic material layer of the organic light emitting device of the present specification can be famed in a single layer structure, but can also be formed in a multilayer structure in which two or more organic material layers are laminated. For example, the organic light emitting device of the present disclosure can have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can include a smaller or larger number of organic material layers.

For example, the organic light emitting device of the present specification can have structures as illustrated in FIG. 1 and FIG. 2, however, the structure is not limited thereto.

FIG. 1 illustrates a structure of the organic light emitting device in which a first electrode (2), a light emitting layer (3) and a second electrode (4) are consecutively laminated on a substrate (1). FIG. 1 is an exemplary structure of an organic light emitting device according to one embodiment of the present specification, and other organic material layers can be further included. In such a structure, the compound of Chemical Formula 1 can be included in the light emitting layer.

FIG. 2 illustrates a structure of the organic light emitting device in which a first electrode (2), a hole injection layer (5), a hole transfer layer (6), a light emitting layer (3), an electron transfer layer (7) and a second electrode (4) are consecutively laminated on a substrate (1). FIG. 2 is an exemplary structure of an organic light emitting device according to an embodiment of the present specification, and other organic material layers can be further included. Herein, the compound of Chemical Formula 1 can be included in the hole injection layer, the hole transfer layer, the light emitting layer, or the electron injection and transfer layer. The compound of Chemical Formula 1 can be preferably included in the electron injection and transfer layer.

FIG. 3 illustrates a structure of the organic light emitting device in which a first electrode (2), a hole injection layer (5), a hole transfer layer (6), an electron blocking layer (8), a light emitting layer (3), an electron transfer layer (7) and a second electrode (4) are consecutively laminated on a substrate (1). FIG. 3 is an exemplary structure of an organic light emitting device according to an embodiment of the present specification, and other organic material layers can be further included. Herein, the compound of Chemical Formula 1 can be included in the hole injection layer, the hole transfer layer, the electron blocking layer, the light emitting layer or the electron transfer layer. The compound of Chemical Formula 1 can be preferably included in the electron injection and transfer layer.

According to one embodiment of the present specification, the organic material layer includes a hole injection layer, a hole transfer layer or an electron blocking layer, and the hole injection layer, the hole transfer layer or the electron blocking layer includes the compound of Chemical Formula 1.

According to one embodiment of the present specification, the organic material layer includes a light emitting layer, and the light emitting layer includes the compound of Chemical Formula 1.

According to one embodiment of the present specification, the organic material layer includes a light emitting layer, and the light emitting layer includes the compound of Chemical Formula 1 as a host of the light emitting layer.

According to one embodiment of the present specification, the organic material layer includes a hole blocking layer, an electron transfer layer, an electron injection layer, or an electron injection and transfer layer, and the hole blocking layer, the electron transfer layer, the electron injection layer, or the electron injection and transfer layer includes the compound of Chemical Formula 1.

According to one embodiment of the present specification, the electron transfer layer, the electron injection layer, or the electron injection and transfer layer including the compound of Chemical Formula 1 can further include an n-type dopant. As the n-type dopant, those known in the art can be used, and for example, alkali metals, alkaline earth metals, alkali metal compounds, alkaline earth metal compounds, alkali metal complexes, alkaline earth metal complexes or the like can be used. As the metal compound, oxides, halides and the like can be used, and the complex can further include an organic ligand. For example, LiQ and the like can be used. The n-type dopant can be included in the electron transfer layer, the electron injection layer, or the electron injection and transfer layer in 1% by weight to 75% by weight and preferably in 30% by weight to 55% by weight.

According to one embodiment of the present specification, the organic material layer can further include one or more layers selected from the group consisting of a hole injection layer, a hole transfer layer, an electron blocking layer, a hole blocking layer, an electron transfer layer and an electron injection layer.

The organic light emitting device of the present specification can be manufactured using materials and methods known in the art, except that one or more layers of the organic material layers include the compound of the present specification, that is, the compound of Chemical Formula 1.

When the organic light emitting device includes a plurality of organic material layers, the organic material layers can be formed with the same material or with different materials.

For example, the organic light emitting device of the present specification can be manufactured by consecutively laminating a first electrode, an organic material layer and a second electrode on a substrate. Herein, the organic light emitting device can be manufactured by forming the first electrode on the substrate by depositing a metal, a metal oxide having conductivity, or an alloy thereof using a physical vapor deposition (PVD) method such as a sputtering method or an e-beam evaporation method, forming the organic material layer including a hole injection layer, a hole transfer layer, a light emitting layer and an electron transfer layer thereon, and then depositing a material usable as the second electrode thereon. In addition to this method, the organic light emitting device can be manufactured by consecutively depositing a second electrode material, an organic material layer and a first electrode material on a substrate. In addition, the compound of Chemical Formula 1 can be formed into the organic material layer using a solution coating method as well as a vacuum deposition method when manufacturing the organic light emitting device. Herein, the solution coating method means spin coating, dip coating, doctor blading, ink jet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; and multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzoquinoline-metal compounds; benzoxazole, benzothiazole and benzimidazole series compounds; poly(p-phenylenevinylene) (PPV) series polymers; spiro compounds; polyfluorene, rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group-including pyrene, anthracene, chrysene, peryflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be included, however, the metal complex is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline, complexes including Alq$_3$, organic radical compounds, hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and as the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxy-quinolinato)aluminum, tris(8-hydroxyquinolinato)gallium, bis(10-hydroxybenzo[h]quinolinato)beryllium, bis(10-hydroxybenzo[h]-quinolinato)zinc, bis(2-methyl-8-quinolinato)-chlorogallium, bis(2-methyl-8-quinolinato) (o-cresolato)-gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification can be a top-emission type, a bottom-emission type or a dual-emission type depending on the materials used.

Hereinafter, the present specification will be described in detail with reference to examples. However, the examples according to the present specification can be modified to various other forms, and the scope of the present specification is not to be construed as being limited to the examples described below. Examples of the present specification are provided in order to more fully describe the present specification to those having average knowledge in the art.

SYNTHESIS EXAMPLE

Preparation Example 1

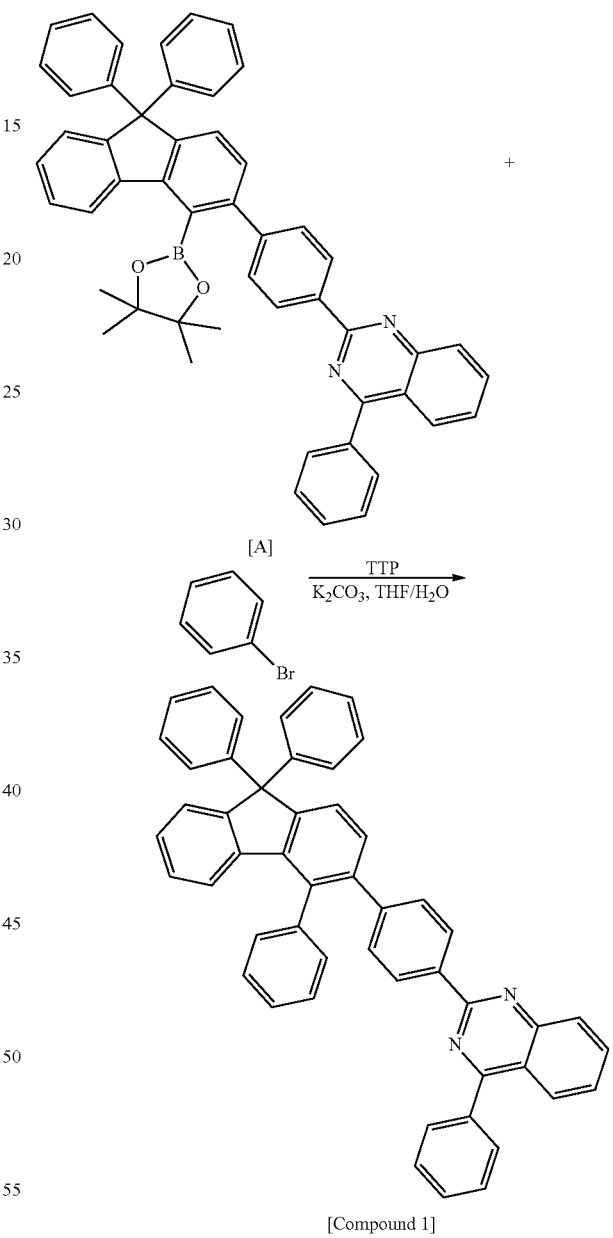

After completely dissolving Compound A (19.80 g, 27.62 mmol) and bromobenzene (4.33 g, 27.62 mmol) in tetrahydrofuran (300 ml) in a 500 ml round bottom flask under a nitrogen atmosphere, a 2 M aqueous potassium carbonate solution (150 ml) and then tetrakis-(triphenylphosphine) palladium (1 g, 0.87 mmol) were added thereto, and the result was stirred for 3 hours while heating. After lowering the temperature to room temperature (23±5° C.), the water layer was removed, and the result was dried with anhydrous magnesium sulfate, then vacuum concentrated, and recrystallized with ethyl acetate (180 ml) to prepare Compound 1 (11.1 g, 62%) having the structure shown above.

MS[M+H]⁺=674

Preparation Example 2

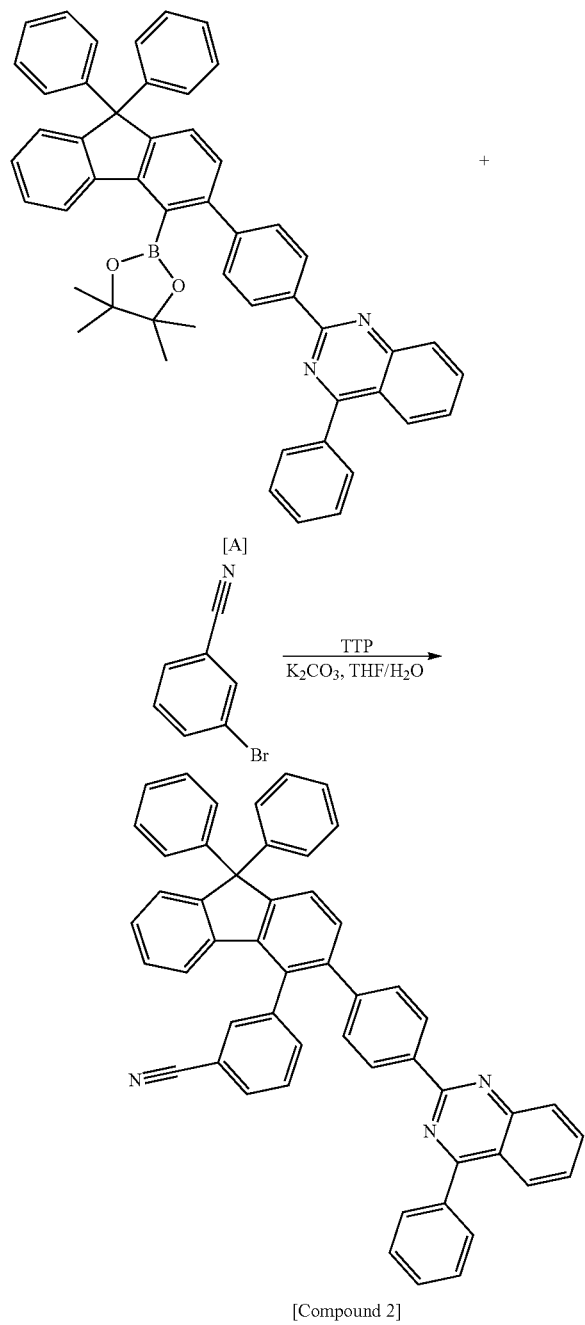

[Compound 2]

Compound 2 having the structure shown above was prepared in the same manner as in Preparation Example 1 except that 3-bromobenzonitrile was used instead of bromobenzene.

MS[M+H]+=699

Preparation Example 3

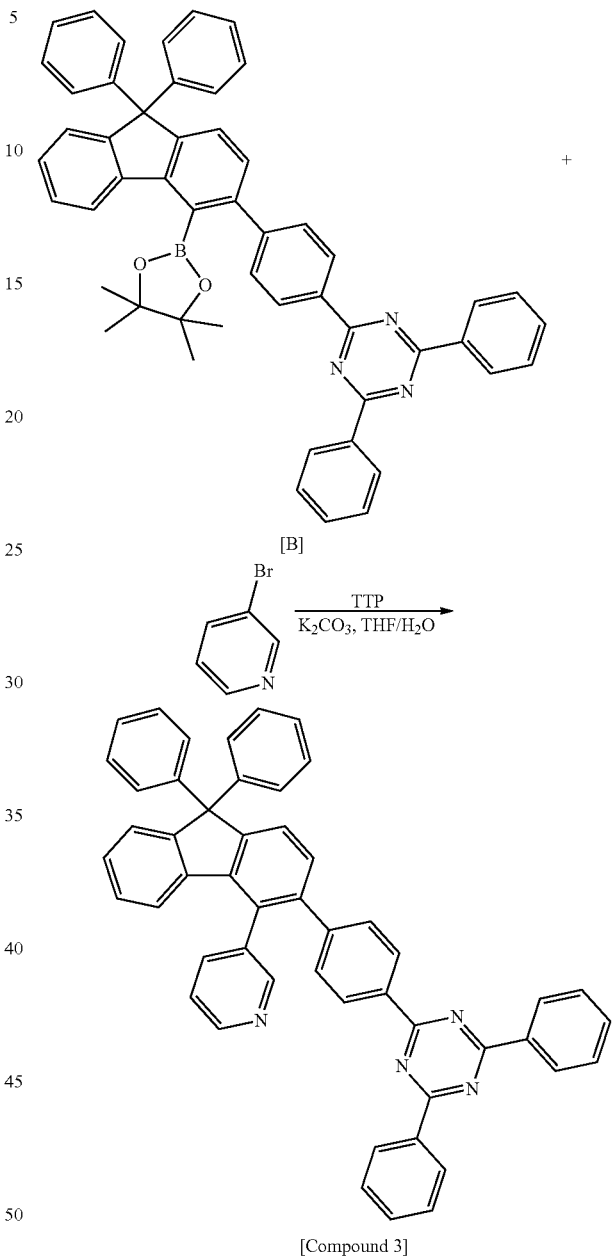

[Compound 3]

After completely dissolving Compound B (19.80 g, 26.63 mmol) and 3-bromopyridine (4.20 g, 26.63 mmol) in tetrahydrofuran (300 ml) in a 500 ml round bottom flask under a nitrogen atmosphere, a 2 M aqueous potassium carbonate solution (150 ml) and then tetrakis-(triphenylphosphine)-palladium (0.92 g, 0.79 mmol) were added thereto, and the result was stirred for 3 hours while heating. After lowering the temperature to room temperature (23±5° C.), the water layer was removed, and the result was dried with anhydrous magnesium sulfate, then vacuum concentrated, and recrystallized with ethyl acetate (180 ml) to prepare Compound 3 (13.1 g, 69%) having the structure shown above.

MS[M+H]⁺=702

Preparation Example 4

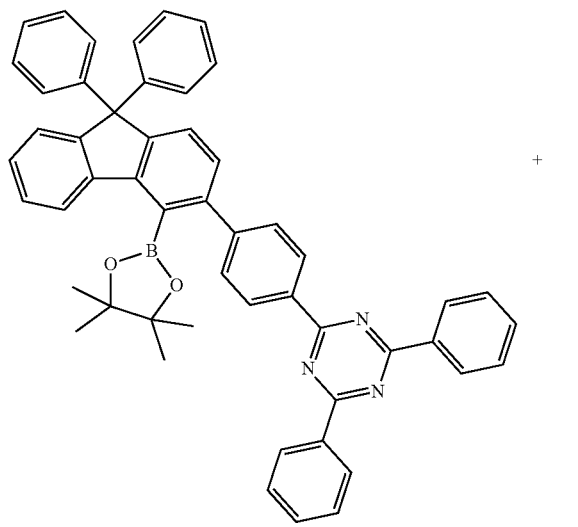

[B]

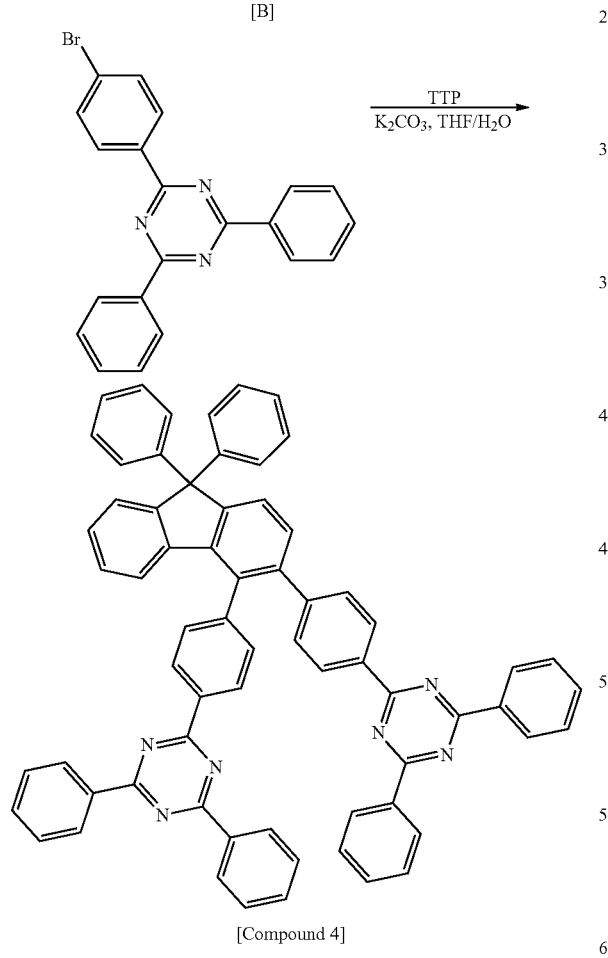

[Compound 4]

Compound 4 having the structure shown above was prepared in the same manner as in Preparation Example 3 except that 2-(4-bromophenyl)-4,6-diphenyl-1,3,5-triazine was used instead of 3-bromopyridine.

MS[M+H]+=933

Preparation Example 5

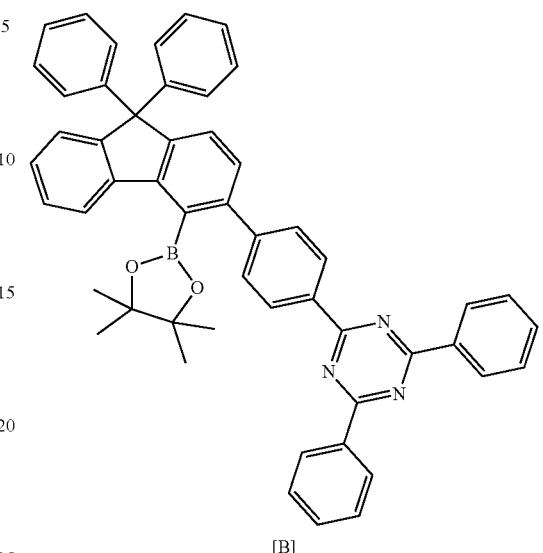

[B]

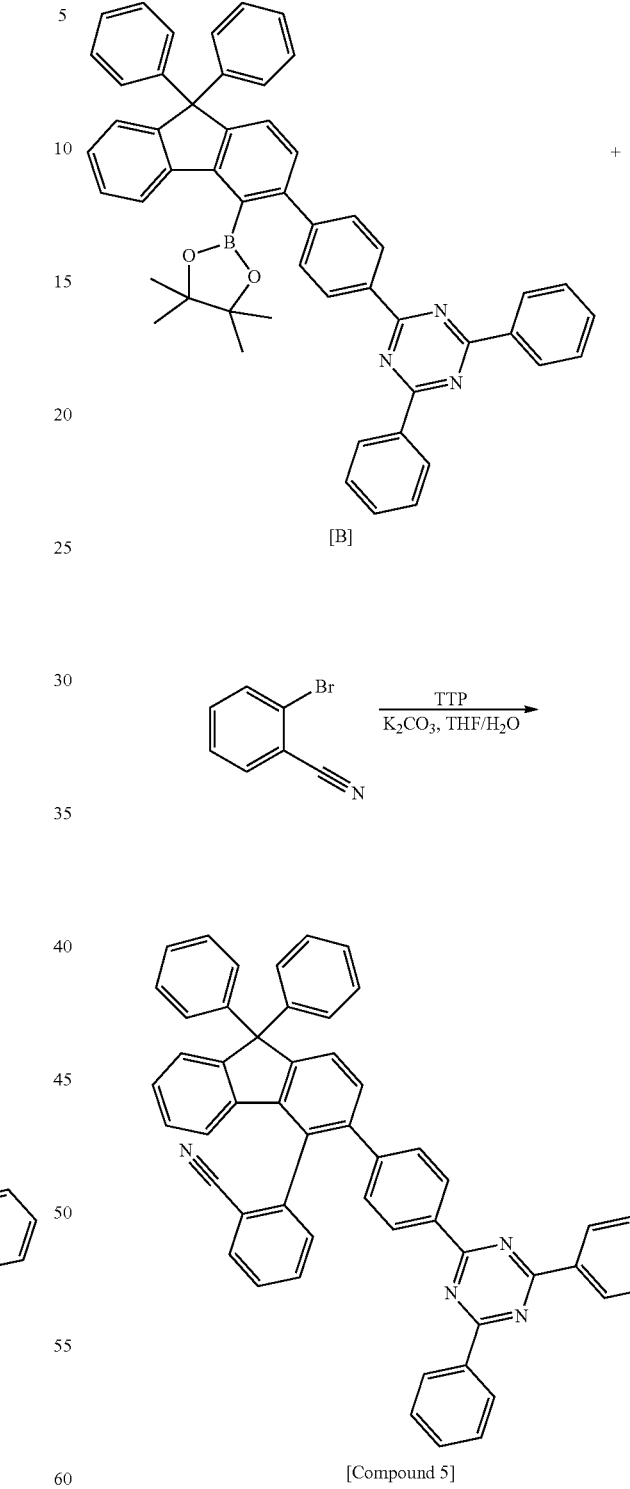

[Compound 5]

Compound 5 having the structure shown above was prepared in the same manner as in Preparation Example 3 except that 2-bromobenzonitrile was used instead of 3-bromopyridine.

MS[M+H]+=726

Preparation Example 6

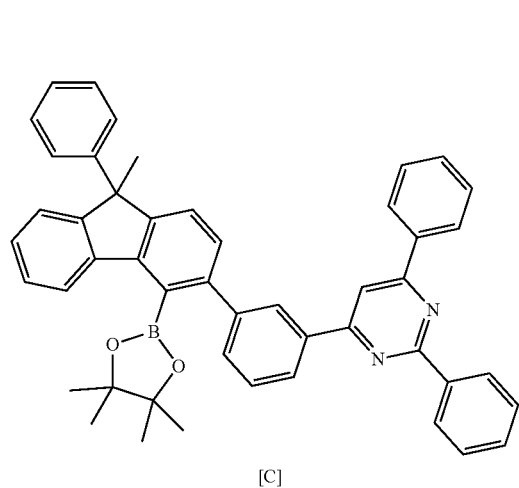

[C]

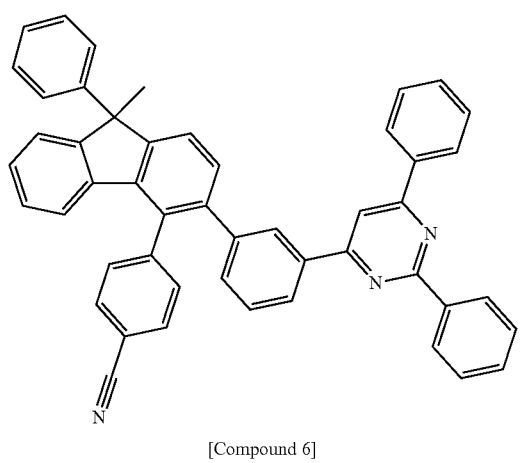

[Compound 6]

After completely dissolving Compound C (19.80 g, 29.06 mmol) and 4-bromobenzonitrile (5.29 g, 29.06 mmol) in tetrahydrofuran (300 ml) in a 500 ml round bottom flask under a nitrogen atmosphere, a 2 M aqueous potassium carbonate solution (150 ml) and then tetrakis-(triphenylphosphine)-palladium (1.00 g, 0.79 mmol) were added thereto, and the result was stirred for 3 hours while heating. After lowering the temperature to room temperature (23±5° C.), the water layer was removed, and the result was dried with anhydrous magnesium sulfate, then vacuum concentrated, and recrystallized with ethyl acetate (180 ml) to prepare Compound 6 (11.9 g, 61%) having the structure shown above.

MS[M+H]⁺=663

Preparation Example 7

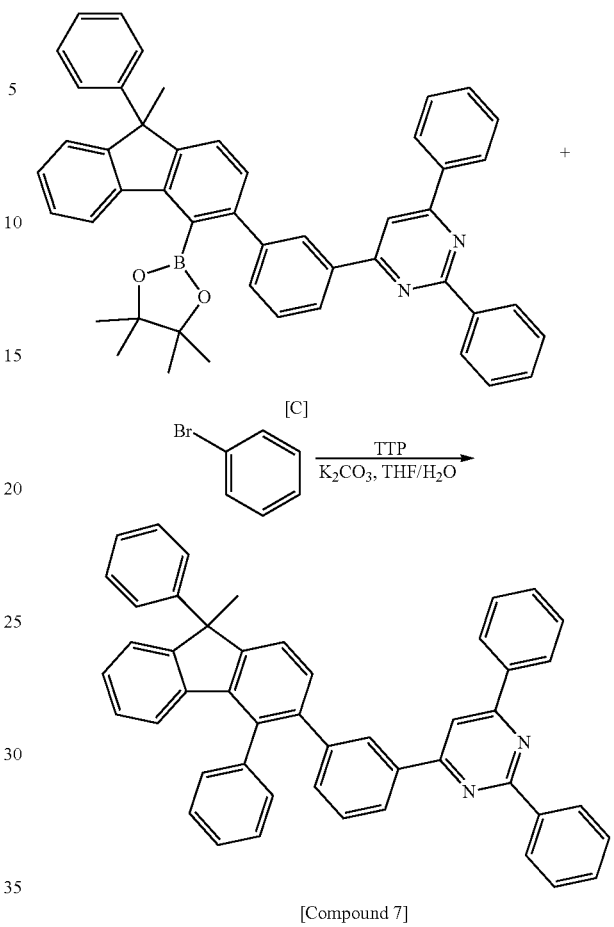

[Compound 7]

Compound 7 having the structure shown above was prepared in the same manner as in Preparation Example 6 except that bromobenzene was used instead of 4-bromobenzonitrile.

MS[M+H]+=638

Preparation Example 8

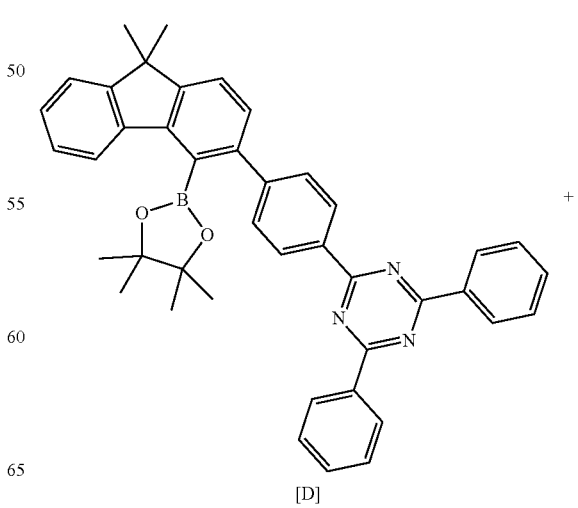

[D]

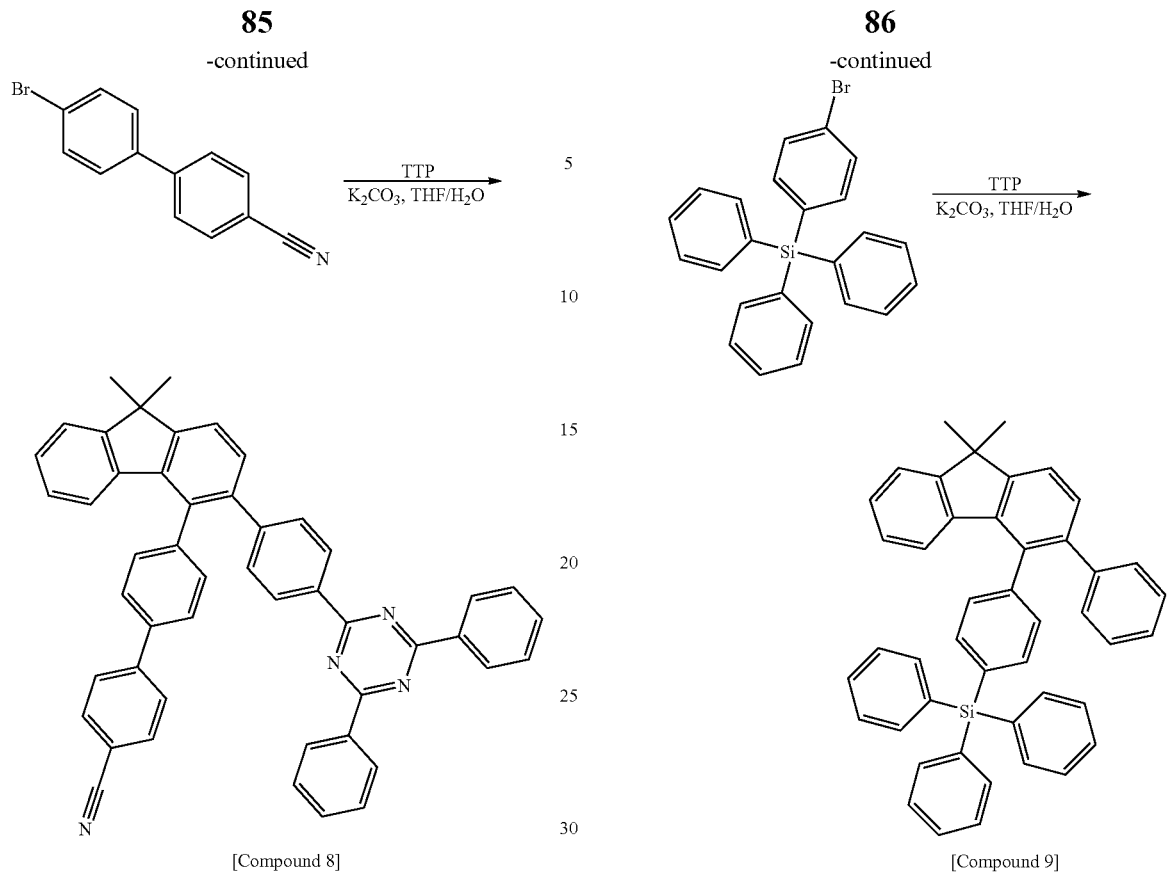

[Compound 8]

[Compound 9]

After completely dissolving Compound D (19.80 g, 31.89 mmol) and 4'-bromo-[1,1'-biphenyl]-4-carbonitrile (8.22 g, 31.89 mmol) in tetrahydrofuran (300 ml) in a 500 ml round bottom flask under a nitrogen atmosphere, a 2 M aqueous potassium carbonate solution (150 ml) and then tetrakis-(triphenylphosphine)palladium (1.10 g, 0.95 mmol) were added thereto, and the result was stirred for 3 hours while heating. After lowering the temperature to room temperature (23±5° C.), the water layer was removed, and the result was dried with anhydrous magnesium sulfate, then vacuum concentrated, and recrystallized with ethyl acetate (180 ml) to prepare Compound 8 (12.8 g, 59%) having the structure shown above.

MS[M+H]$^+$=678

After completely dissolving Compound E (19.80 g, 50.50 mmol) and (4-bromophenyl)triphenylsilane (20.95 g, 50.50 mmol) in tetrahydrofuran (300 ml) in a 500 ml round bottom flask under a nitrogen atmosphere, a 2 M aqueous potassium carbonate solution (150 ml) and then tetrakis-(triphenylphosphine)palladium (1.75 g, 1.51 mmol) were added thereto, and the result was stirred for 3 hours while heating. After lowering the temperature to room temperature (23±5° C.), the water layer was removed, and the result was dried with anhydrous magnesium sulfate, then vacuum concentrated, and recrystallized with ethyl acetate (180 ml) to prepare Compound 9 (19.5 g, 65%) having the structure shown above.

MS[M+H]$^+$=604

Preparation Example 9

Preparation Example 10

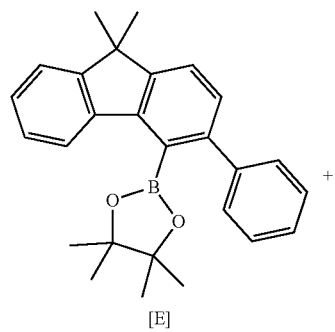

[E]

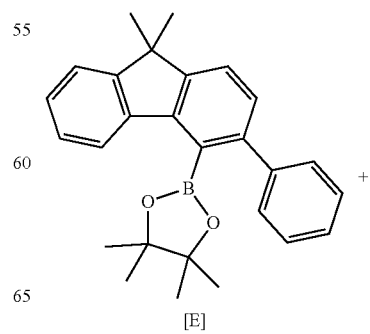

[E]

-continued

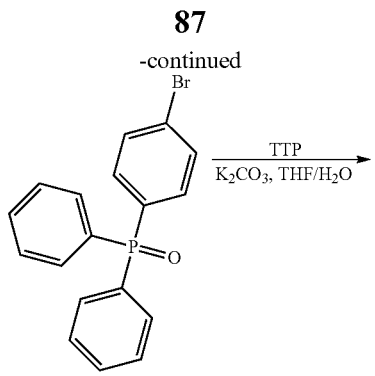

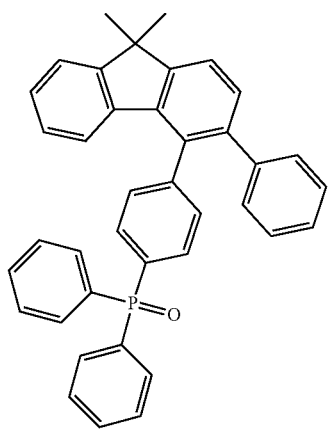

[Compound 10]

Compound 10 having the structure shown above was prepared in the same manner as in Preparation Example 9 except that (4-bromophenyl)diphenylphosphine oxide was used instead of (4-bromophenyl)triphenylsilane.

MS[M+H]+=546

Preparation Example 11

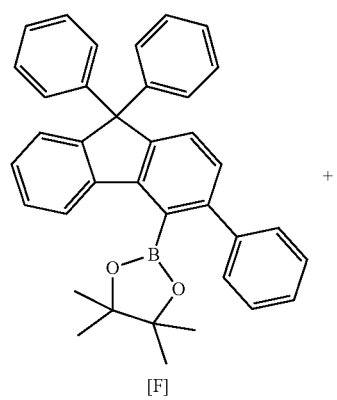

-continued

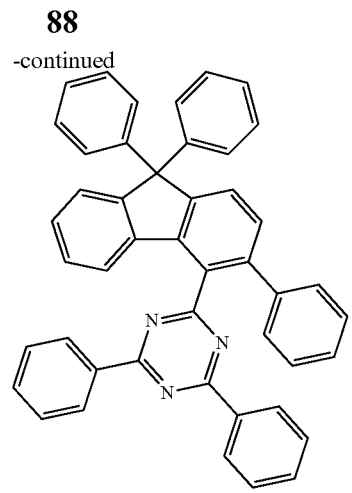

[Compound 11]

Compound 11 having the structure shown above was prepared in the same manner as in Preparation Example 9 except that Compound F was used instead of Compound E, and 2-chloro-4,6-diphenyl-1,3,5-triazine was used instead of (4-bromophenyl)-triphenylsilane.

Preparation Example 12

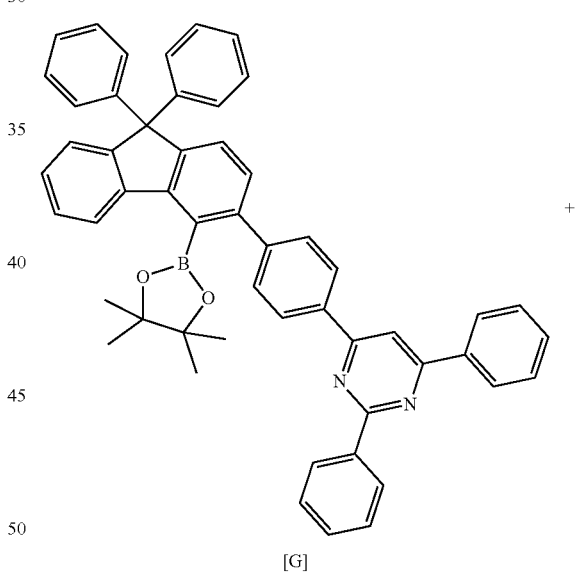

[G]

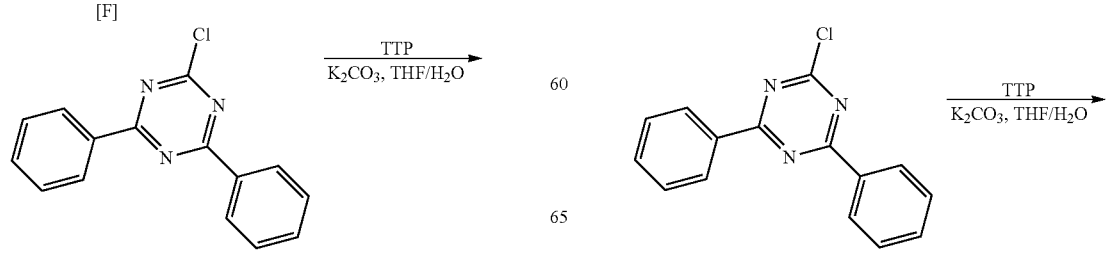

-continued

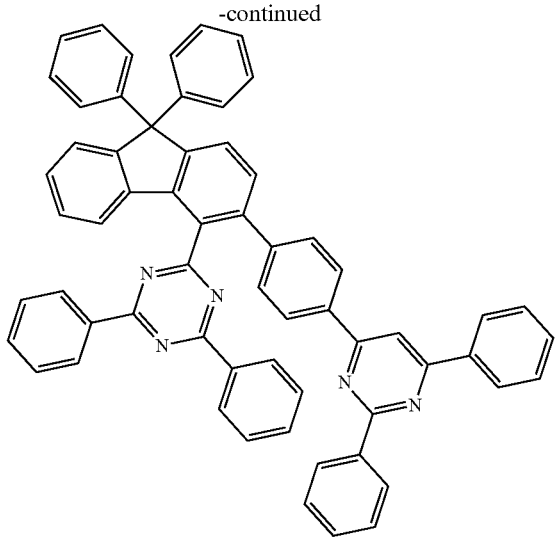

[Compound 12]

Compound 12 having the structure shown above was prepared in the same manner as in Preparation Example 9 except that Compound G was used instead of Compound E, and 2-chloro-4,6-diphenyl-1,3,5-triazine was used instead of (4-bromophenyl)-triphenylsilane.

Example 1-1

A glass substrate on which indium tin oxide (ITO) was coated as a thin film to a thickness of 1,000 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus.

On the transparent ITO electrode prepared as above, a hole injection layer was formed by thermal vacuum depositing hexanitrile hexaazatriphenylene (HAT) of the following chemical formula to a thickness of 500 Å:

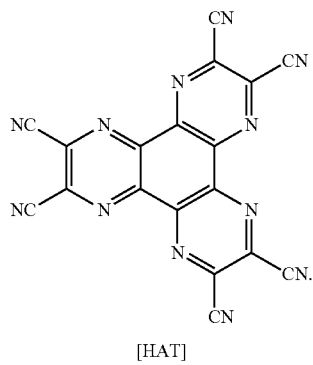

[HAT]

A hole transfer layer was formed on the hole injection layer by vacuum depositing the following compound N4,N4,N4',N4'-tetra([1,1'-biphenyl]-4-yl)-[1,1'-biphenyl]-4,4'-diamine [HT 1] (300 Å), a material transferring holes:

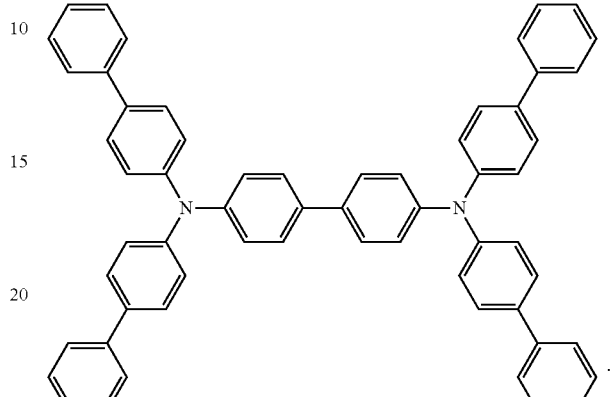

[HT 1]

Subsequently, an electron blocking layer was formed on the hole transfer layer by vacuum depositing the following [EBL] to a film thickness of 100 Å:

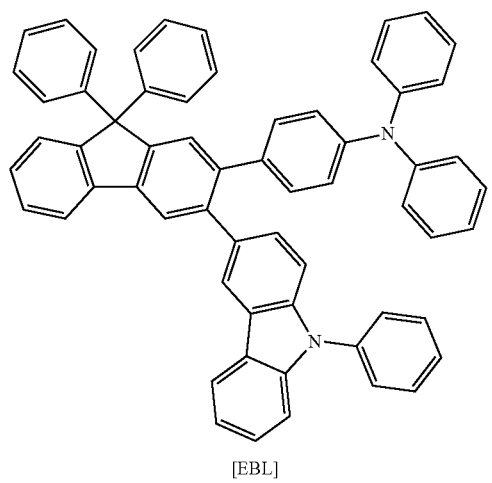

[EBL]

Subsequently, a light emitting layer was formed on the electron blocking layer to a film thickness of 300 Å by vacuum depositing the following BH and BD in a weight ratio of 25:1:

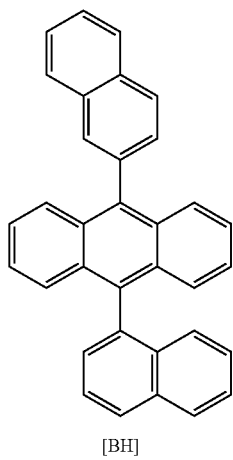

[BH]

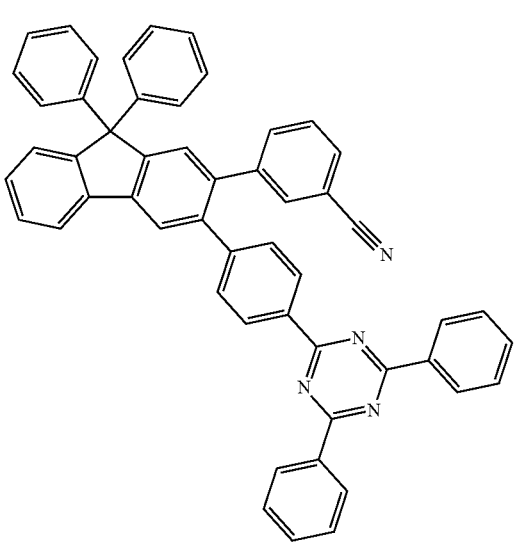

[BD]

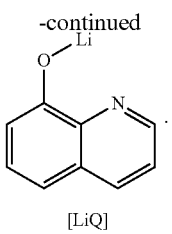

[LiQ]

On the light emitting layer, an electron injection and transfer layer was formed to a thickness of 300 Å by vacuum depositing Compound 1 of Preparation Example 1 and the compound lithium quinolate (LiQ) in a weight ratio of 1:1. On the electron injection and transfer layer, a cathode was formed by consecutively depositing lithium fluoride (LiF) to a thickness of 12 Å and aluminum to a thickness of 2,000 Å.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2 \times 10^{-7}$ torr to $5 \times 10^{-6}$ torr to manufacture an organic light emitting device.

Examples 1-2 to 1-10

Organic light emitting devices were manufactured in the same manner as in Example 1-1 except that compounds described in the following Table 1 were used instead of Compound 1.

Comparative Examples 1-1 to 1-5

Organic light emitting devices were manufactured in the same manner as in Example 1-1 except that Compounds (a), (b), (c), (d) and (e) having the following structures were used instead of Compound 1.

(a)

(b)

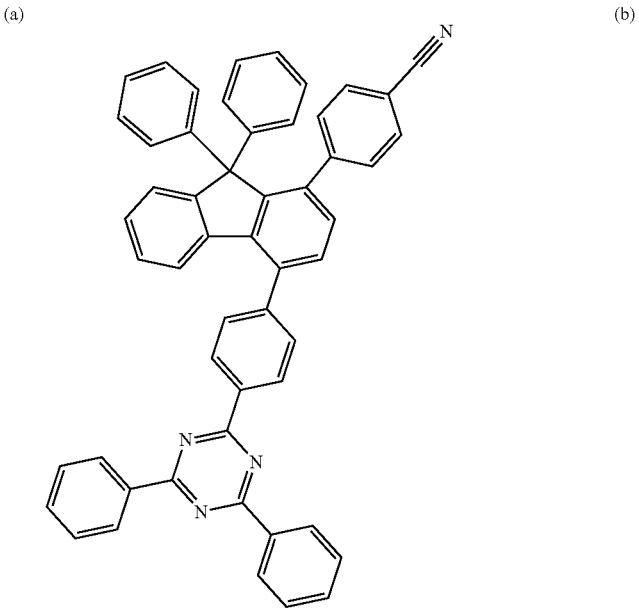

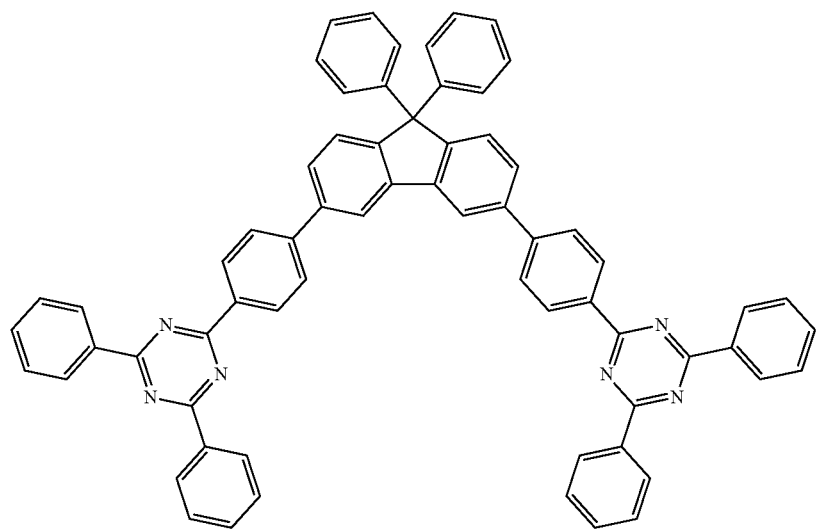

(c)

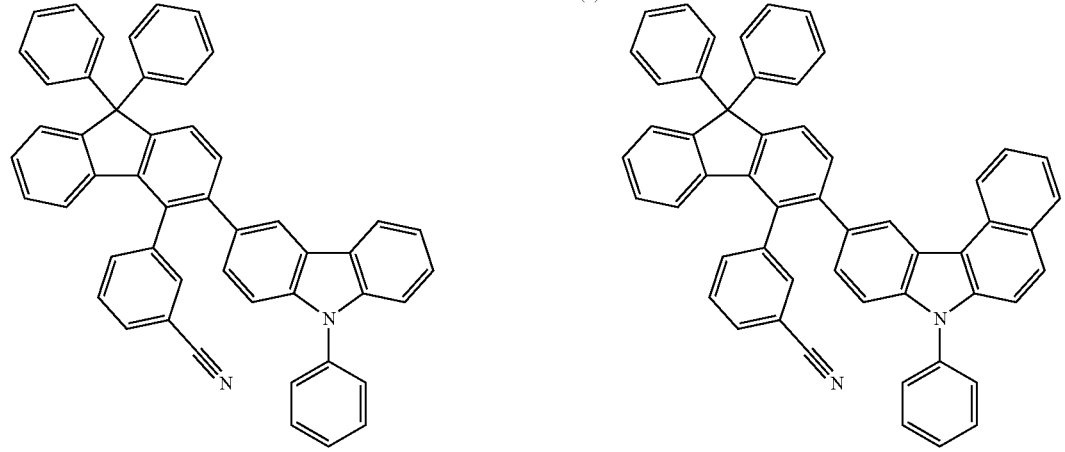

(d)           (e)

For the organic light emitting devices, driving voltage and light emission efficiency were measured at current density of 10 mA/cm², and time (T90) taken for luminance becoming 90% with respect to its initial luminance at current density of 20 mA/cm² was measured. The results are shown in the following Table 1.

TABLE 1

| | Compound | Voltage (V@10 mA/cm²) | Efficiency (cd/A@10 mA/cm²) | Color Coordinate (x, y) | Lifetime (h) $T_{90}$ at 20 mA/cm² |
|---|---|---|---|---|---|
| Example 1-1 | 1 | 4.58 | 5.51 | (0.142, 0.096) | 169 |
| Example 1-2 | 2 | 4.58 | 5.51 | (0.142, 0.096) | 169 |
| Example 1-3 | 3 | 4.67 | 5.61 | (0.142, 0.096) | 149 |
| Example 1-4 | 4 | 4.80 | 5.45 | (0.142, 0.096) | 199 |
| Example 1-5 | 5 | 4.69 | 5.60 | (0.142, 0.096) | 147 |
| Example 1-6 | 6 | 4.59 | 5.75 | (0.142, 0.099) | 158 |
| Example 1-7 | 7 | 4.57 | 5.71 | (0.142, 0.096) | 160 |
| Example 1-8 | 8 | 4.58 | 5.51 | (0.142, 0.096) | 169 |
| Example 1-9 | 9 | 4.62 | 5.51 | (0.142, 0.096) | 169 |
| Example 1-10 | 10 | 4.62 | 5.51 | (0.142, 0.096) | 169 |
| Comparative Example 1-1 | a | 4.92 | 4.15 | (0.142, 0.099) | 98 |
| Comparative Example 1-2 | b | 5.02 | 4.33 | (0.142, 0.096) | 111 |
| Comparative Example 1-3 | c | 5.11 | 4.15 | (0.142, 0.099) | 112 |
| Comparative Example 1-4 | d | 5.55 | 3.75 | (0.142, 0.099) | 114 |

TABLE 1-continued

| | Compound | Voltage (V@10 mA/cm$^2$) | Efficiency (cd/A@10 mA/cm$^2$) | Color Coordinate (x, y) | Lifetime (h) T$_{90}$ at 20 mA/cm$^2$ |
|---|---|---|---|---|---|
| Comparative Example 1-5 | e | 5.15 | 3.95 | (0.142, 0.098) | 117 |

From the results of Table 1, it was identified that the heterocyclic compound of Chemical Formula 1 was able to be used in an electron injection and transfer layer of an organic light emitting device.

In addition, when comparing Examples 1-1 to 1-10 and Comparative Examples 1-1 to 1-3, it was identified that the compound having positions 3 and 4 of the fluorene asymmetrically substituted like Chemical Formula 1 exhibited superior properties in terms of driving voltage, efficiency and lifetime in the organic light emitting device compared to the compound having substituents at positions 2 and 3 or positions 1 and 4 of the fluorene skeleton and the compound having substituents symmetrically on both sides of the fluorene skeleton. Such a result is due to the fact that the heterocyclic compound of Chemical Formula 1 induces to more favorably exhibit properties of the substituent itself compared to the compound having substitution at positions 2 and 3, and positions 1 and 4 with a relatively short conjugation link and the symmetrical compound.

In addition, when comparing Example 1-2 with Comparative Examples 1-4 and 1-5, it was identified that efficiency and voltage are significantly lowered when there are substituents based on carbazole or benzocarbazole on the fluorene skeleton like the compound (d) or (e), and this is due to the fact that electron donor properties of the substituent lower electron transfer and electron injection properties.

Particularly, the hetero compound included in Examples 1-4, 1-8, 1-9 and 1-10 had high electron mobility with deep HOMO energy of 6.1 eV or greater, and exhibited more superior properties in terms of driving voltage, efficiency and lifetime when used in an organic light emitting device.

In addition, when using the heterocyclic compound of Chemical Formula 1 in an electron injection and transfer layer, an n-type dopant used in the art can be mixed thereto. Accordingly, the heterocyclic compound of Chemical Formula 1 has low driving voltage and high efficiency, and is capable of enhancing device stability by hole stability of the compound.

The invention claimed is:

1. A compound of Chemical Formula 1:

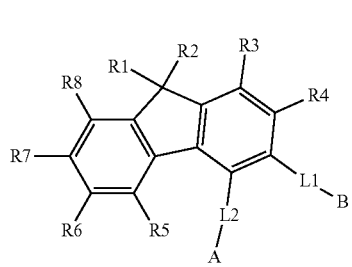

Chemical Formula 1 wherein, in Chemical Formula 1:

R1 and R2 are the same as or different from each other, and each independently is a substituted or unsubstituted alkyl group, a substituted or unsubstituted alkylaryl group, or a substituted or unsubstituted aryl group;

R3 to R8 are the same as or different from each other, and each independently is hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted alkenyl group, a substituted or unsubstituted silyl group, a substituted or unsubstituted amine group, a substituted or unsubstituted aryl group, or a substituted or unsubstituted heteroaryl group;

L1 and L2 are the same as or different from each other, and each independently is a direct bond, a substituted or unsubstituted arylene group, a substituted or unsubstituted monocyclic or dicyclic heteroarylene group, a substituted or unsubstituted divalent dibenzofuran group, a substituted or unsubstituted divalent dibenzothiophene group, a substituted or unsubstituted divalent phenoxazine group, or a substituted or unsubstituted divalent phenothiazine group;

A and B are the same as or different from each other, and each independently is a substituted or unsubstituted aryl group, a substituted or unsubstituted monocyclic or dicyclic heteroaryl group, a substituted or unsubstituted dibenzofuran group, a substituted or unsubstituted benzonaphthofuran group, a substituted or unsubstituted dibenzothiophene group, a substituted or unsubstituted benzonaphthothiophene group, a substituted or unsubstituted phenoxazine group, a substituted or unsubstituted phenothiazine group, a substituted or unsubstituted phenanthroline group, a substituted or unsubstituted benzoquinoline group, a substituted or unsubstituted arylamine group, a substituted or unsubstituted silyl group, or a substituted or unsubstituted phosphine oxide group, or one of the following substituents:

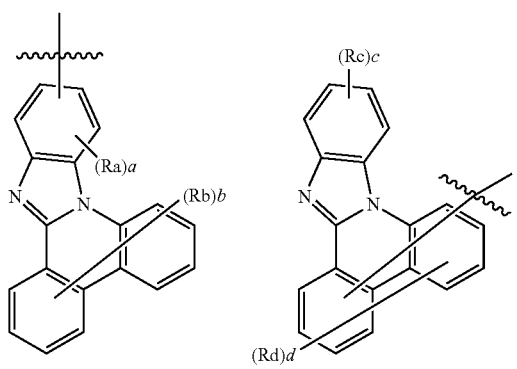

-continued

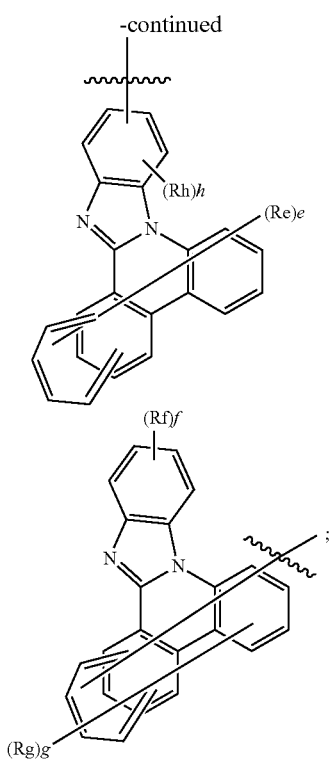

wherein:
Ra to Rh are the same as or different from each other, and each independently is hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted alkenyl group, a substituted or unsubstituted silyl group, a substituted or unsubstituted amine group, a substituted or unsubstituted aryl group, or a substituted or unsubstituted heteroaryl group;
a and h are each an integer of 0 to 3, b is an integer of 0 to 8, c and f are each an integer of 0 to 4, d is an integer of 0 to 7, e is an integer of 0 to 10, and g is an integer of 0 to 9,
wherein for variables R1-R8, L1, L2, A, B, and Ra to Rh, when a substituent is substituted, it is substituted with any one, two, or more substituents selected from the group consisting of deuterium, a nitrile group, an alkyl group, a cycloalkyl group, an alkoxy group, an aryloxy group, an alkenyl group, a silyl group, a boron group, an amine group, an aryl group, and a heterocyclic group.

2. The compound of claim 1, wherein A and B are the same as or different from each other, and each independently is a substituted or unsubstituted aryl group having 6 to 30 carbon atoms, a substituted or unsubstituted arylamine group having 6 to 30 carbon atoms, a substituted or unsubstituted silyl group, a substituted or unsubstituted arylphosphine oxide group having 6 to 30 carbon atoms, a substituted or unsubstituted alkylphosphine oxide group having 1 to 30 carbon atoms, a substituted or unsubstituted pyridine group, a substituted or unsubstituted pyrimidine group, a substituted or unsubstituted triazine group, a substituted or unsubstituted quinazoline group, a substituted or unsubstituted quinolyl group, a substituted or unsubstituted isoquinolyl group, a substituted or unsubstituted benzimidazole group, a substituted or unsubstituted benzothiazole group, a substituted or unsubstituted benzoxazole group, a substituted or unsubstituted phenanthroline group, a substituted or unsubstituted benzoquinoline group, or one or the following substituents:

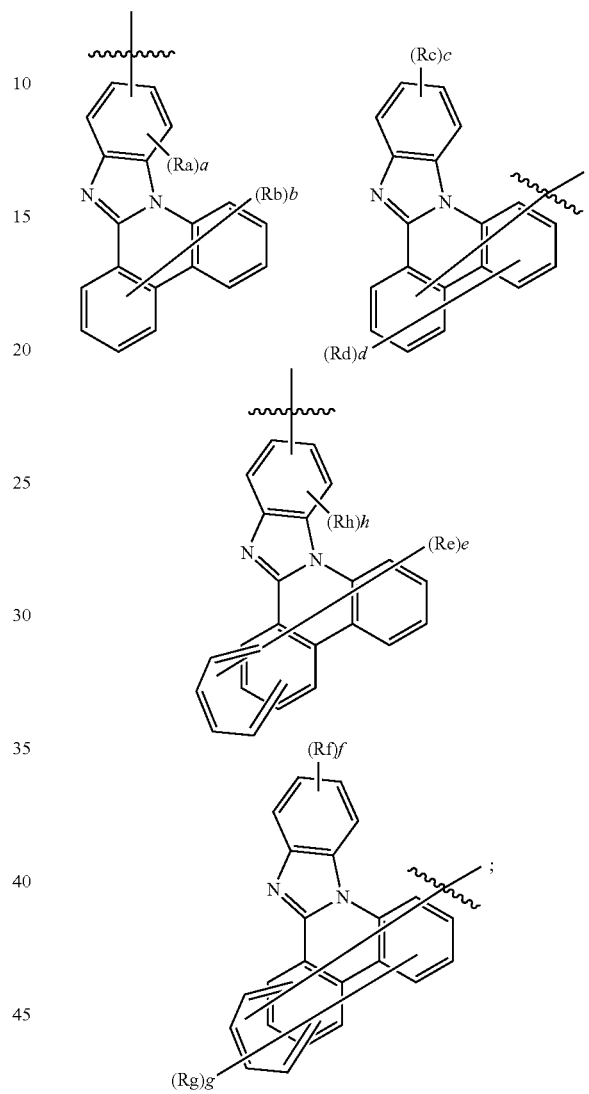

wherein Ra to Rh and a to h have the same definitions as in claim 1, and
wherein for variables A and B, when a substituent is substituted, it is substituted with any one, two, or more substituents selected from the group consisting of deuterium, a nitrile group, an alkyl group, a cycloalkyl group, an alkoxy group, an aryloxy group, an alkenyl group, a silyl group, a boron group, an amine group, an aryl group, and a heterocyclic group.

3. The compound of claim 1, wherein A and B are the same as or different from each other, and each independently is selected from among the following substituents:

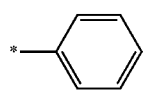 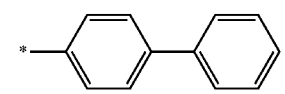

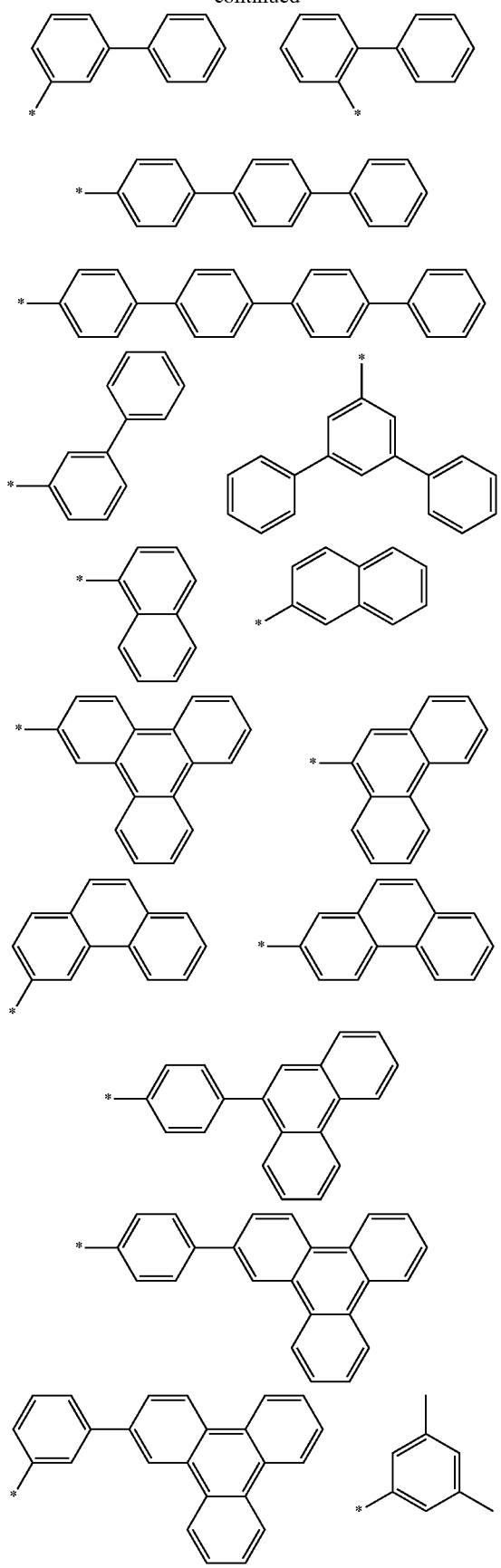
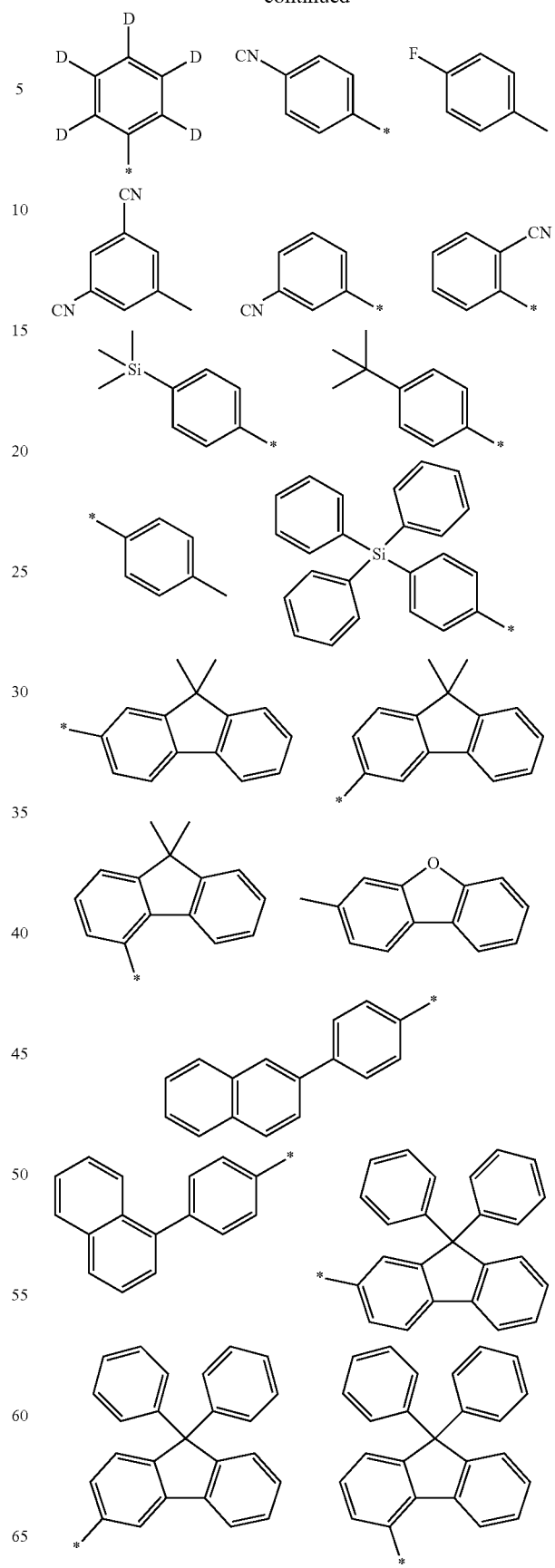

101
-continued
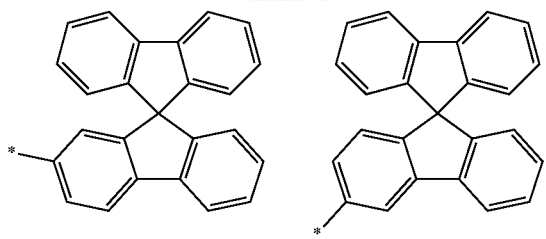
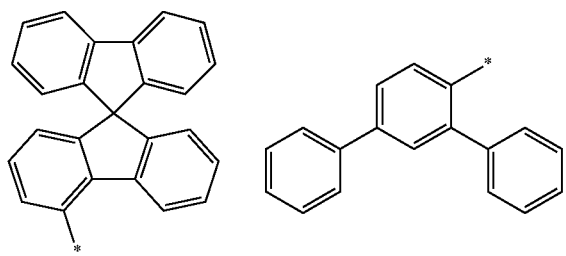
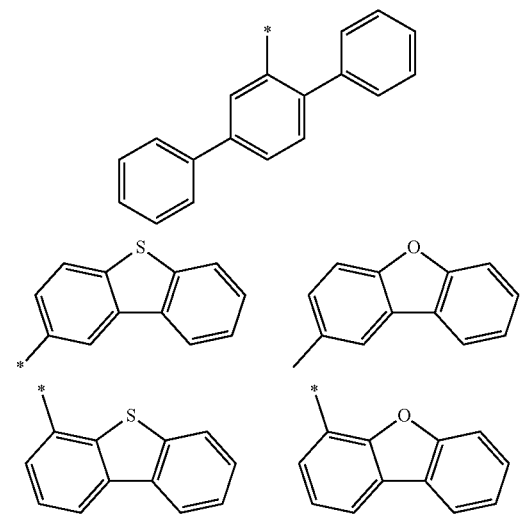
102
-continued
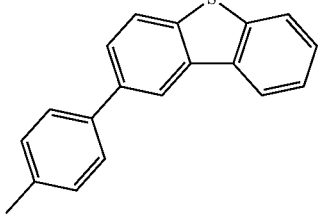
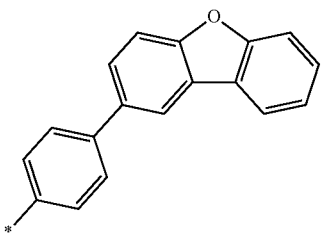
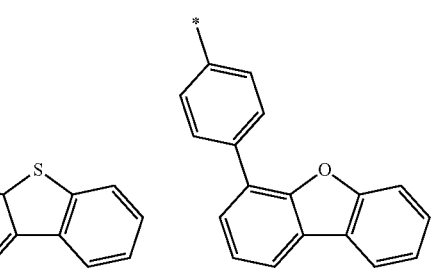
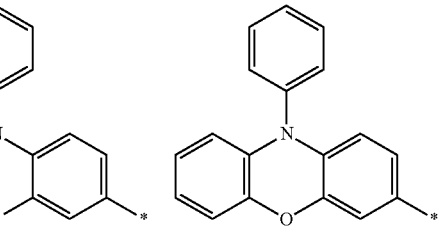
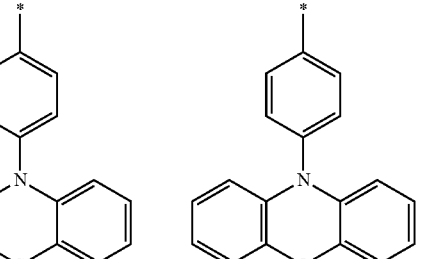
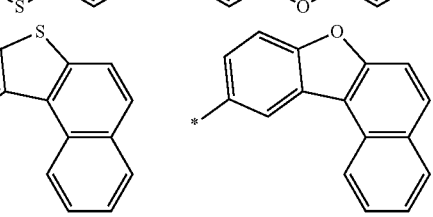
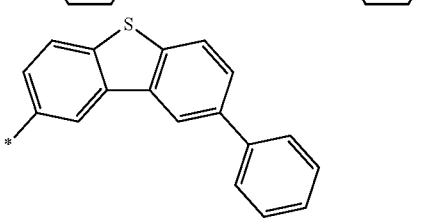

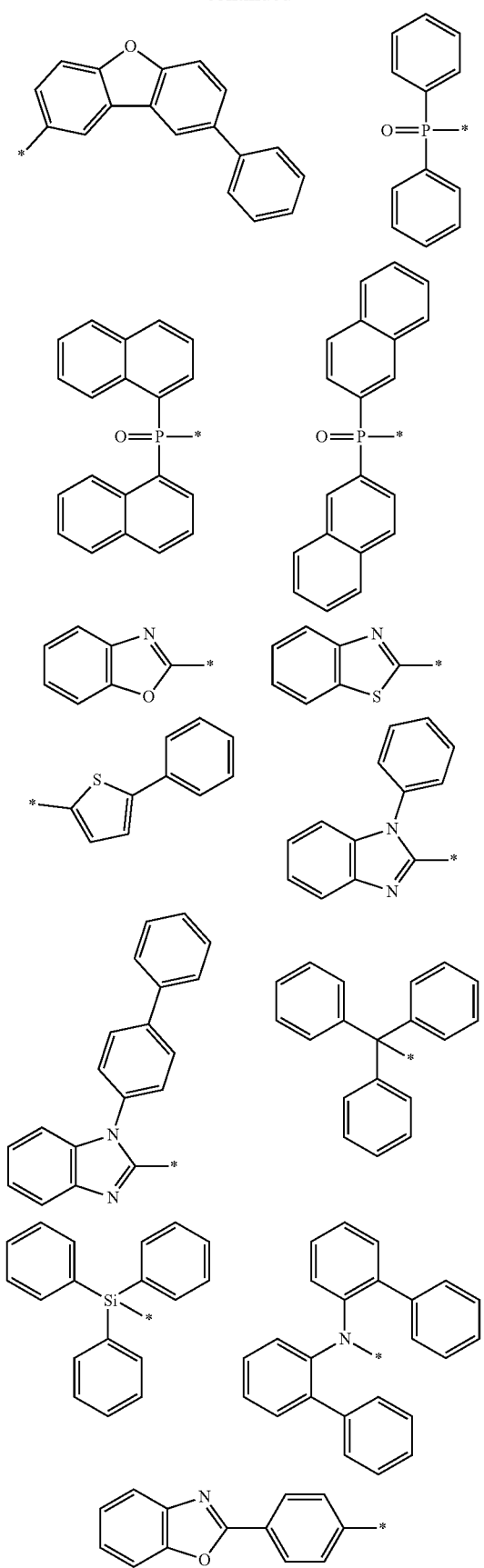
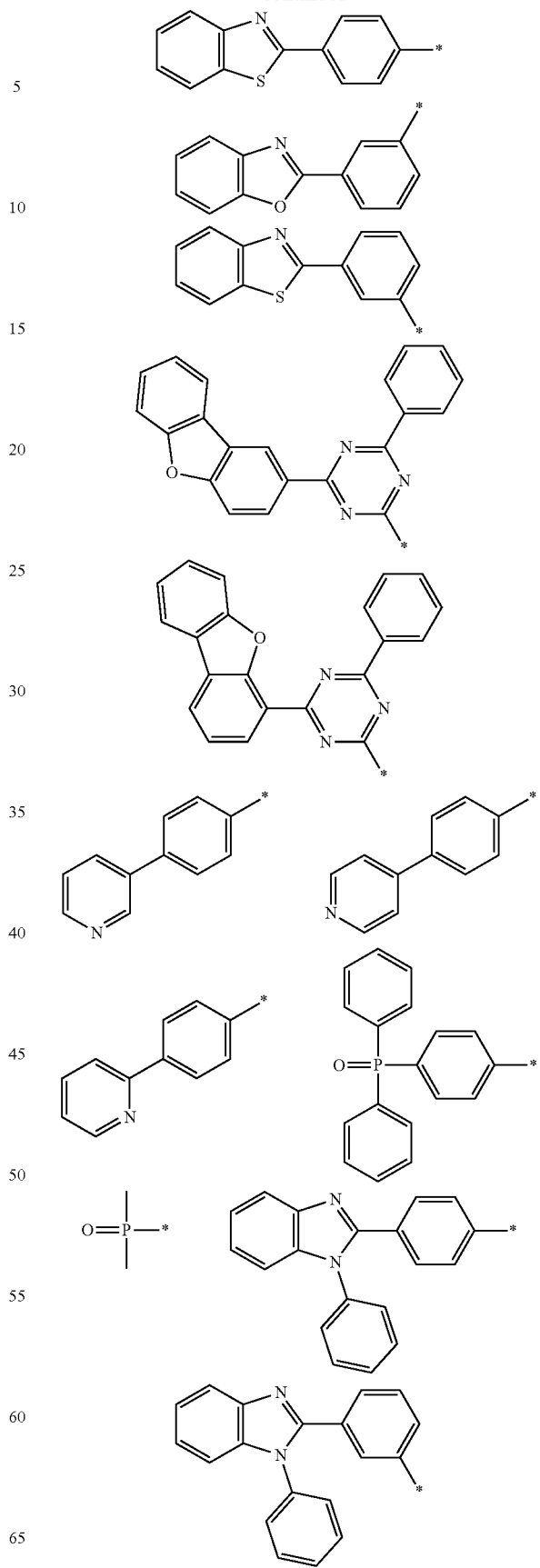

105
-continued
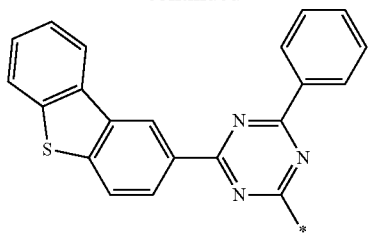
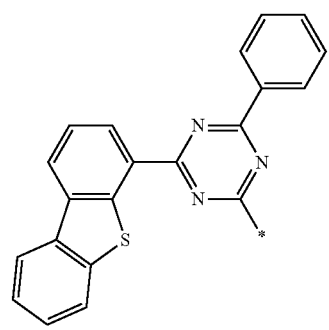
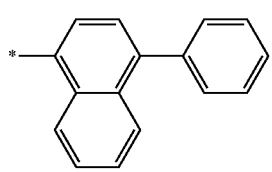
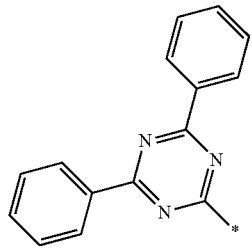
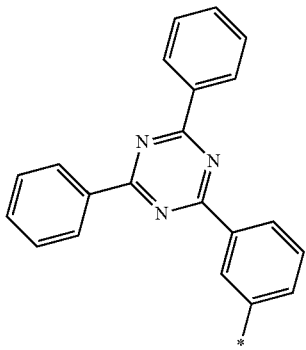
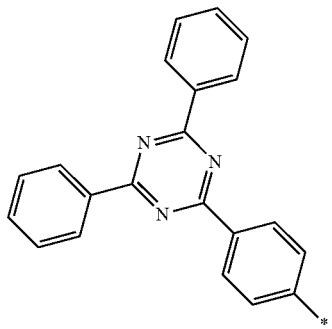
106
-continued
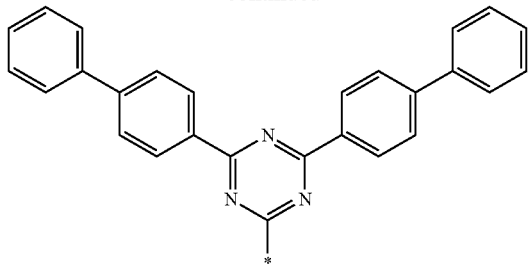
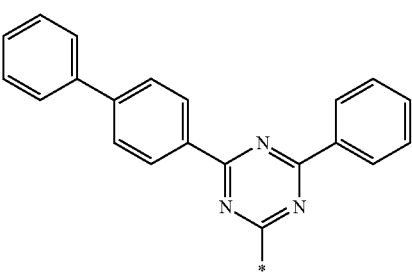
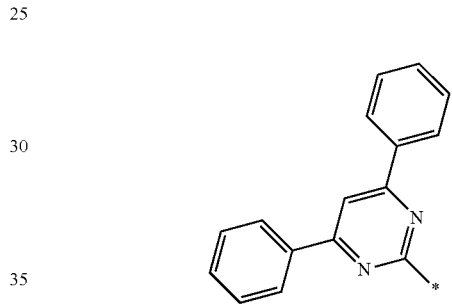
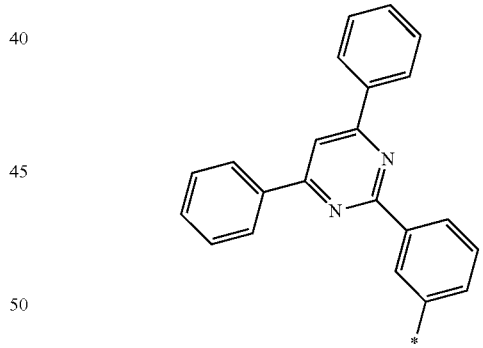
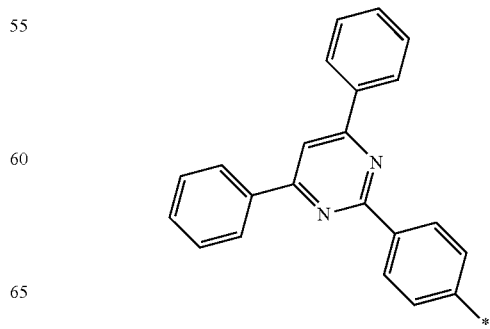

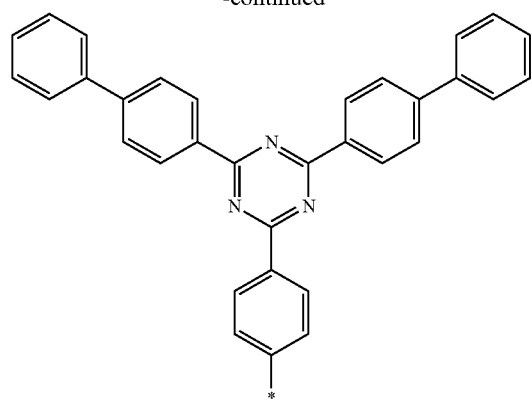
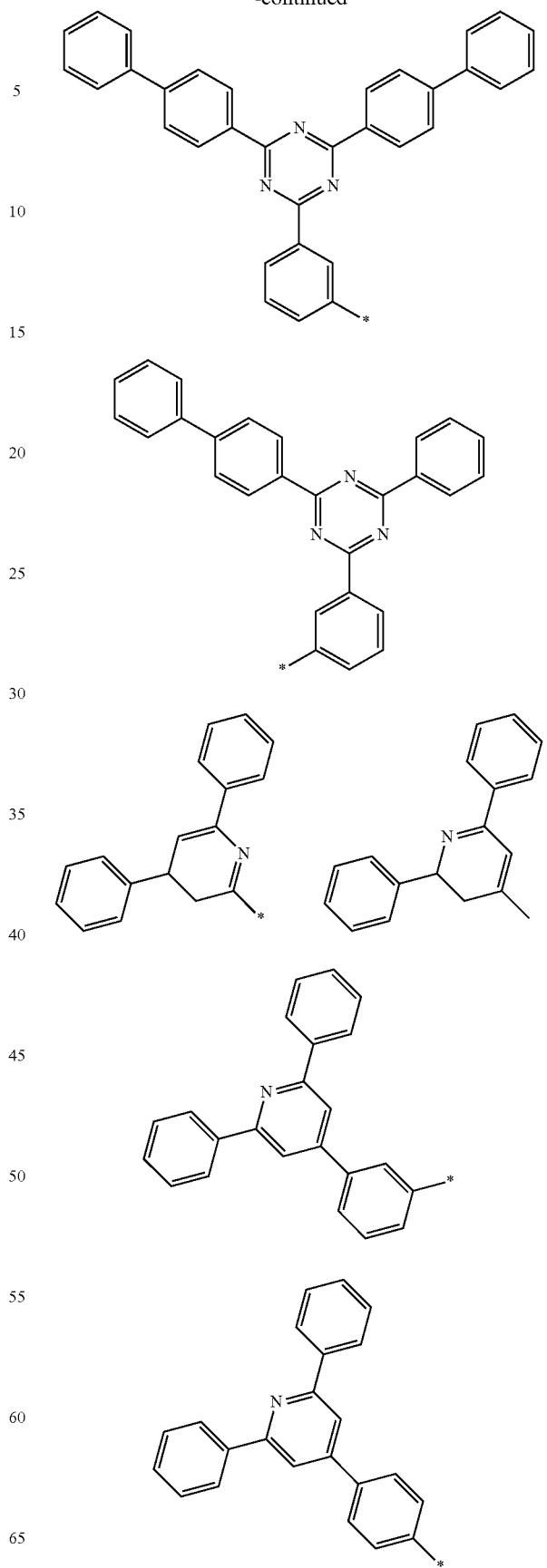

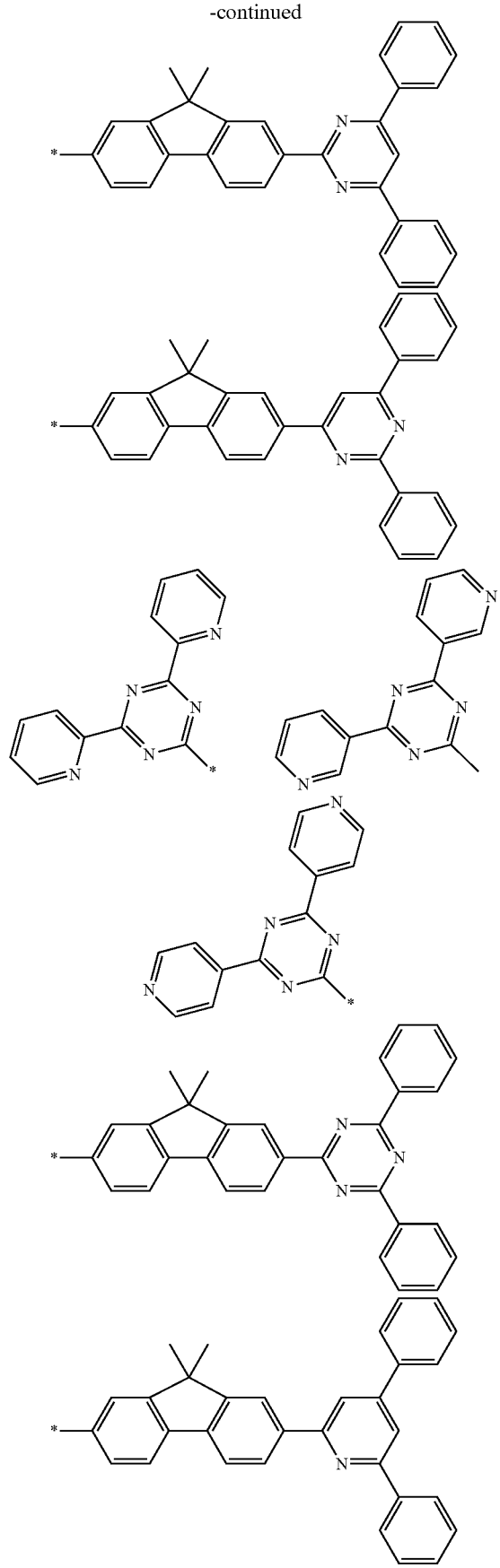

111
-continued
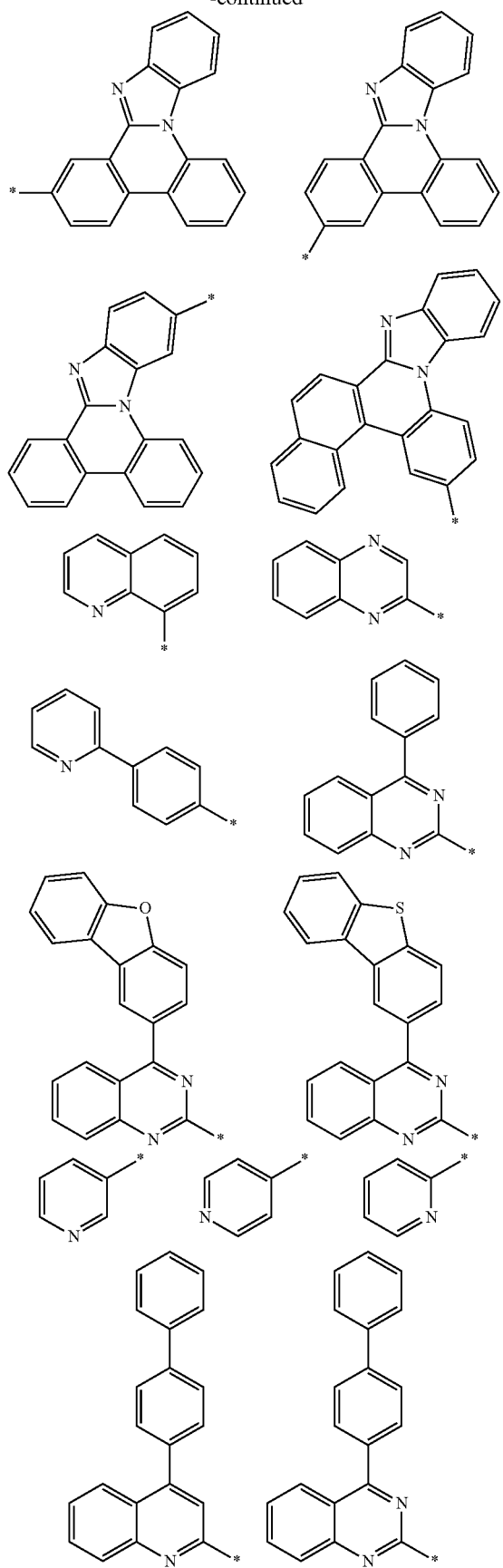
112
-continued
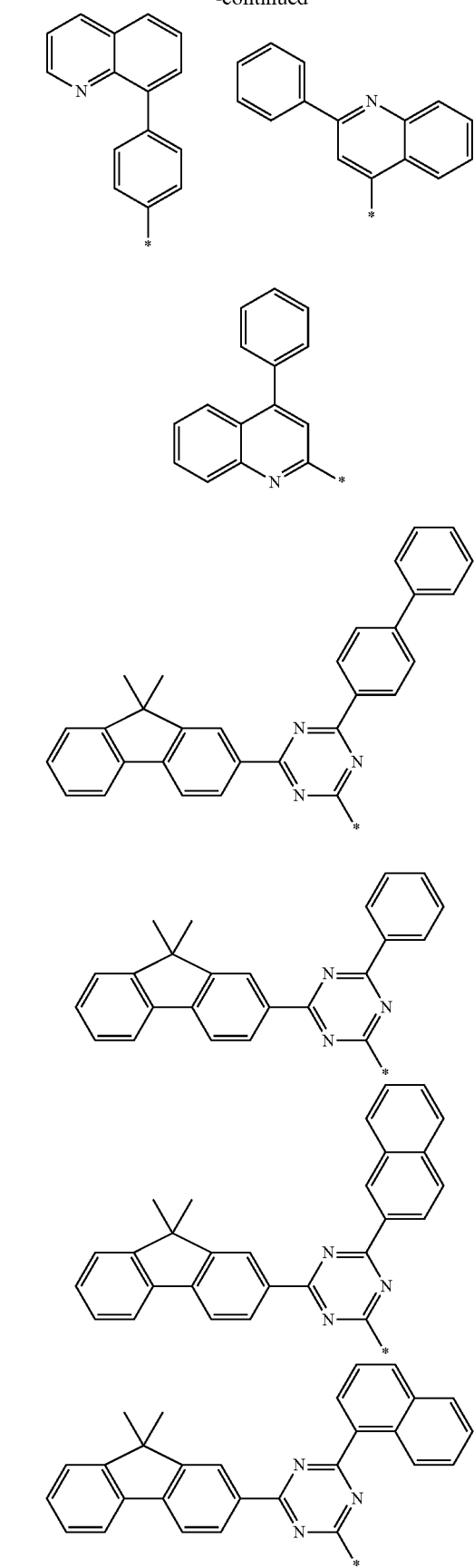

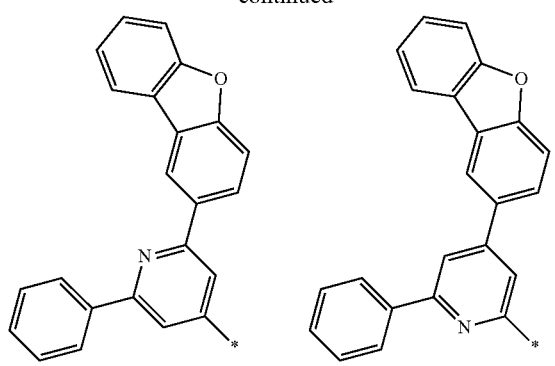
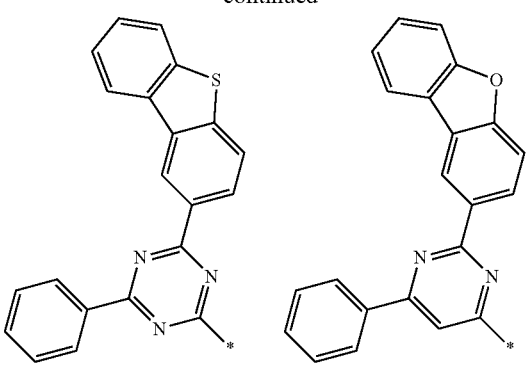
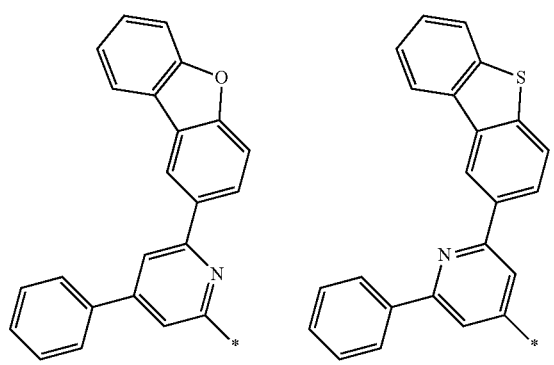
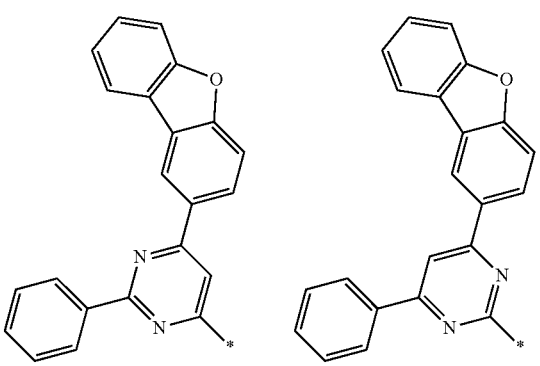
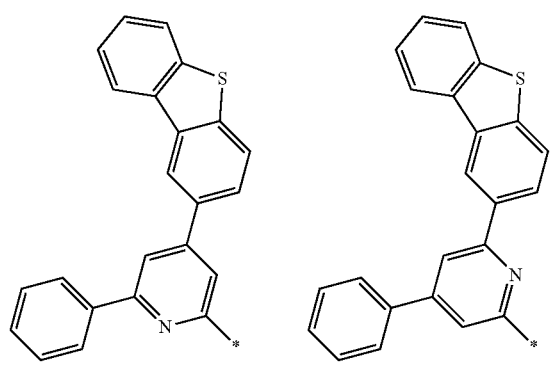
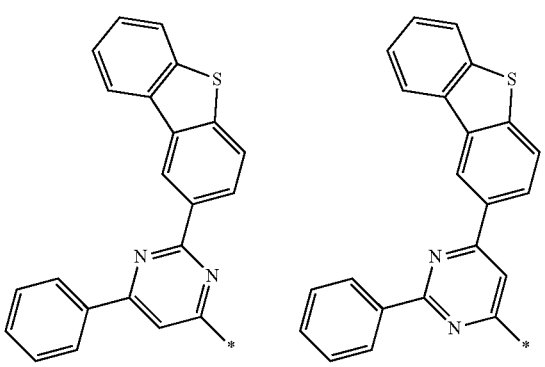
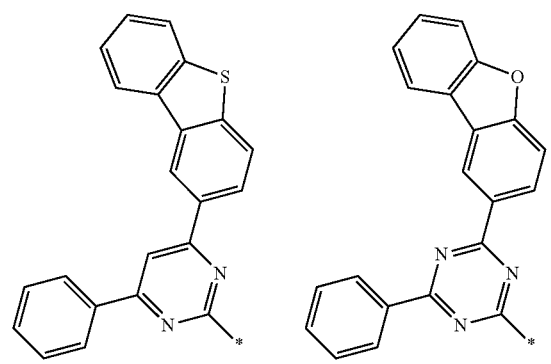
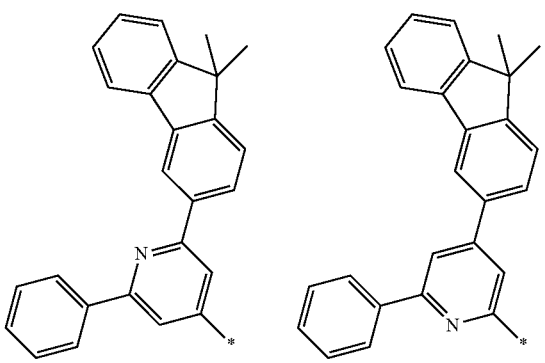

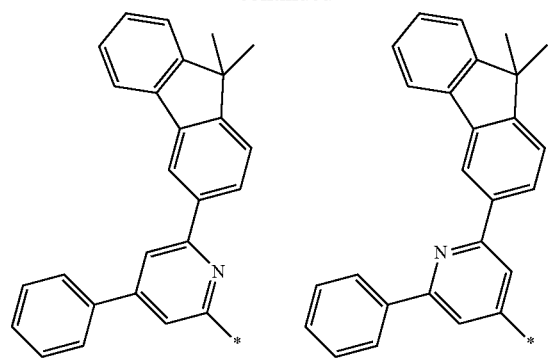
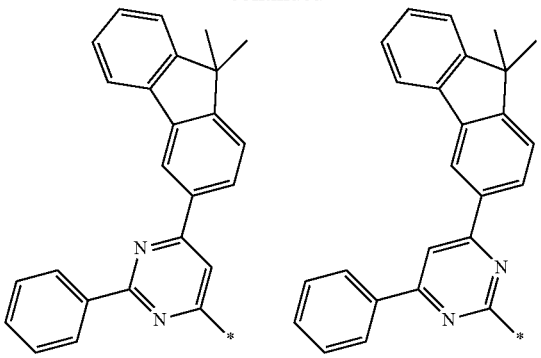

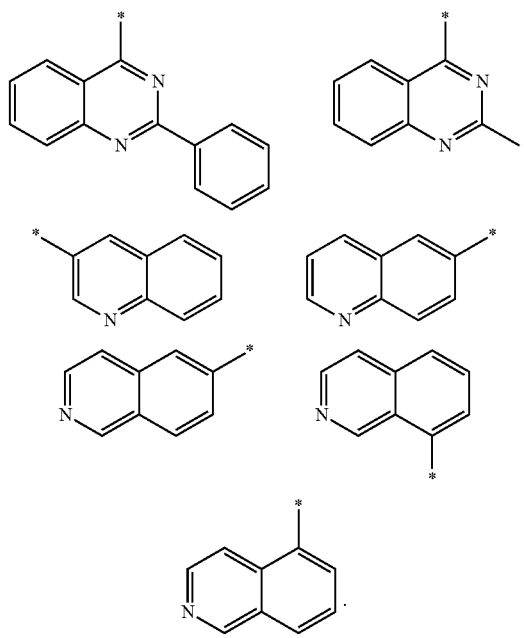

4. The compound of claim 1, wherein L1 and L2 are the same as or different from each other, and each independently is selected from among a direct bond, phenylene, biphenylylene, terphenylylene, quaterphenylylene, naphthylene, anthracenylene, phenanthrenylene, pyrenylene, triphenylylene and fluorenylene that is unsubstituted or substituted with alkyl or aryl.

5. The compound of claim 1, wherein:

R1 and R2 are all an alkyl group, or

R1 and R2 are all an aryl group, or

R1 is an alkyl group and R2 is an aryl group.

6. A substituted fluorenyl compound that is any one of the following compounds:

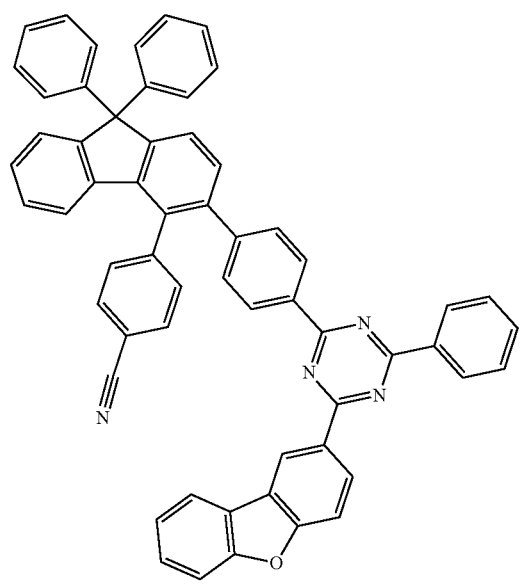

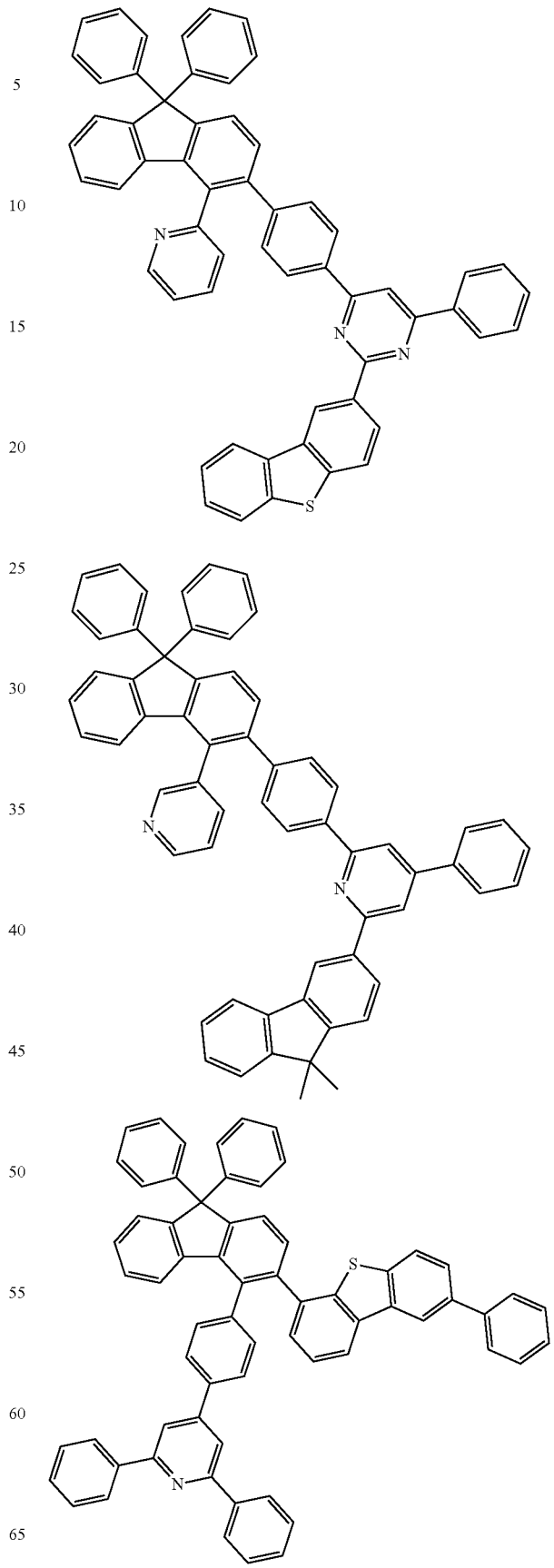

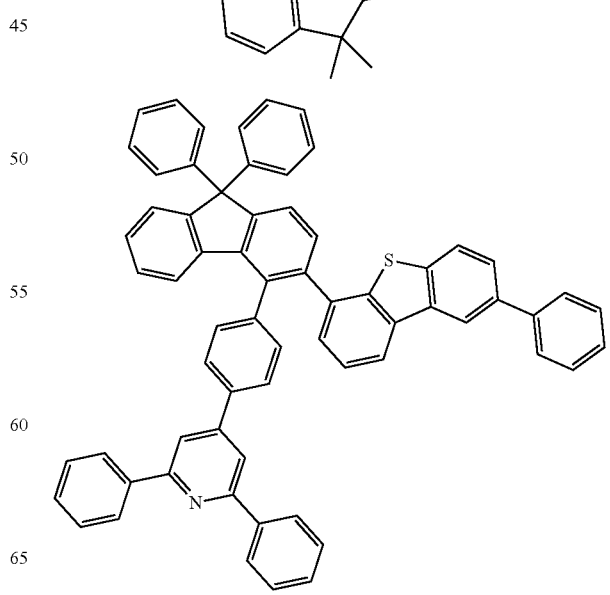

119
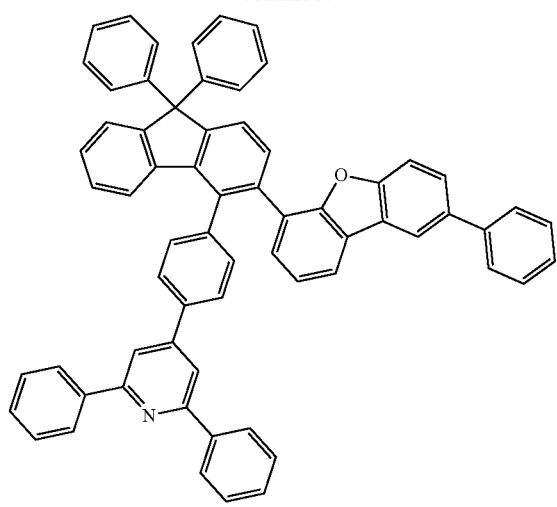
120
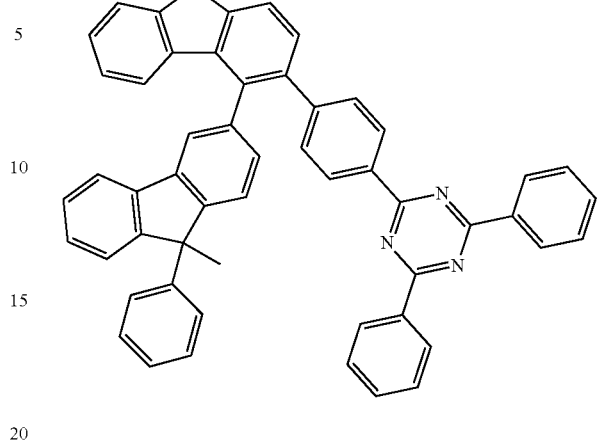
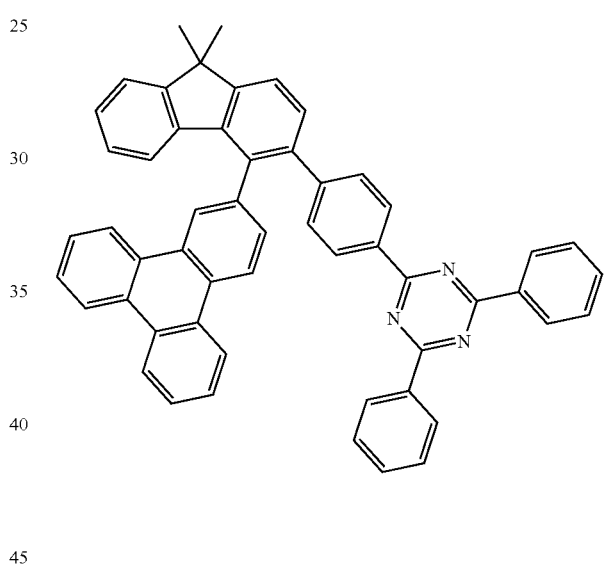
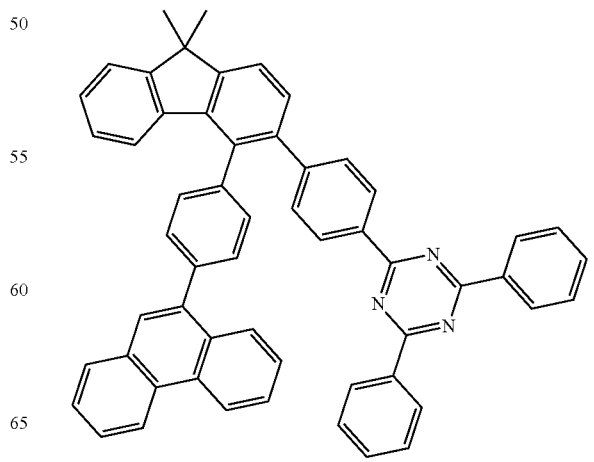

121
-continued
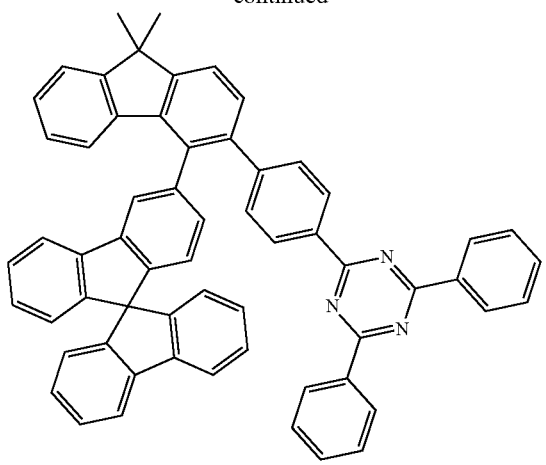
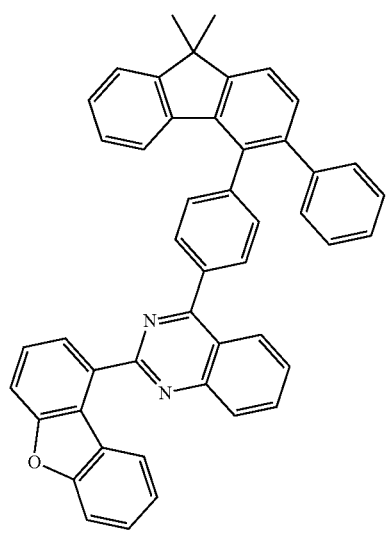
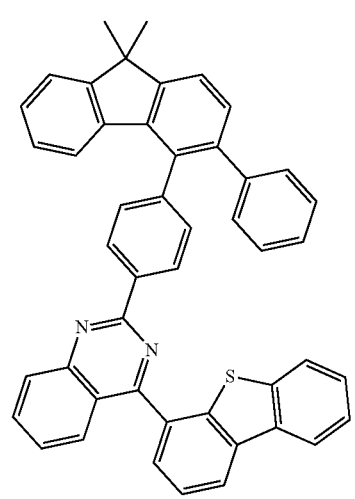
122
-continued
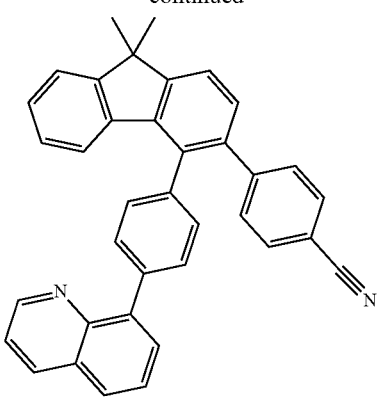
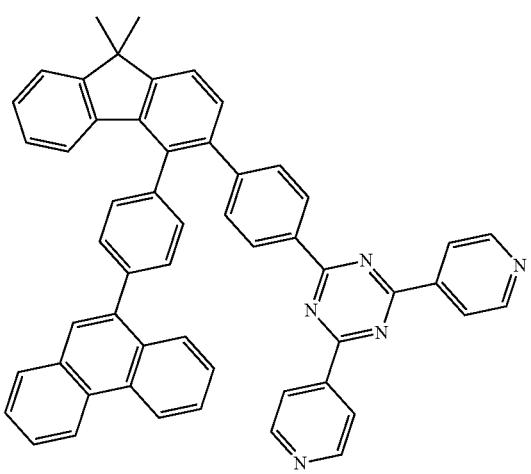
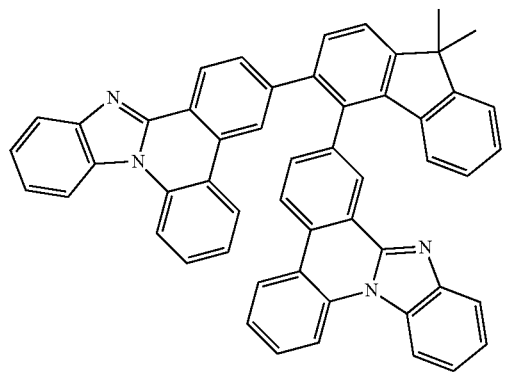

123
-continued
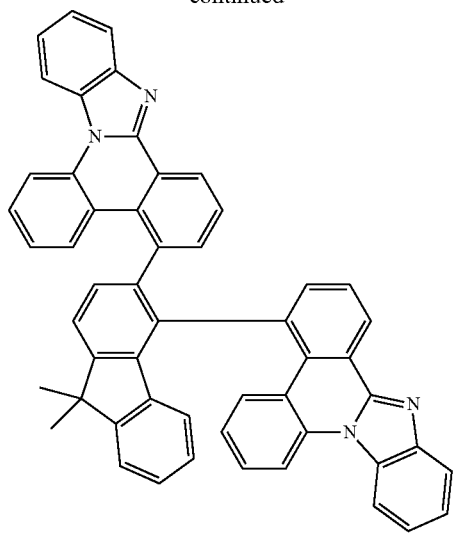
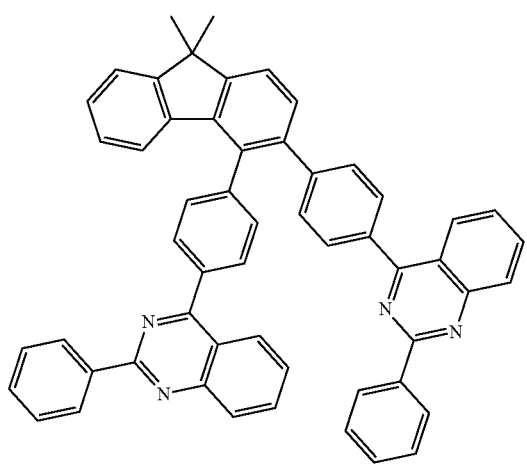
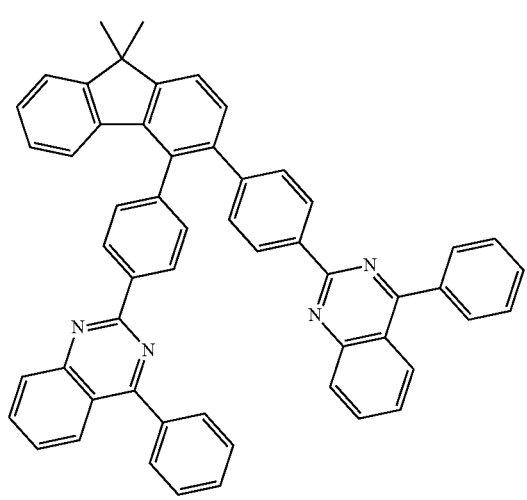
124
-continued
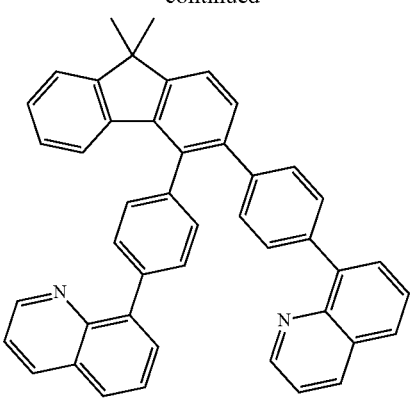
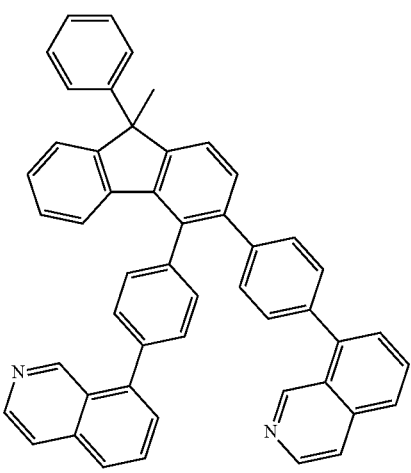
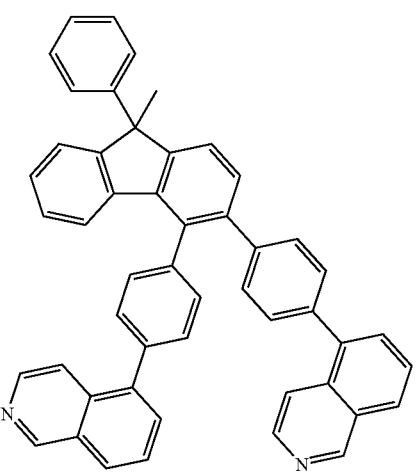

125
-continued
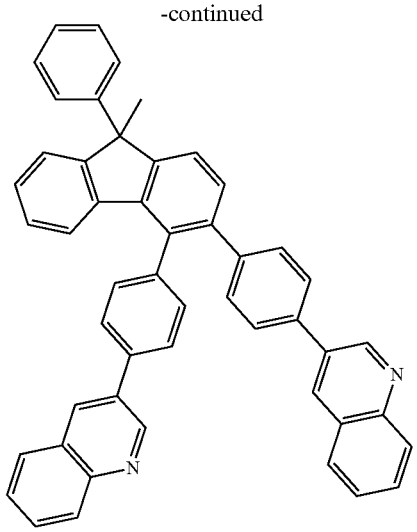
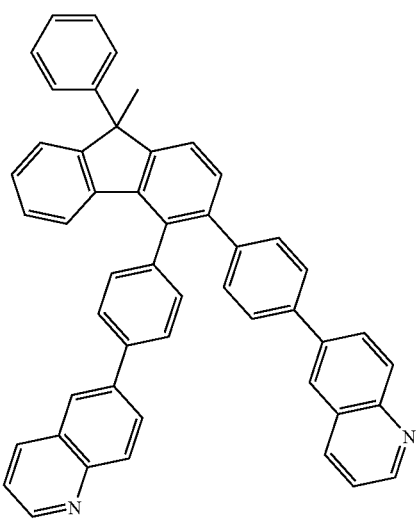
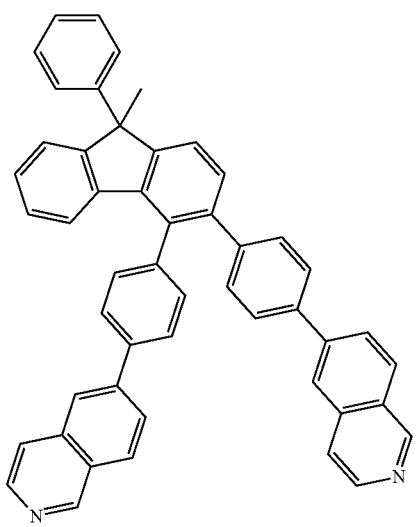
126
-continued
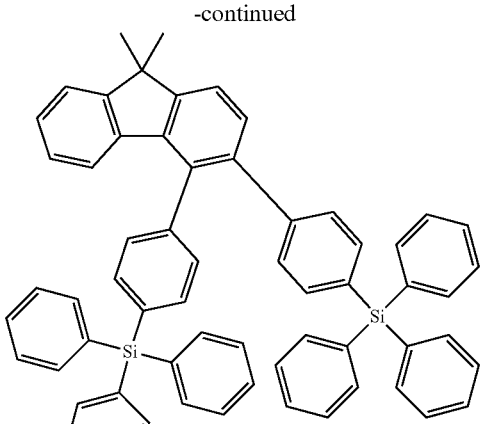
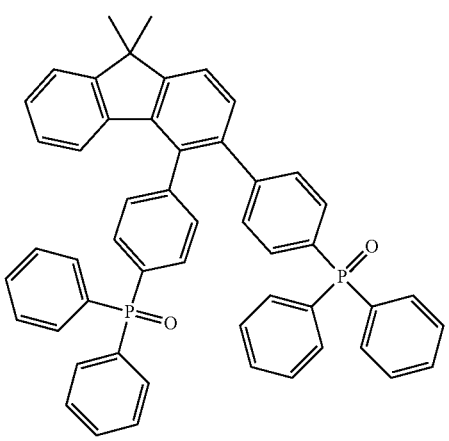
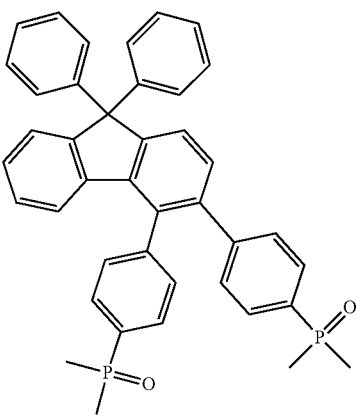

127
-continued
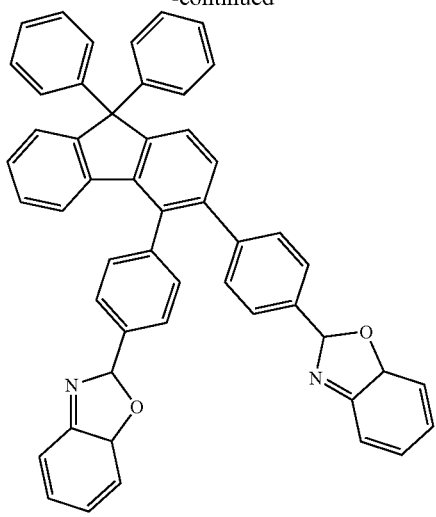
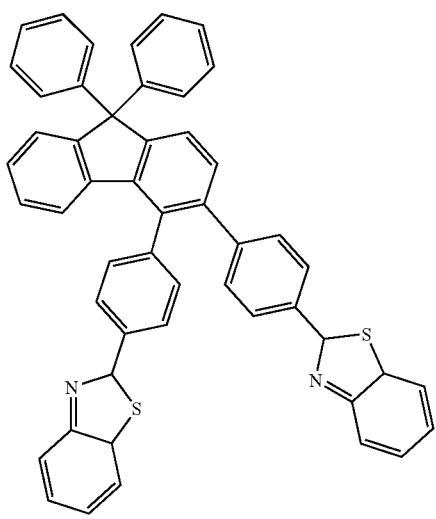
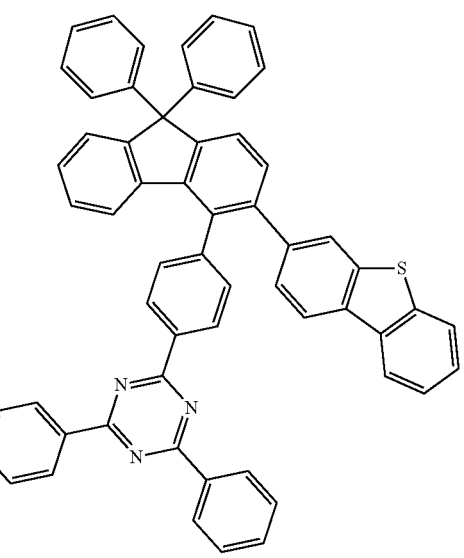
128
-continued
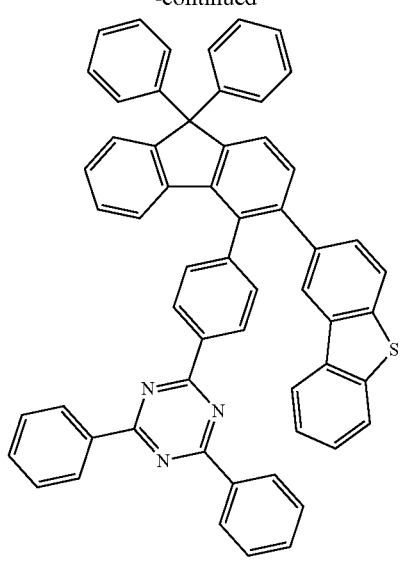
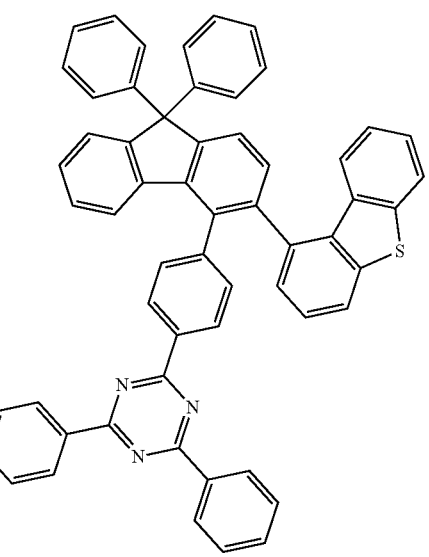
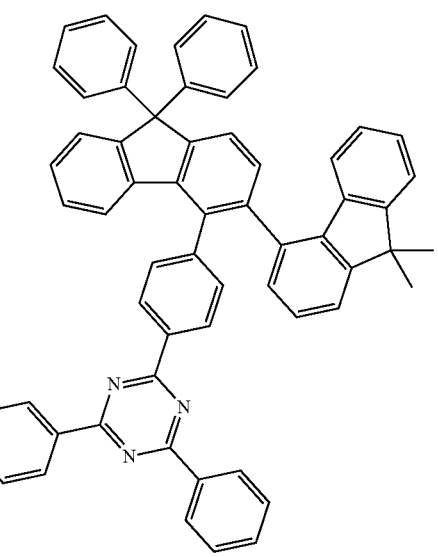

129
-continued
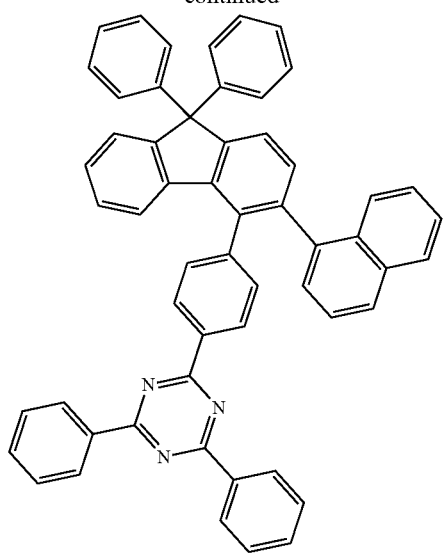
130
-continued
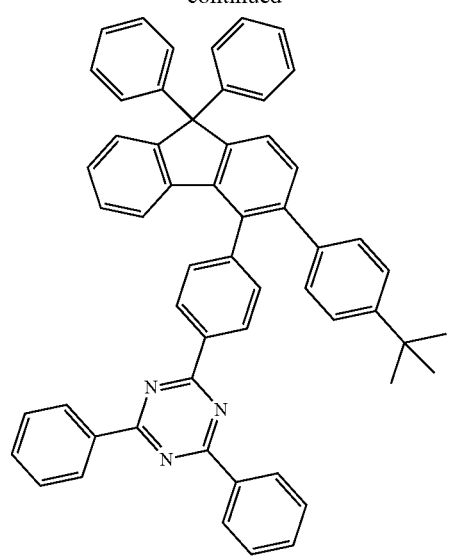
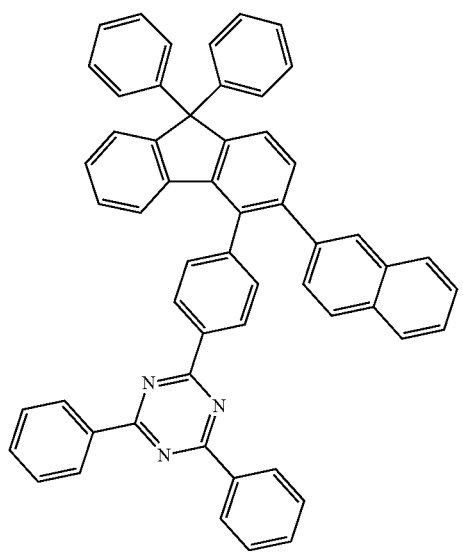
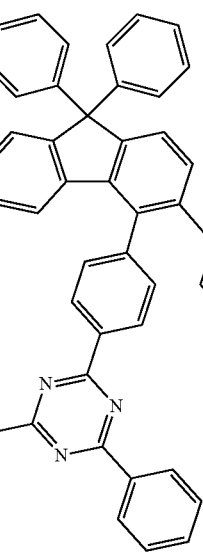
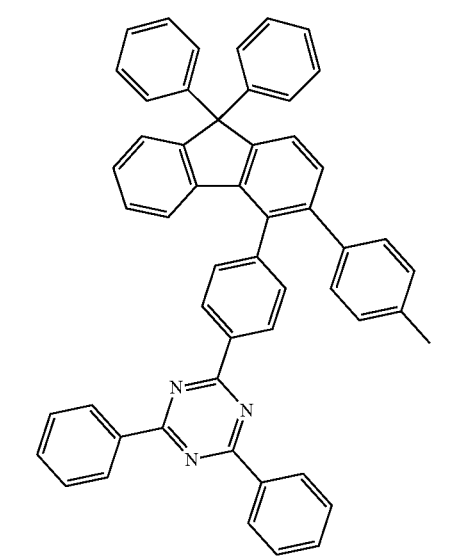
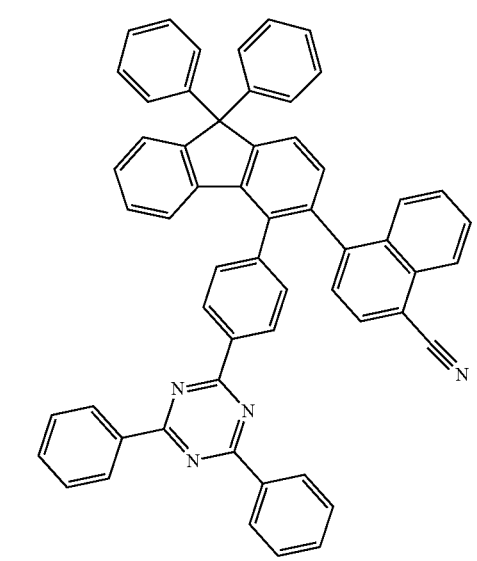

131
-continued
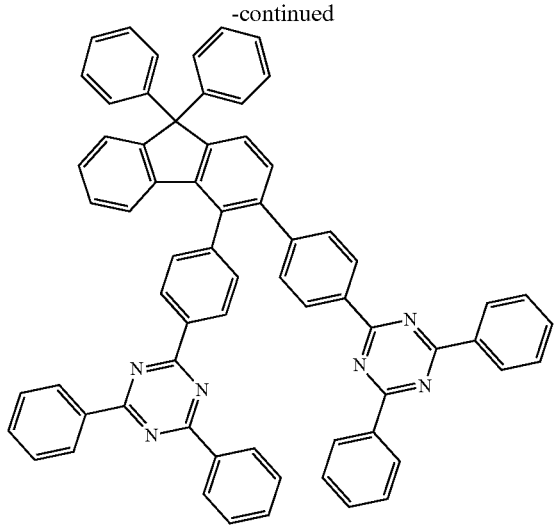
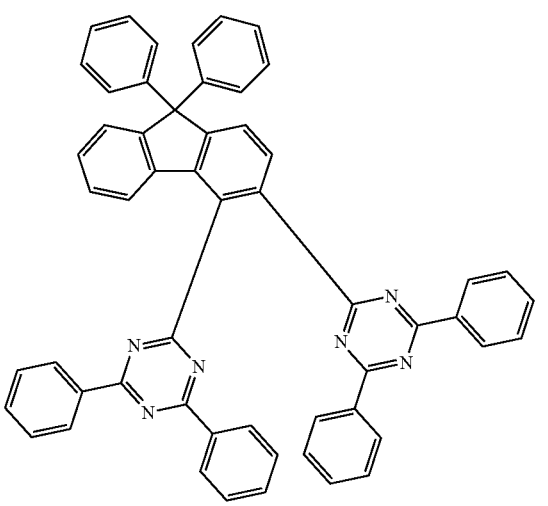
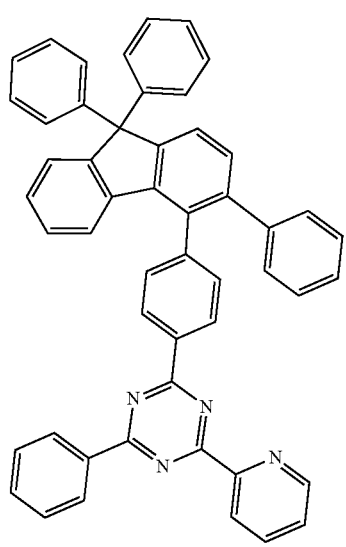
132
-continued
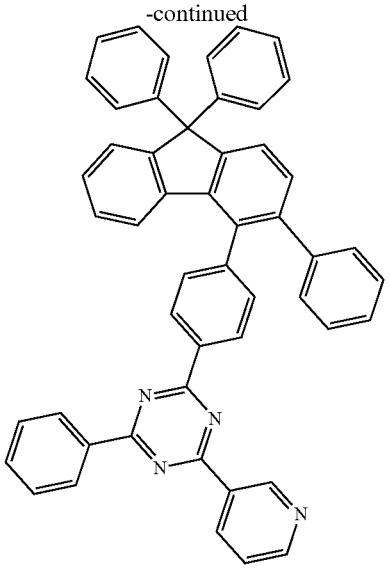
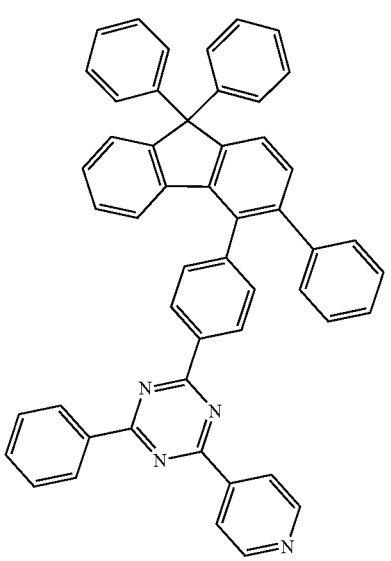
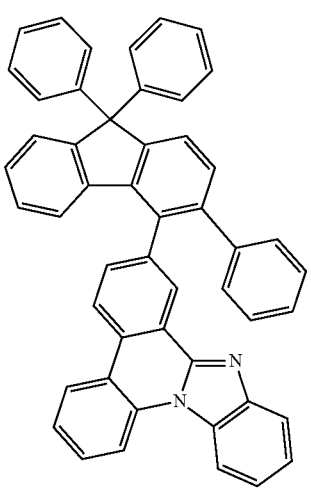

133
-continued
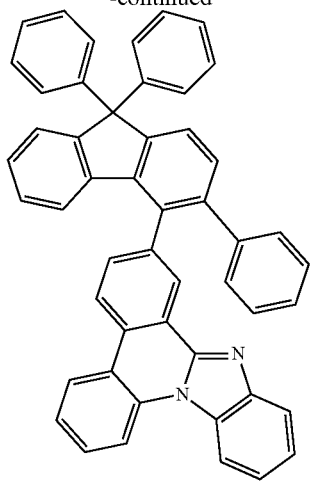
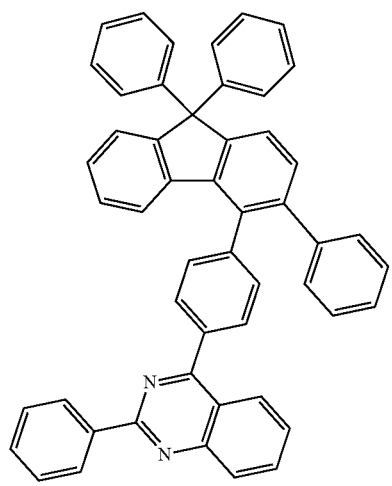
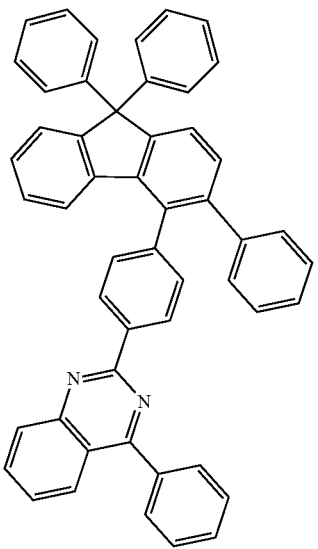
134
-continued
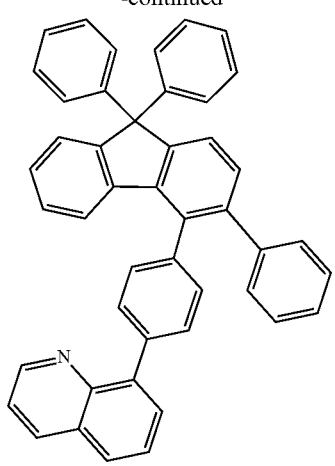
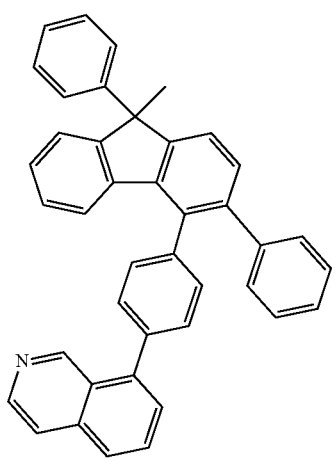
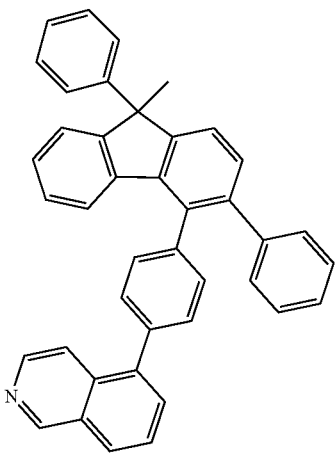

135
-continued
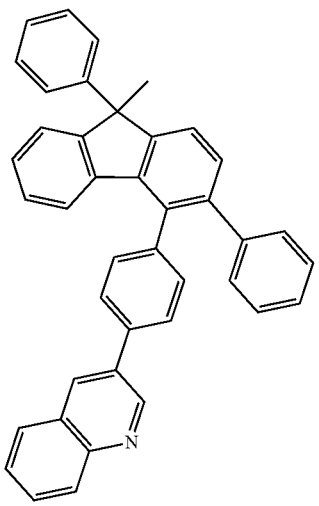
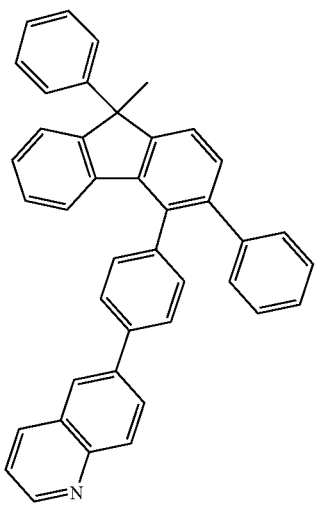
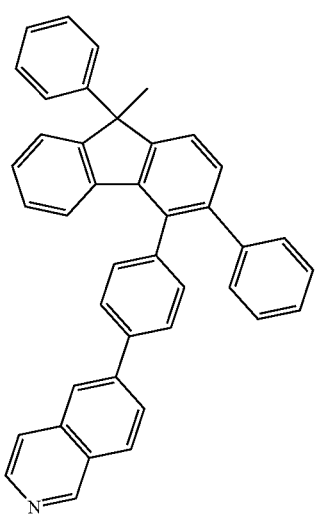
136
-continued
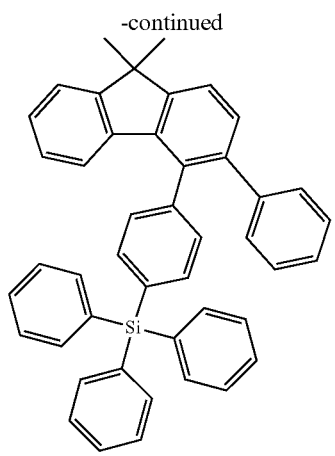
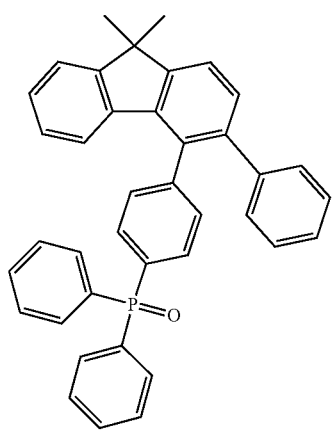
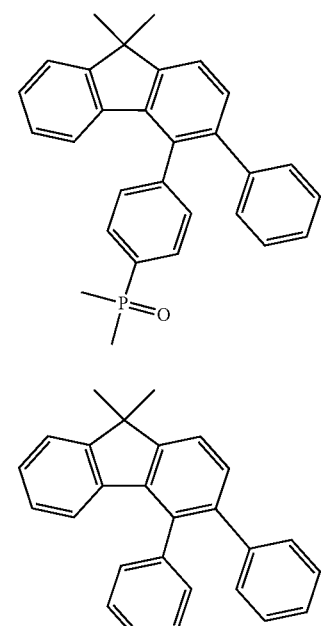
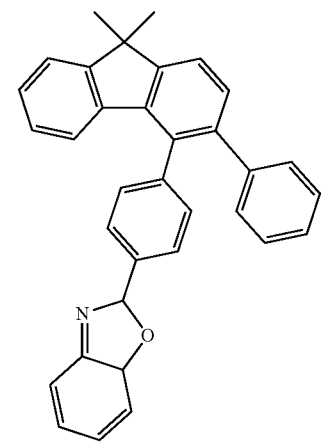

137
-continued
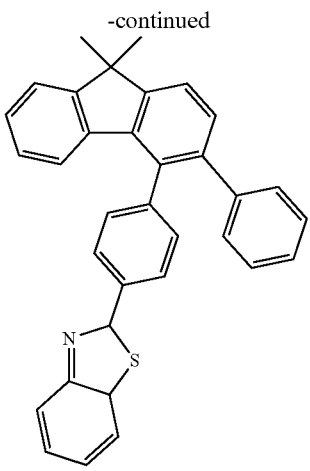
138
-continued
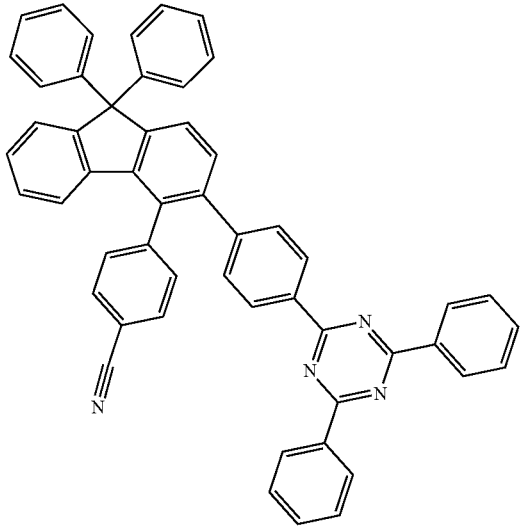
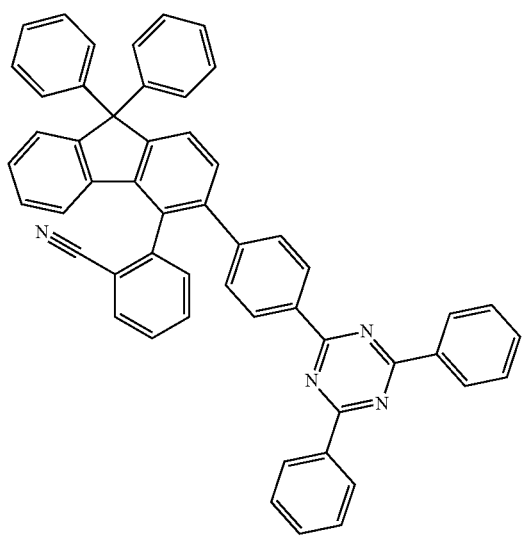
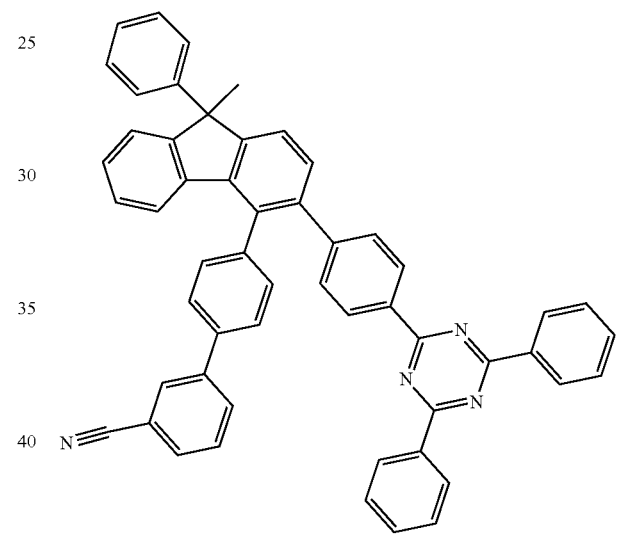
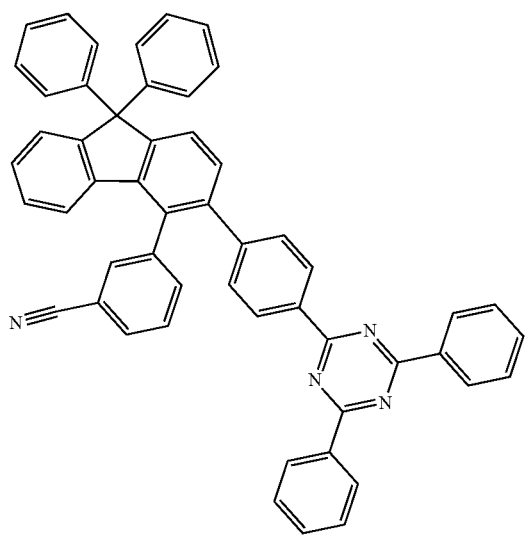
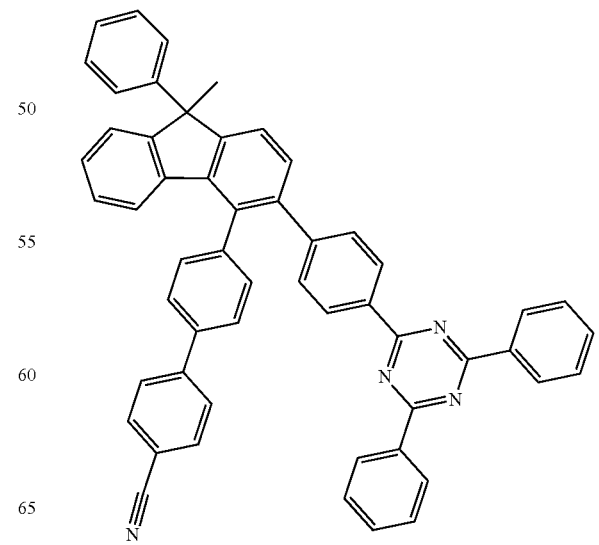

139
-continued
140
-continued
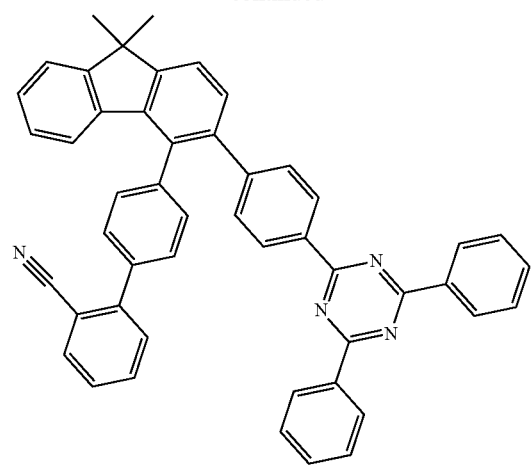
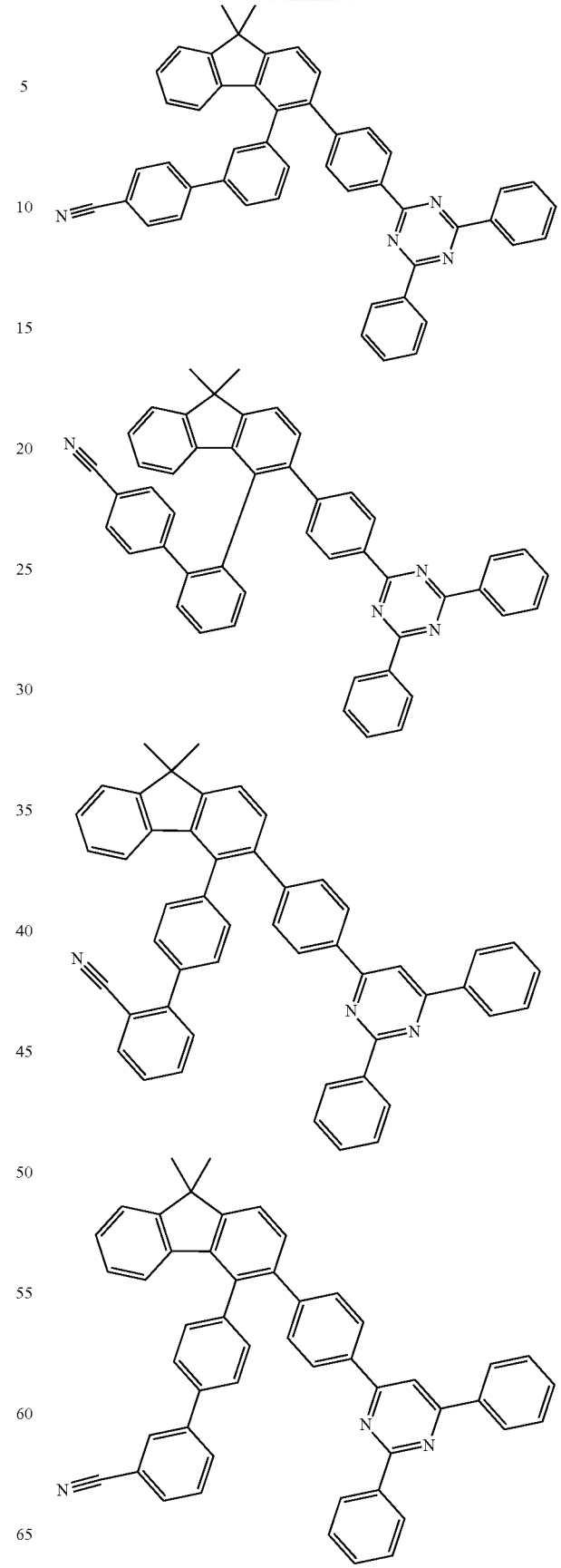

141
-continued
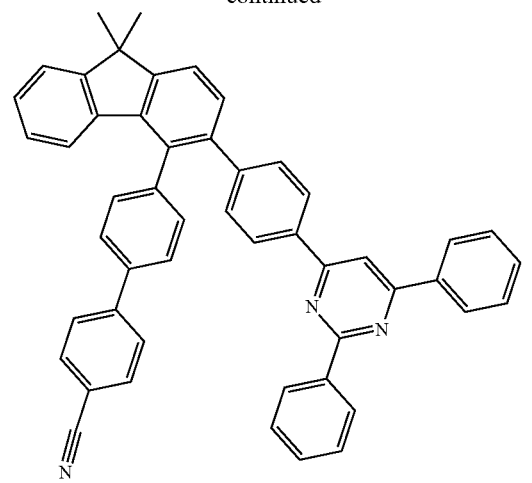
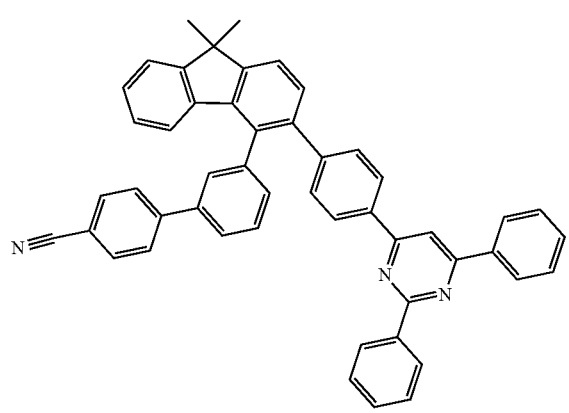
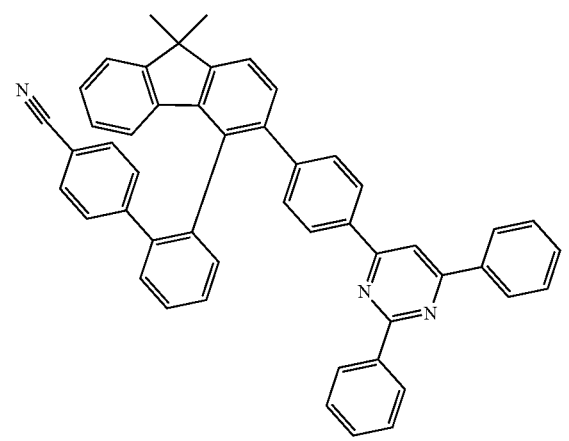
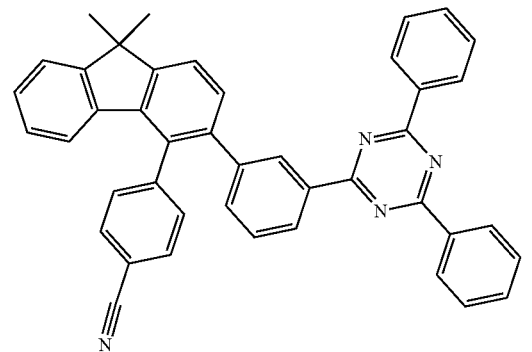
142
-continued
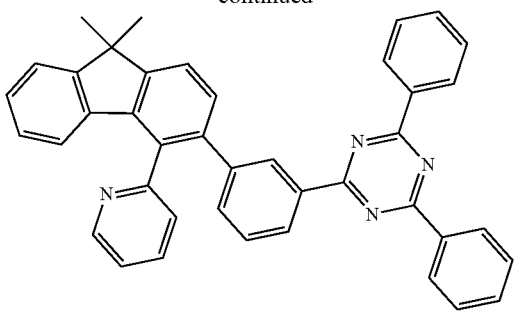
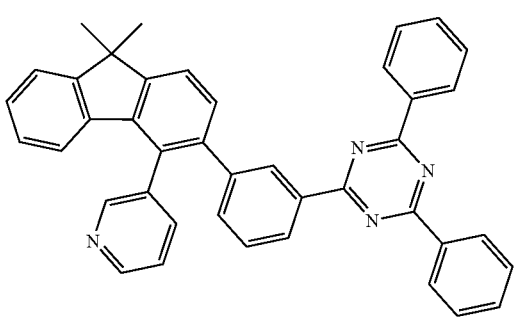
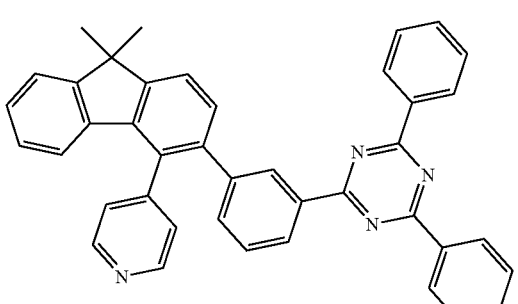
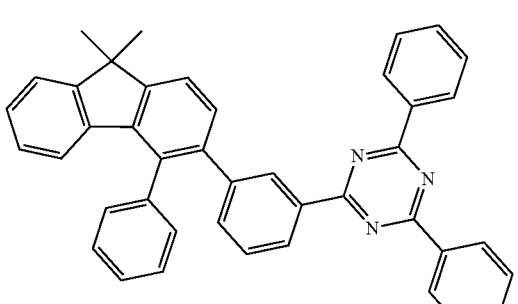
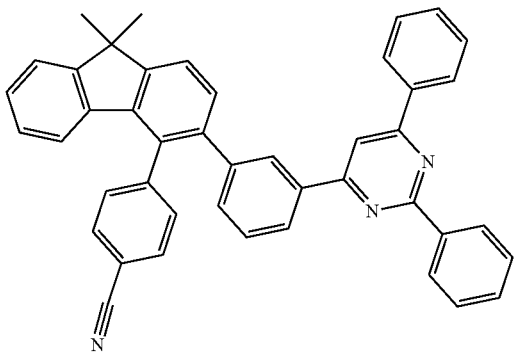

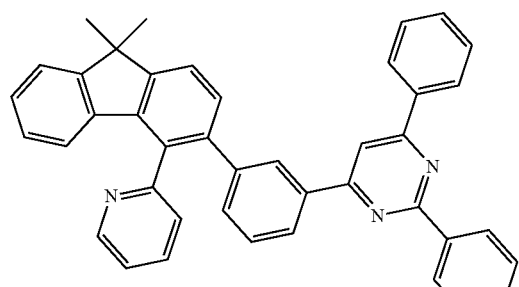
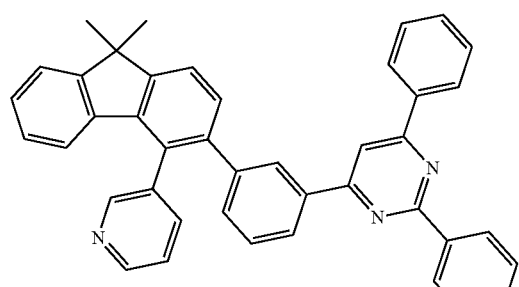
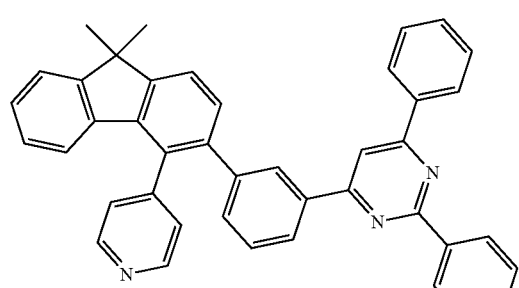
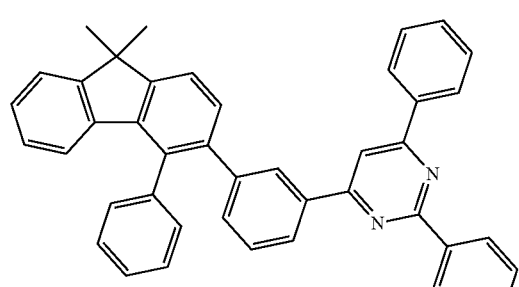
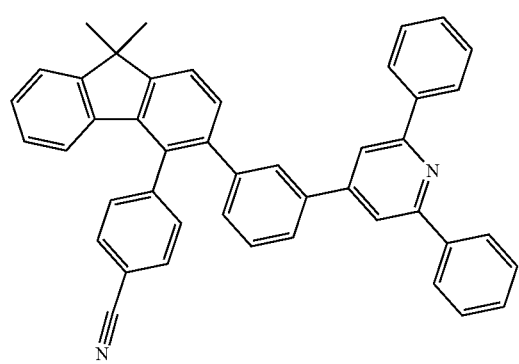
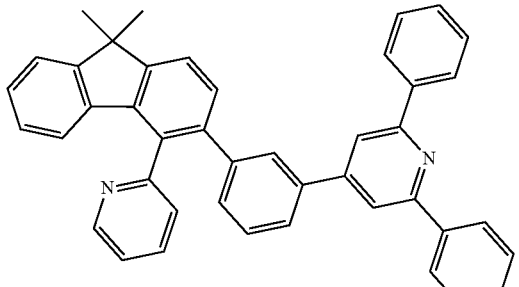
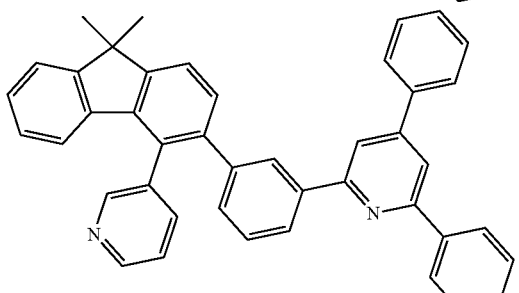
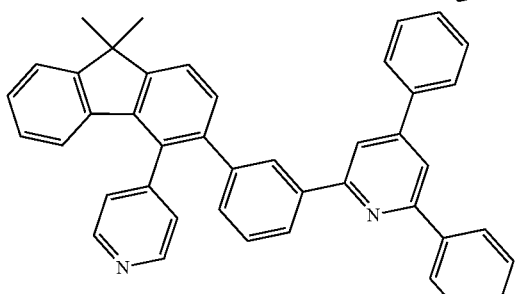
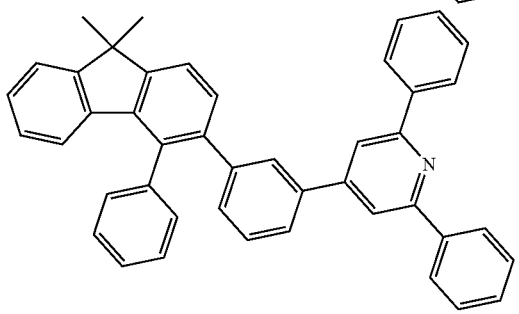
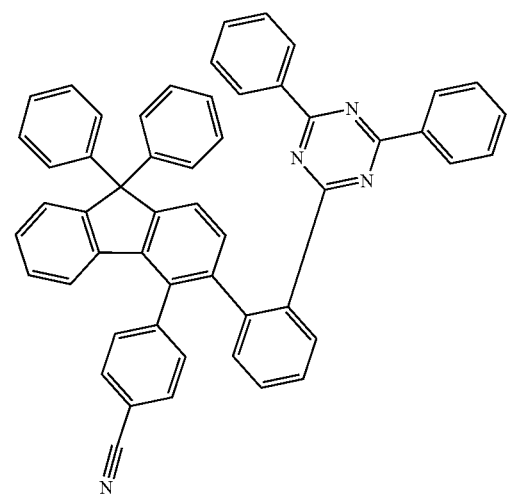

-continued
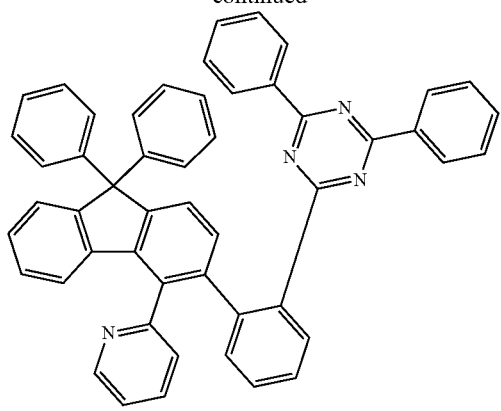
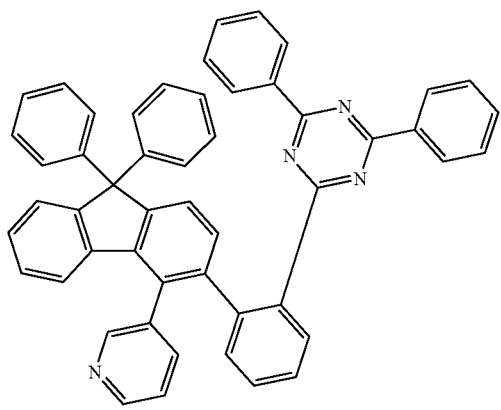
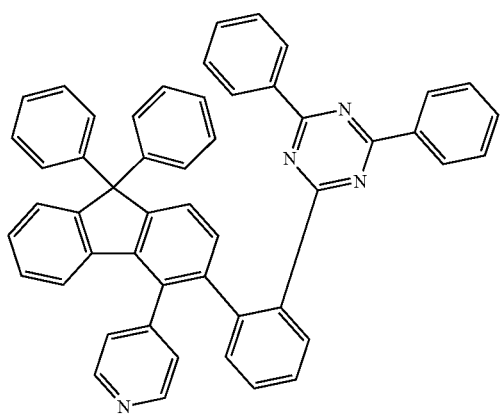
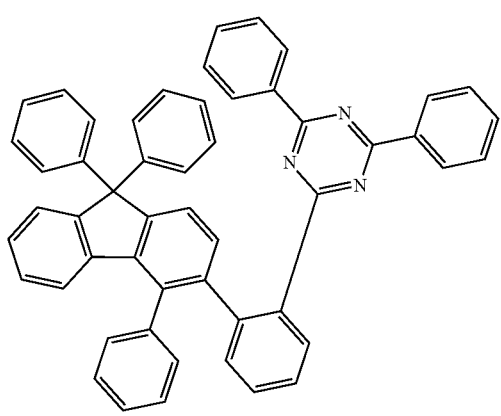
-continued
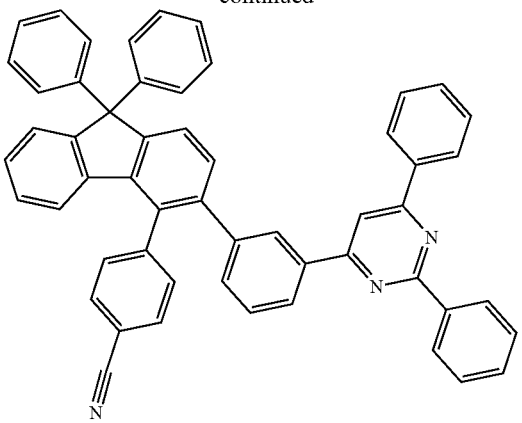
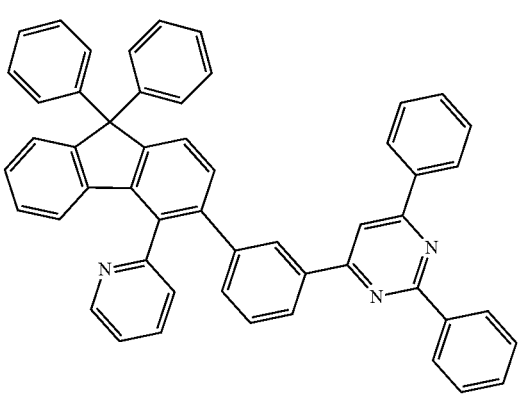
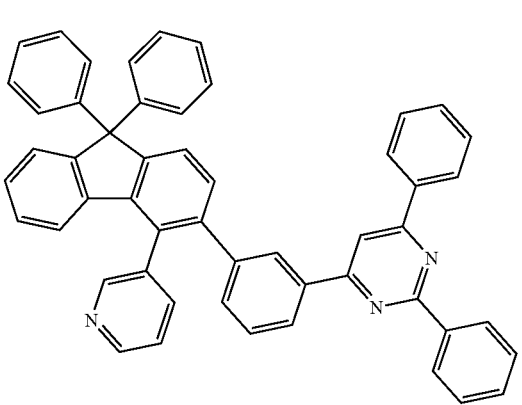
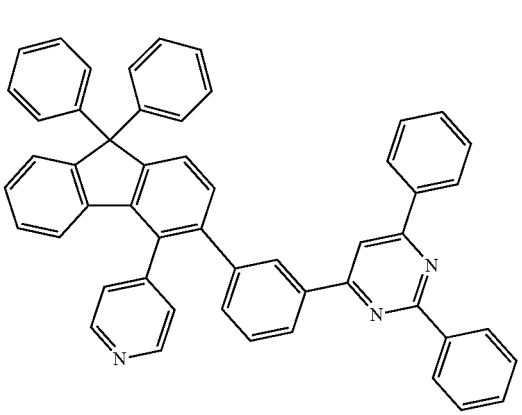

-continued
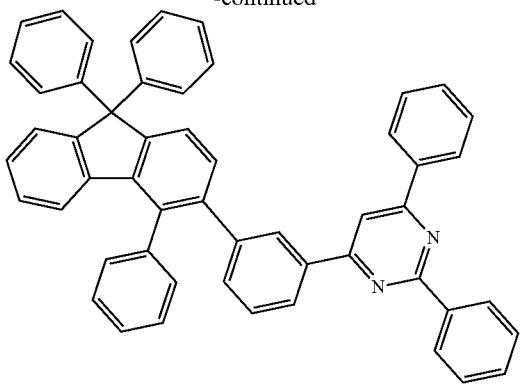
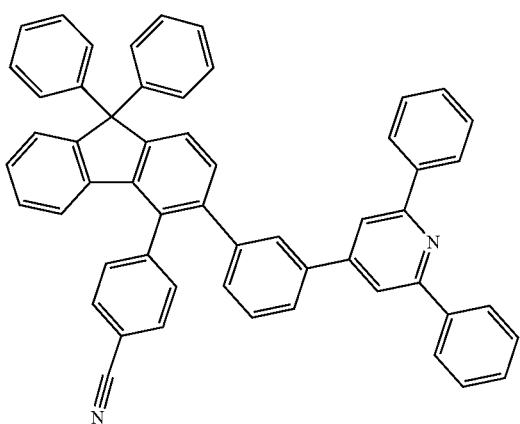
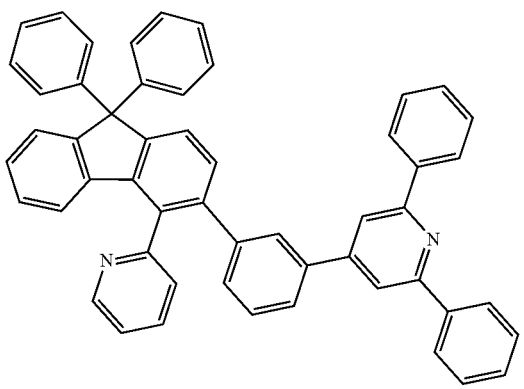
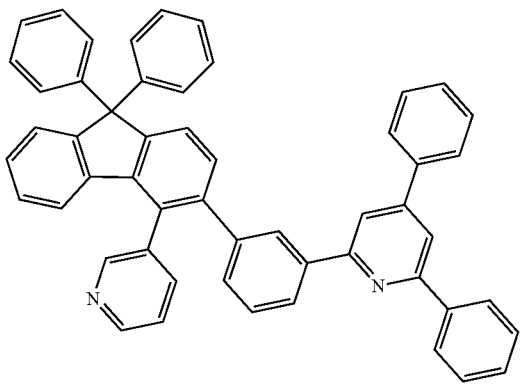
-continued
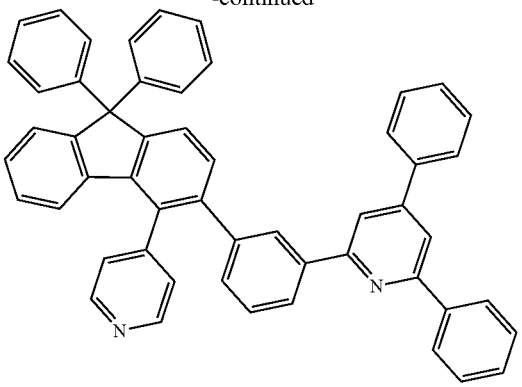
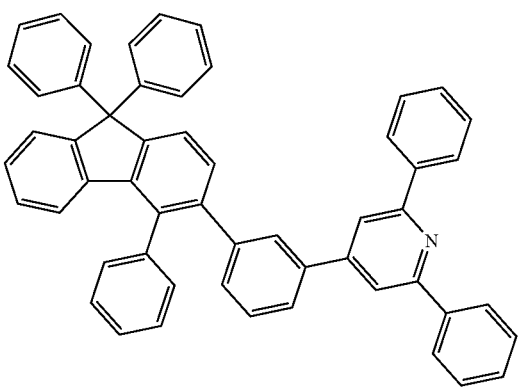
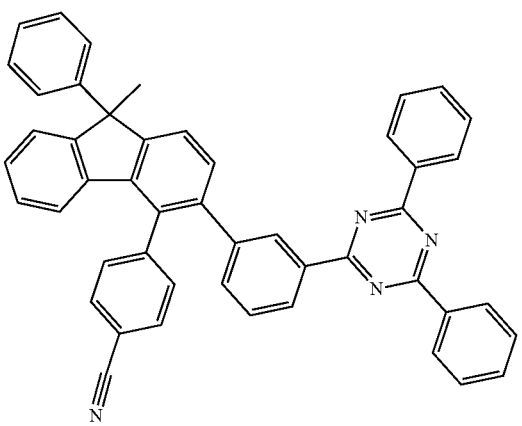
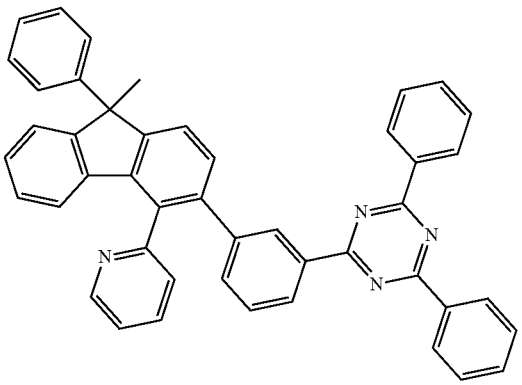

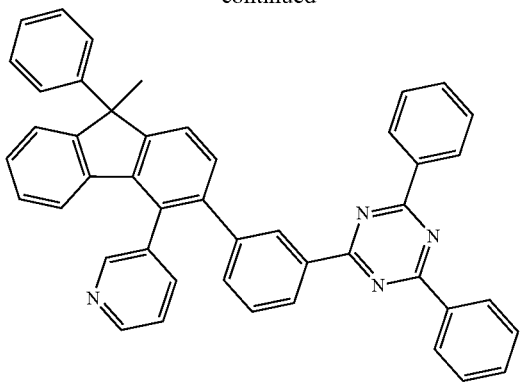
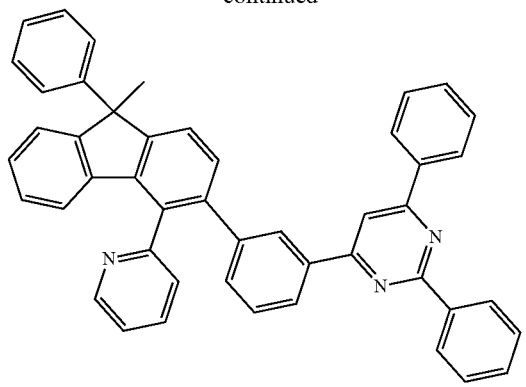
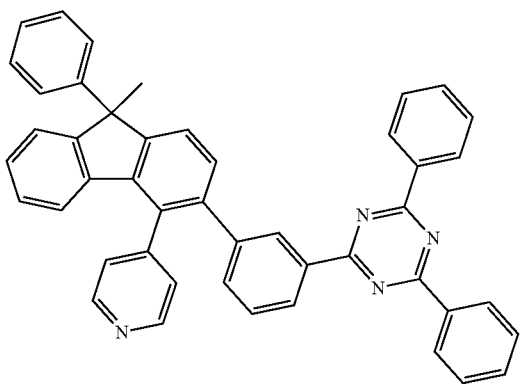
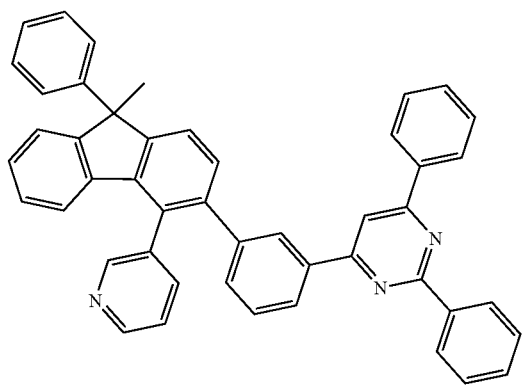
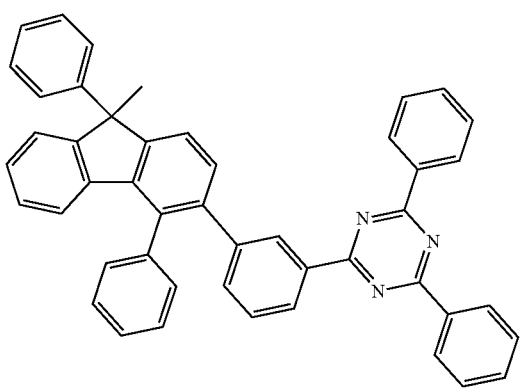
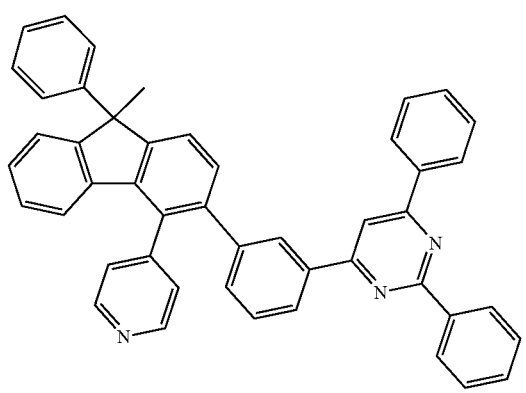
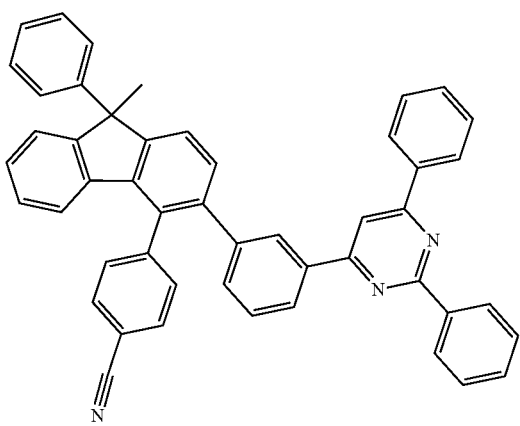
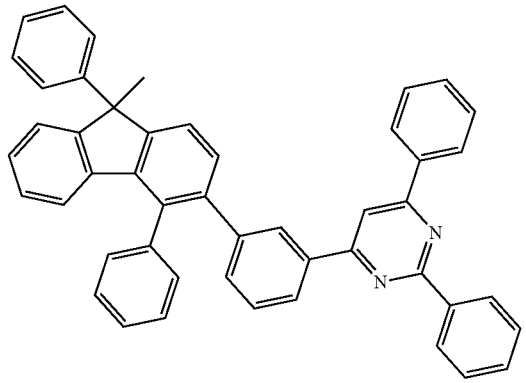

151
-continued
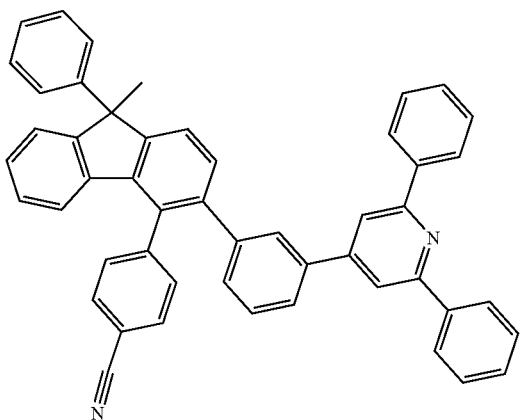
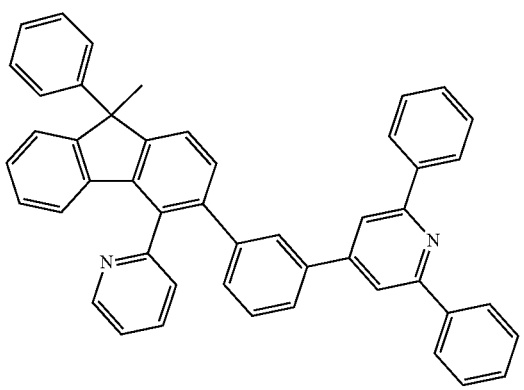
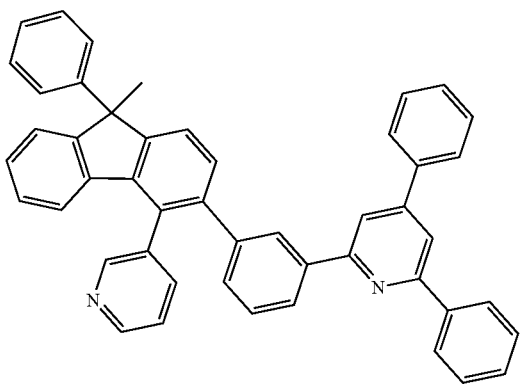
152
-continued
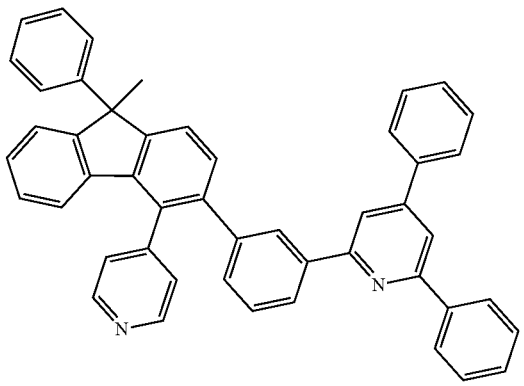
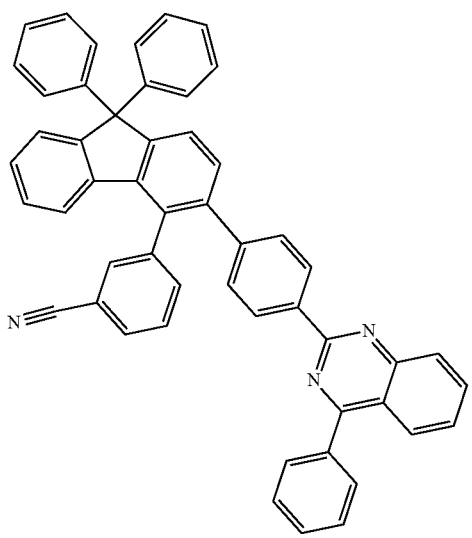

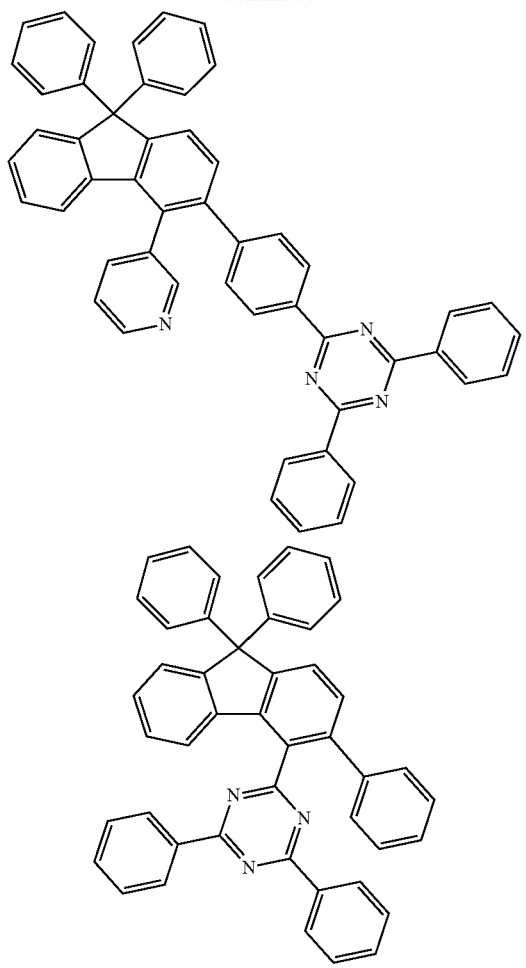

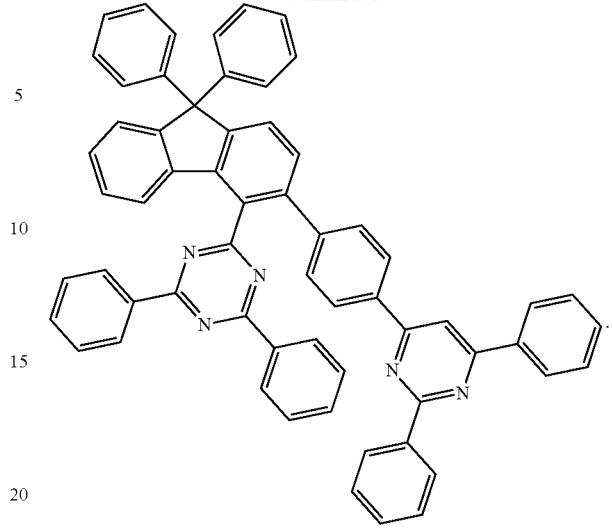

7. An organic light emitting device comprising:
a first electrode;
a second electrode provided opposite to the first electrode; and
one, two or more organic material layers provided between the first electrode and the second electrode,
wherein one or more layers of the organic material layers include the compound of claim 1.

8. The organic light emitting device of claim 7, wherein the organic material layer includes a hole blocking layer, an electron transfer layer, an electron injection layer, or an electron injection and transfer layer, and the hole blocking layer, the electron transfer layer, the electron injection layer, or the electron injection and transfer layer includes the compound.

* * * * *